(12) United States Patent
Holland et al.

(10) Patent No.: US 12,084,399 B2
(45) Date of Patent: Sep. 10, 2024

(54) CRYSTALLINE TRANILAST SALTS AND THEIR PHARMACEUTICAL USE

(71) Applicant: NUFORMIX TECHNOLOGIES LIMITED, London (GB)

(72) Inventors: Joanne Holland, Cambridge (GB); Christopher Frampton, Stowmarket (GB)

(73) Assignee: NUFORMIX TECHNOLOGIES LIMITED, London (GB)

(*) Notice: Subject to any disclaimer, the term of this patent is extended or adjusted under 35 U.S.C. 154(b) by 164 days.

(21) Appl. No.: 17/365,490

(22) Filed: Jul. 1, 2021

(65) Prior Publication Data

US 2021/0332003 A1 Oct. 28, 2021

Related U.S. Application Data

(62) Division of application No. 17/051,592, filed as application No. PCT/EP2019/071881 on Aug. 14, 2019, now Pat. No. 11,078,155.

(60) Provisional application No. 62/718,563, filed on Aug. 14, 2018.

(51) Int. Cl.
*A61K 31/196* (2006.01)
*C07C 235/38* (2006.01)

(52) U.S. Cl.
CPC ........ *C07C 235/38* (2013.01); *C07B 2200/13* (2013.01)

(58) Field of Classification Search
CPC ............................ A61K 31/196; C07C 233/55
USPC .......................................... 514/563; 562/455
See application file for complete search history.

(56) References Cited

U.S. PATENT DOCUMENTS

| | | | |
|---|---|---|---|
| 4,587,356 A | 5/1986 | Iizuka et al. | |
| 5,356,620 A | 10/1994 | Yamamoto et al. | |
| 9,512,064 B2 | 12/2016 | Holland et al. | |
| 10,422,398 B2 | 9/2019 | Jeon | |
| 11,078,155 B2 * | 8/2021 | Holland ................ | A61P 17/00 |
| 2005/0191614 A1 | 9/2005 | Cima et al. | |
| 2009/0264664 A1 | 10/2009 | Endo et al. | |

FOREIGN PATENT DOCUMENTS

| | | |
|---|---|---|
| EP | 0189861 A2 | 8/1986 |
| EP | 1946753 A1 | 7/2008 |
| ES | 8606846 A1 | 5/1986 |
| JP | S50140413 A | 11/1975 |
| JP | 2001187728 A | 7/2001 |
| JP | 2003519698 A | 6/2003 |
| JP | 2005247819 A | 9/2005 |
| JP | 2006306765 A | 11/2006 |
| KR | 20180078966 A | 7/2018 |
| WO | 2007046544 A1 | 4/2007 |
| WO | 2010/071865 A1 | 6/2010 |

OTHER PUBLICATIONS

Berge et al., "Pharmaceutical Salts", Journal of Pharmaceutical Sciences, 1977, vol. 66, No. 1, p. 1-19.
Ono, Analysis of current state of salt selection, Medicine, 2013, 73(3), p. 176-182.
Kawaguchi et al., "Drug and crystal polymorphism," Medicinal and Crystalline polymorphism, Journal of human environmental engineering, 2002, vol. 4, No. 2, p. 310-317.
"Regarding the establishment of new pharmaceutical standards and test methods", PAB Notice No. 568, May 1, 2001.
Takada, API Form Screening and Selection in Drug Discovery Stage, Pharm Stage, vol. 6, No. 10, Jan. 15, 2007, p. 20-25.
Yamano, Approach to crystal polymorph in process research of new drug, Journal of the Society of Synthetic Organic Chemistry, vol. 2007, 65(9), p. 907-913.
Geng et al., "Approach of Cocrystallization to Improve the Solubility and Photostability of Tranilast," Crystal Growth and Design, 2013, 13 (8), p. 3546-3553.
Office Action in JP 2020-555115, dated Nov. 8, 2022.
English translation of Research and Application of Tranilast in Other Disciplines, Edited by Cao Yuanhua and Chen Zhiqiang, China Women's Dermatology [M], Dec. 31, 2009.
International Search Report and Written Opinion in International Application No. PCT/EP2019/071881, dated Feb. 20, 2020.

* cited by examiner

*Primary Examiner* — Jeffrey H Murray
(74) *Attorney, Agent, or Firm* — RAPHAEL BELLUM PLLC

(57) ABSTRACT

The invention relates to crystalline tranilast salts. The crystalline tranilast salts, their preparation and their characterization are described and shown in the figures. The invention relates to pharmaceutical compositions containing a crystalline tranilast salt of the invention and a pharmaceutically acceptable carrier. The invention also relates to methods of treatment and the use of a therapeutically effective amount of a crystalline tranilast salt of the invention for treatment. The invention also relates to a method of preparing a liquid pharmaceutical composition comprising the step of dissolving a crystalline tranilast salt of the invention in a pharmaceutically acceptable solvent and to liquid pharmaceutical compositions prepared according to that method.

22 Claims, 41 Drawing Sheets

FIG. 21 TGA Trace for the Crystalline 1:1 Tranilast N-ethylglucamine Salt

ORTEP drawing of the Crystalline 1:1 Tranilast Potassium Monohydrate Salt

ORTEP drawing of the Crystalline 1:1 Tranilast Ethanolamine Salt

DSC Trace for the Crystalline 1:1 Tranilast Ethanolamine Salt

Dissolution profiles for the crystalline 1:1 tranilast salts, 1:1 tranilast nicotinamide and Rizaben® cocrystal in FaSSIF V2 at 37 °C

CRYSTALLINE TRANILAST SALTS AND THEIR PHARMACEUTICAL USE

CROSS-REFERENCE TO RELATED APPLICATIONS

This application is a divisional application of U.S. application Ser. No. 17/051,592, filed Oct. 29, 2020; which is a 371 of PCT International Application No. PCT/EP2019/071881, filed Aug. 14, 2019; which claims priority to U.S. patent application No. 62/718,563 filed Aug. 14, 2018, which is incorporated herein by reference.

FIELD OF THE INVENTION

The invention relates to crystalline tranilast salts, therapeutic uses of the crystalline salts and pharmaceutical compositions containing them.

BACKGROUND

Tranilast, (2-[[3-(3,4-dimethoxyphenyl)-1-oxo-2-propenyl]amino] benzoic acid, shown below), was originally developed as an anti-allergy drug due to its ability to inhibit the release of inflammatory mediators, such as histamine, from mast cells and basophils (P. Zampini. *Int J Immunopharmacol.* 1983; 5(5): 431-5).

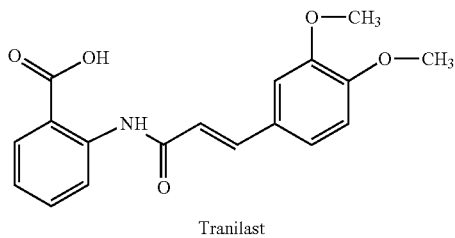 [SMILES: COc1ccc(/C=C/C(=O)Nc2ccccc2C(=O)O)cc1OC]

Tranilast

Tranilast has been marketed in Japan, China and South Korea by Kissei Pharmaceutical Co. Ltd, for allergic conditions such as allergic conjunctivitis, bronchial asthma, allergic rhinitis and atopic dermatitis, under the Rizaben® brand name for more than thirty years. More recently tranilast has also been shown to have anti-proliferative properties. Tranilast was shown to inhibit the proliferation of fibroblasts and suppress collagen synthesis (M. Isaji. *Biochem Pharmacol.* 1987; 36: 469-474) and also to inhibit the transformation of fibroblasts to myofibroblasts and their subsequent contraction (M. Isaji. *Life Sci.* 1994; 55: 287-292). This additional behaviour led to tranilast gaining additional approval for the treatment of keloids and hypertrophic scars.

Over recent years many researchers have explored the anti-proliferative effects of tranilast to assess its potential in fibrotic and cancerous conditions. Its anti-proliferative action is believed to be due to its ability to inhibit transforming growth factor beta (TGF-β) (H. Suzawa. *Jpn J Pharmacol.* 1992 October; 60(2): 91-96). Fibrosis is a condition that can affect most organs of the body and fibroblast proliferation, differentiation and collagen synthesis are known to be key factors in the progression of most types of fibrosis. Tranilast has been shown in-vivo to have potential beneficial effects in numerous fibrotic conditions. Tranilast has been shown in-vivo to have potential in lung fibrosis (M. Kato. *Eur Respir J.* 2013; 42(57): 2330), kidney fibrosis (D J Kelly, *J Am Soc Nephrol.* 2004; 15(10): 2619-29), cardiac fibrosis (J Martin, *Cardiovasc Res.* 2005; 65(3): 694-701), ocular fibrosis (M J Moon, *BMC Opthalmol.* 2016; 16: 166) and liver fibrosis (M Uno, *Hepatology.* 2008; 48(1): 109-18.

Tranilast's anti-tumor action has also recently been demonstrated, in-vitro and in-vivo. Tranilast has been shown to inhibit the proliferation, apoptosis and migration of several cell lines including breast cancer (R. Chakrabarti. *Anticancer Drugs.* 2009 June; 20(5): 334-45) and prostate cancer (S. Sato. *Prostate.* 2010 February; 70(3): 229-38) cell lines. In a study of mammary carcinoma in mice tranilast was found to produce a significant reduction in metastasis (R. Chakrabarti. *Anticancer Drugs.* 2009 June; 20(5): 334-45). In a pilot study in humans, tranilast was shown to have the potential to improve the prognosis of patients with advanced castration-resistant prostate cancer (K. Izumi. *Anticancer Research.* 2010 July; 30: 73077-81). In-vitro studies also showed the therapeutic potential of tranilast in glioma (M Platten. *Int J Cancer.* 2001; 93:53-61), pancreatic cancer (M Hiroi, *J Nippon Med Sch.* 2002; 69: 224-234) and gastric carcinoma (M Yashiro, *Anticancer Res.* 2003; 23: 3899-3904).

Given the wide range of fibrotic conditions and cancers for which tranilast could have a potential therapeutic benefit, as well as the different patient types and specific areas of the body requiring treatment, it is anticipated that patients would benefit from having multiple delivery methods for the administration of tranilast so as to best suit the patient's needs. The pharmaceutical compositions could include, for example, a solid oral dosage, a liquid oral dosage, an injectable composition, an inhalable composition, a topical composition or a transdermal composition.

Kissei Pharmaceutical Co. Ltd explored the anti-proliferative effect of tranilast in the prevention of restenosis associated with coronary intervention. In a Phase II clinical study Kissei found that the current approved dose of tranilast (300 mg/day) was insufficient to prevent restenosis and that a higher dose of 600 mg/day was needed to achieve a decrease in restenosis rates (H. Tamai, *Am Heart J.*1999; 138(5): 968-75). However, it was found that a 600 mg daily dosage can result in a ten-fold inter-patient variation in plasma concentrations of the drug (30-300 μmol/L) (H Kusama, *Atherosclerosis.* 1999; 143: 307-313) and in the Phase III study of tranilast for the prevention of restenosis the dose was further increased to 900 mg daily (D Holmes, *Circulation.* 2002; 106(10): 1243-1250).

The marketed oral form of tranilast (Rizaben®) contains tranilast in its pure crystalline form. Crystalline tranilast has extremely low aqueous solubility (solubility of 14.5 μg/ml in water and 0.7 μg/ml in pH 1.2 buffer solution (Society of Japanese Pharmacopoeia. 2002)). Whilst, high energy amorphous forms are often used as a means of improving the solubility of poorly soluble drug compounds, literature shows that an amorphous form of tranilast is not completely photostable in the solid state and that it undergoes photodegradation on storage when exposed to light (S. Onoue. *Eur J Pharm Sci.* 2010; 39: 256-262).

It is expected that the very low solubility of tranilast is a limiting factor in the oral bioavailability of the drug. Given the limited time any drug has to firstly dissolve in the gastrointestinal tract and then be absorbed into the bloodstream, this issue will become even more limiting as the oral dose of tranilast is increased. The poor solubility of tranilast is also possibly a key factor in the high inter-patient variability reported for higher dose tranilast pharmacokinetics. As a BCS class II drug (low solubility/high permeability) it is expected that absorption from the gastrointestinal tract is hampered by the dissolution rate of the drug in gastrointestinal media as well as its overall solubility. For treatment of chronic proliferative diseases such as fibrosis and cancer it is vital for the delivery method of a drug to produce consistent, predictable plasma levels that are maintained above the minimum effective concentration. To achieve efficacious oral delivery of tranilast at higher doses there is a need for new solid forms of the drug with both high solubility and rapid dissolution rates.

Given the severity of conditions involving cancer or fibrosis there is also a need for systemic treatment options by which tranilast can be delivered by healthcare specialists that do not require the patient to swallow solid oral dosage forms. Alternative dosage forms suitable for these needs could include, for example, injectable compositions, liquid oral formulations or nebulized inhaled formulations. These would require a liquid formulation of tranilast suitable for systemic delivery.

Given the potential of tranilast to treat ocular diseases, such as allergic conjunctivitis, Kissei Pharmaceutical Co. Ltd recognised the need to develop an eye drop formulation of tranilast for localised treatment. However, as well as having very low aqueous solubility, tranilast is also photochemically unstable when stored in solution, resulting in significant degradation (N Hori, *Chem. Pharm. Bull.* 1999; 47(12): 1713-1716). Therefore, the only way Kissei were able to achieve an eye drop liquid composition of tranilast was to use both solubilising and stabilising agents in the formulation (U.S. Pat. No. 5,356,620). The resulting 0.5% (w/v) eye drop formulation is currently also marketed under the Rizaben® brand name. However, the focus of this formulation and of the subsequent research that has attempted to produce alternative solution formulations of tranilast has always been solely on external delivery of tranilast using compositions such as eye drops and skin ointments etc. None of the liquid formulations of tranilast previously described have been produced for systemic delivery such as for oral or IV delivery. Excipients used in the previously reported external preparations are not suitable for systemic delivery. Also, despite the successful development of an eye drop formulation of tranilast, the package insert of the marketed Rizaben® eye drops states that the product should not be stored in a refrigerator as crystals may precipitate.

Thus, there remains a need for aqueous pharmaceutical compositions of tranilast suitable for systemic delivery. Given the potential photochemical degradation issue of long term storage of tranilast in solution and also the disadvantage of the larger storage facilities needed to store bulkier solution based formulations it would also be advantageous to develop a stable highly soluble solid form of tranilast that can be quickly dissolved at the time of treatment by the patient or healthcare provider to produce the required liquid formulation.

Following efforts to make a liquid formulation of tranilast, Kissei made the statement that tranilast and pharmaceutically acceptable salts thereof are too insoluble in water to prepare an aqueous solution (U.S. Pat. No. 5,356,620). Since that US patent the only crystalline pharmaceutically acceptable salt to have been published is the sodium salt (N Geng, *Cryst. Growth Des.* 2013; 13: 3546-3553). In line with the findings of Kissei the authors of this paper stated that the apparent solubility of the crystalline tranilast sodium salt is even less than that of pure tranilast. Also, when they performed a dissolution study of tranilast in a sodium containing media they found that as the tranilast dissolved it gradually precipitated out of solution as its sodium salt indicating that the sodium salt has a lower thermodynamic solubility than the pure drug. The authors of this paper also successfully prepared the non-pharmaceutically acceptable crystalline cytosine salt of tranilast. Despite this crystalline cytosine salt showing approximately a two-fold solubility improvement over pure crystalline tranilast, not only would this crystalline cytosine salt not be suitable for systemic delivery to a patient due to cytosine not having FDA acceptability but this improvement in solubility would not be great enough to produce high dose tranilast liquid formulations such as an injectable formulation.

Patent application EP1946753 discloses an attempt to prepare an external preparation of tranilast and claims the preparation of ionic liquid salts of tranilast with organic amines. The inventors claim that blending tranilast with the organic amine results in a liquid form. This application does not disclose the formation of any solid state, crystalline tranilast salts with organic amines. They demonstrate that these ionic liquid forms of tranilast have higher solubility in solvents suitable for external application to the skin and that these preparations have higher photostability than pure tranilast in the same formulation. However, this improved photostability still results in a significant proportion of the tranilast being photo-degraded and would not be suitable for long term storage. Also, the solvents used for preparation of these ionic liquid salt formulations are not suitable for internal delivery of tranilast. Moreover, there is no mention in EP1946753 of improved solubility in aqueous or bio-relevant media.

Summary of the Invention

The invention relates to crystalline tranilast salts. In particular, the invention relates to a crystalline 1:1 tranilast n-methylglucamine form I salt; a crystalline 1:1 tranilast n-methylglucamine form II salt; a crystalline 1:1 tranilast l-lysine salt; a crystalline 1:1 tranilast diethylamine salt; a crystalline 1:1 tranilast n-ethylglucamine salt; a crystalline 1:1 tranilast potassium monohydrate salt; a crystalline 1:1 tranilast diethanolamine salt; and a crystalline 1:1 tranilast ethanolamine salt. The invention relates to pharmaceutical compositions containing a crystalline tranilast salt of the invention and a pharmaceutically acceptable carrier. Tranilast possesses anti-allergic, anti-fibrotic, anti-inflammatory, anti-tumor, neurogenesis enhancing and angiogenesis inhibitory properties and as such may be useful for the treatment of the diseases, disorders and conditions associated with such properties, as discussed above. The crystalline tranilast salts of the invention may be used in the same way as tranilast but have improved properties over tranilast and other forms of tranilast. The invention also relates to a method of preparing a liquid pharmaceutical composition comprising the step of dissolving a crystalline tranilast salt according the invention in a pharmaceutically acceptable solvent and to liquid pharmaceutical compositions prepared according to that method.

DETAILED DESCRIPTION

Figure 1:
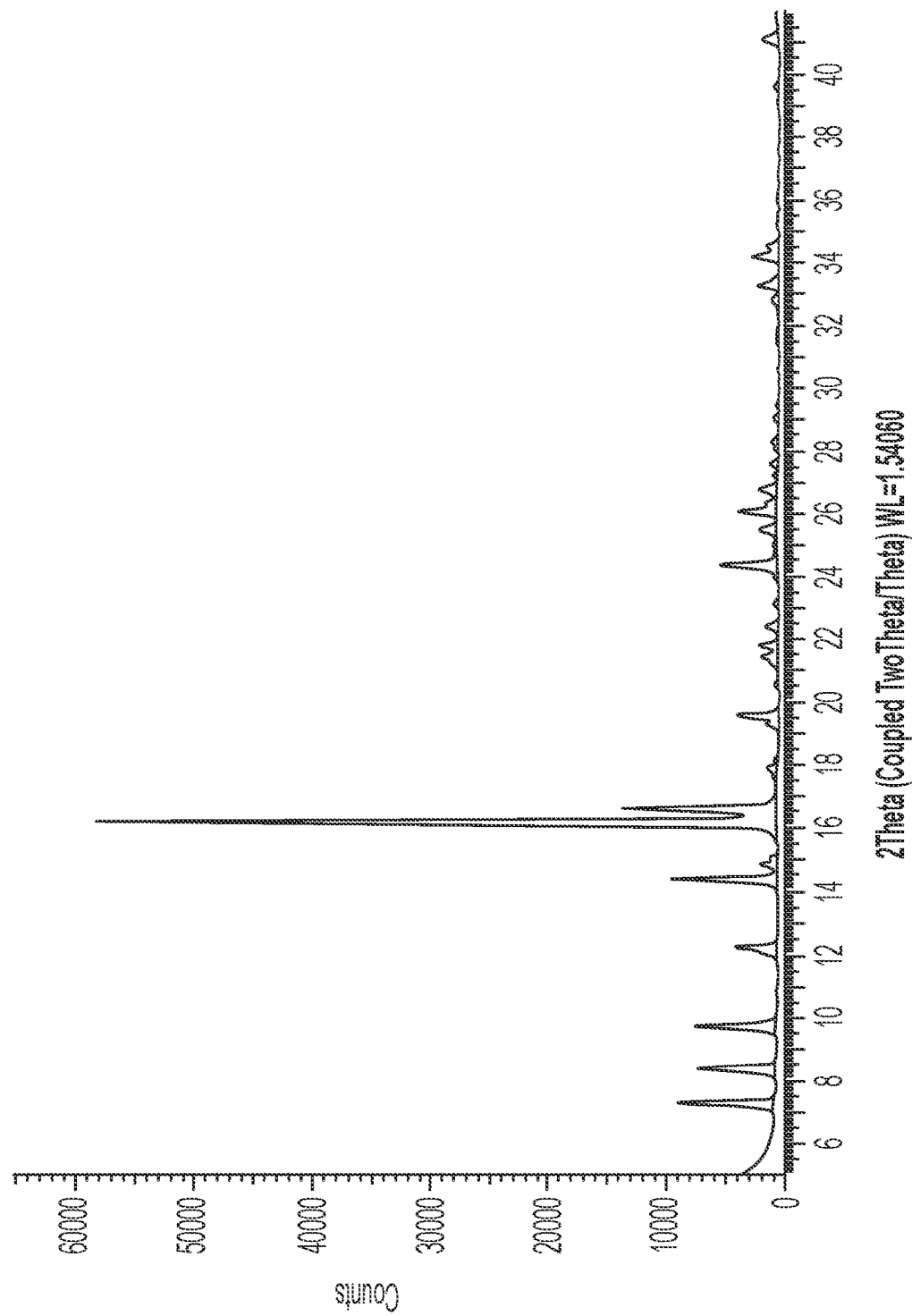
FIG. 1 depicts the XRPD Pattern for the crystalline 1:1 Tranilast N-methylglucamine form I salt.

The invention relates to crystalline tranilast salts. The crystalline tranilast salts of the invention, their preparation and their characterization are described below and shown in the figures. The invention relates to pharmaceutical compositions containing a crystalline tranilast salt of the invention and a pharmaceutically acceptable carrier. The invention also relates to methods of treatment for the diseases described above and the use of a therapeutically effective amount of a crystalline tranilast salt of the invention for that treatment.

When two solid components are successfully crystallised together to form a two-component molecular complex with a new unique solid-state crystalline structure this could result in either a salt or a cocrystal. Whether a salt or a cocrystal is formed is dependent on whether a proton transfer takes place between the two different components of the complex. If a proton is transferred from one component to the other resulting in ionic bonding then a crystalline salt results. If no proton transfer occurs and the components remain in their neutral state, held together only by hydrogen bonds, Van der Waals bonds etc, then a cocrystal is formed. Whether or not proton transfer takes place is governed by the difference in pKa values for the acidic and basic functional groups of each component. There exists a 'rule of three' that states that if the pKa (protonated base)—pKa (acid) (ΔpKa) is greater than three then a salt will be formed (P. Stahl. *Handbook of pharmaceutical salts: properties, selection and use*, International Union of Pure and Applied Chemistry, VHCA; Wiley-VCH: Weinheim, New York, 2002).

Tranilast contains a carboxylic acid group with a pKa of 3.25. Table 1 lists the pKa values for the protonated basic functional groups of the molecules used to form the crystalline tranilast compounds of the invention. It can be seen that the ΔpKa for formation of molecular complexes between each of these molecules with tranilast ranges from 5.63 to 12.45. Such large differences in pKa (ΔpKa) between each compound in the table and tranilast indicates that the new crystalline complexes of the invention are salts.

TABLE 1

| Salt Former | pKa | ΔpKa |
| --- | --- | --- |
| N-methylglucamine/N-ethylglucamine | 9.52 | 6.27 |
| Lysine | 8.95 | 5.70 |
| Diethylamine | 11.09 | 7.84 |
| Potassium Hydroxide | 15.70 | 12.45 |
| Diethanolamine | 8.88 | 5.63 |
| Ethanolamine | 9.45 | 6.20 |

Accordingly, the invention relates to a crystalline 1:1 tranilast n-methylglucamine form I salt; a crystalline 1:1 tranilast n-methylglucamine form 11 salt; a crystalline 1:1 tranilast 1-lysine salt; a crystalline 1:1 tranilast diethylamine salt; a crystalline 1:1 tranilast n-ethylglucamine salt; a crystalline 1:1 tranilast potassium monohydrate salt; a crystalline 1:1 tranilast diethanolamine salt; and a crystalline 1:1 tranilast ethanolamine salt. The crystalline tranilast salts, their preparation and their characterization are described below and shown in the figures.

Therapeutic Uses of Crystalline Tranilast Salts

The invention further relates to the therapeutic use of the crystalline tranilast salts of the invention, a crystalline 1:1 tranilast n-methylglucamine form 1 salt; a crystalline 1:1 tranilast n-methylglucamine form 11 salt; a crystalline 1:1 tranilast 1-lysine salt; a crystalline 1:1 tranilast diethylamine salt; a crystalline 1:1 tranilast n-ethylglucamine salt; a crystalline 1:1 tranilast potassium monohydrate salt; a crystalline 1:1 tranilast diethanolamine salt; and a crystalline 1:1 tranilast ethanolamine salt. Tranilast, as discussed above, is known to possess anti-allergic, anti-fibrotic, anti-inflammatory, anti-tumor, neurogenesis enhancing and angiogenesis inhibitory properties. The crystalline tranilast salts of the invention may then be used to treat diseases, disorders and conditions, such as those discussed above, that are associated with such properties. Accordingly, the invention relates to the method of treating such a disease, disorder, or condition comprising the step of administering to a patient in need thereof a therapeutically effective amount of a crystalline tranilast salt of the invention or of administering to a patient in need thereof a therapeutic composition containing a crystalline tranilast salt of the invention.

The term "treatment" or "treating" means any treatment of a disease, disorder or condition in a mammal, including: preventing or protecting against the disease, disorder or condition, that is, causing the clinical symptoms not to develop; inhibiting the disease, disorder or condition, that is, arresting or suppressing the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder or condition. The term "protection" is meant to include "prophylaxis."

Pharmaceutical Compositions Containing the Crystalline Tranilast Salts

The invention also relates to pharmaceutical compositions comprising, consisting essentially or consisting of a therapeutically effective amount of a crystalline tranilast salt according to the invention and a pharmaceutically acceptable carrier (also known as a pharmaceutically acceptable excipient). As mentioned above, these pharmaceutical compositions are therapeutically useful to treat or prevent disorders such as those discussed above. A pharmaceutical composition of the invention may be a solid dosage form or a solution made with a crystalline tranilast salt of the invention.

A pharmaceutical composition of the invention may be in any pharmaceutical form which contains a crystalline tranilast salt according to the invention. The pharmaceutical composition may be, for example, a tablet, a capsule, an oral solution, an injectable composition, a topical composition, an inhalable composition or a transdermal composition.

Liquid pharmaceutical compositions may be prepared using a tranilast salt of the invention and represent a particular embodiment of the invention. For a liquid pharmaceutical composition, the tranilast salt may be dissolved in a solvent, e.g. water, at the time and point of care. The pharmaceutical compositions generally contain, for example, about 0.1% to about 99.9% by weight of a crystalline tranilast salt of the invention, for example, about 0.5% to about 99% by weight of a crystalline tranilast salt of the invention and, for example, 99.5% to 0.5% by weight of at least one suitable pharmaceutical excipient or solvent. In one embodiment, the composition may be between about 5% and about 75% by weight of a crystalline tranilast salt of the invention with the rest being at least one suitable pharmaceutical excipient, solvent or at least one other adjuvant, as discussed below.

A "therapeutically effective amount of a crystalline tranilast salt according to the invention" is that which correlates to the therapeutic effect currently achieved when administering orally about 50 mg—about 900 mg, about 50 mg—about 200 mg, about 100 mg—about 800 mg, about 250 mg—about 750 mg, about 300 mg—about 700 mg, about 550 mg—about 650 mg, about 100 mg or about 600 mg of tranilast itself. As discussed above, tranilast is marketed in Japan and South Korea by Kissei Pharmaceutical Co. Ltd under the Rizaben® brand name. Tranilast is prescribed orally to treat bronchial asthma, allergic rhinitis, atopic dermatitis, keloid or hypertrophic scar. The typical dosage in adults for these conditions is currently one 100 mg tablet three times per day. However, it was shown that a dose of at least 600 mg per day was required to treat a proliferative disease such as restenosis (H. Tamai, *Am Heart J.*1999; 138(5): 968-75) and a Phase III clinical study of tranilast for the prevention of restenosis included doses as high as 900 mg per day (D Holmes, *Circulation.* 2002; 106(10): 1243-1250).

A therapeutically effective amount of a crystalline tranilast salt of the invention in a solid dosage form or when administered as an inhaled solid may be in the range mentioned above but may also range from about 0.1 mg to about 250 mg, 0.5 mg to about 150 mg, and even from about 1 mg to about 100 mg of the crystalline tranilast salt itself.

To overcome the photochemical instability of tranilast stored in solution (N Hori, *Chem. Pharm. Bull.* 1999; 47(12): 1713-1716) and also the disadvantage of long term storage of bulkier solution-based formulations, the pharmaceutical composition of the crystalline tranilast salts may advantageously be a solid composition that can be dissolved in-situ at the time of use to give a solution for immediate delivery to a patient as a liquid dosage form. Again advantageously, the liquid dosage form can then be used to administer any of the doses described above or other high doses, for example, 600 mg, 750 mg, 900 mg or higher, per unit dose. Such dosage forms could be suitable for use as, for example, injectable, inhaled or oral solution dosage forms.

A therapeutically effective amount of a pharmaceutical solution of a crystalline tranilast salt according to the invention may also be in the range mentioned above although for delivery methods, such as injectable or inhaled delivery, that avoid first pass metabolism it can be understood that efficacy may also be achieved at a lower dose. The therapeutically effective amount of a drug can depend upon the route of administration as is known in the art. For example, in a topical application such as with a cream, eye drops, or in pulmonary delivery the therapeutically effective amount may be small, e.g., from about 0.1 mg to about 250 mg, 0.5 mg to about 150 mg, and even from about 1 mg to about 100 mg of the crystalline tranilast salt itself.

The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion of tranilast; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, that is one containing a crystalline tranilast salt of the invention, a carrier should be chosen that maintains the crystalline form. In other words, the carrier should not substantially alter the crystalline tranilast salt. Nor should the carrier be otherwise incompatible with the crystalline tranilast salt used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, a crystalline tranilast salt of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing a crystalline tranilast salt of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the active crystalline tranilast salts of the invention topically to the lung. One such means could involve a dry powder inhaler formulation of respirable particles comprised of the crystalline tranilast salts of the invention, which the patient being treated inhales. It is common for a dry powder formulation to include carrier particles, to which the crystalline tranilast salt particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose. The crystalline tranilast salt would be dispersed into the respiratory tract, and subsequently contact the lower lung in a pharmaceutically effective amount.

Another means of administering the active compounds topically to the eyes of the subject would involve administering a topical liquid/liquid suspension in the form of eye drops or eye wash. Liquid pharmaceutical compositions of the active compound for producing an eye drop or eye wash formulation can be prepared by combining the active compound with a suitable vehicle, such as sterile pyrogen free water or sterile saline by techniques known to those skilled in the art.

In addition to the topical method of administration described above, there are various methods of administering the active crystalline tranilast salts of the invention systemically by such methods. One such means would involve an aerosol suspension of respirable particles comprised of the crystalline tranilast salts of the invention, which the patient being treated inhales. The crystalline tranilast salt would be absorbed into the bloodstream via the lungs in a pharmaceutically effective amount. The respirable particles can be liquid or solid, with a particle size sufficiently small to pass through the mouth and larynx upon inhalation.

Because the crystalline form of a crystalline tranilast salt may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically acceptable excipient (also known as a pharmaceutically acceptable carrier).

A crystalline tranilast salt according to the invention may also be used to formulate liquid or injectable pharmaceutical compositions. Administration of a crystalline tranilast salt in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, or subcutaneous), topically, transdermally, intravaginally, intravesically, intrasystemically, ophthalmically or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

For conditions such as fibrosis and cancer, where the patient may be unable to swallow solid oral dosage forms, the composition of the crystalline tranilast salts may be in a liquid form, such as for example an injectable or a liquid oral formulation that can be administered by a healthcare specialist.

The invention also relates to a method of preparing a liquid pharmaceutical composition comprising the step of dissolving a crystalline tranilast salt according to the invention in a pharmaceutically acceptable solvent and to liquid pharmaceutical compositions prepared according to that method. Physiologically acceptable aqueous vehicles may be used as the solvent to prepare a liquid formulation of a crystalline tranilast salt of the invention. Water or pharmaceutically-acceptable isotonic aqueous solution is preferred. The aqueous vehicle should allow the tranilast salt to dissolve and remain in solution. Saline should be avoided as the sodium present in saline may precipitate some, or all, of the tranilast from the solution. As discussed above, liquid pharmaceutical compositions of the invention may be administered orally, parenterally (including by inhalation), and intravenously.

EXAMPLES

The following analytical methods were used to characterize the tranilast salts of the invention:

X-Ray Powder Diffraction Characterisation: X-ray powder diffraction patterns for the samples were acquired on a Bruker D8 diffractometer using CuKα radiation (40 kV, 40 mA), θ-2θ goniometer, V4 receiving slits, a Ge monochromator and a Lynxeye detector. The instrument is performance checked using a certified Corundum standard (NIST 1976). The data were collected over an angular range of 2° to 42° 2θ using a step size of 0.05° 2θ and a step time of 0.5 seconds. Samples run under ambient conditions were prepared as flat plate specimens using powder as received without grinding. Approximately, 35 mg of the sample was gently packed into a cavity cut into polished, zero background (510) silicon wafer. All samples were analysed using Diffrac Plus EVA v11.0.0.2 or v13.0.0.2.

Single Crystal X-Ray Diffraction (SCXRD): Data were collected on an Oxford Diffraction SuperNova Dual source, Cu at zero, Atlas CCD Diffractometer equipped with an Oxford Cryosystems Cryostream cooling device. Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning calorimetry (DSC): DSC data were collected on a PerkinElmer Pyris 4000 DSC. The instrument was verified for energy and temperature calibration using certified indium. A predefined amount of the sample, 0.5-3.0 mg, was placed in a pin holed aluminium pan and heated at 20° C. min$^{-1}$ from 30 to 350° C. The instrument control, data acquisition and analysis were performed with Pyris Software v9.0.1.0203.

Thermo-Gravimetric Analysis (TGA): TGA data were collected on a PerkinElmer Pyris 1 TGA equipped with a 20 position auto-sampler. The instrument was calibrated using a certified weight and certified Alumel and Perkalloy for temperature. A predefined amount of the sample, 1-5 mg, was loaded onto a pre-tared aluminium crucible and was heated at 20° C. min$^{-1}$ from ambient temperature to 400° C. A nitrogen purge at 20 ml.min$^{-1}$ was maintained over the sample. The instrument control, data acquisition and analysis were performed with Pyris Software v9.0.1.0203.

Example 1

Crystalline 1:1 Tranilast N-methylglucamine Form I Salt 1.1 Preparation of the Crystalline 1:1 Tranilast N-methylglucamine Form I Salt The batch of crystalline 1:1 tranilast N-methylglucamine Form I used for characterisation was prepared as follows:

Tranilast (1.00 g) and N-methylglucamine (596 mg) were weighed into a round bottom flask. Ethanol (30 ml) was added flask. The resulting yellow slurry was heated gradually to 70° C. and then maintained at this temperature for 1 hour. The resulting white slurry was allowed to gradually cool and then stirred at room temperature for 15 hours. The flask was placed in a refrigerator for 3 hours and the product was then filtered under vacuum. The resulting colourless crystals were dried in a vacuum oven at 40° C. overnight.

1.2 XRPD Characterisation of the Crystalline 1:1 Tranilast N-methylglucamine Form I Salt The experimental XRPD pattern of the crystalline 1:1 tranilast N-methylglucamine Form I salt is shown in FIG. 1. Table 2 lists the angles, °2θ±0.2°2θ, and d value of the peaks identified in the experimental XRPD pattern of FIG. 1. The entire list of peaks or corresponding d values, or a subset thereof, may be sufficient to characterize the crystalline salt, as well as by an XRPD pattern substantially similar to FIG. 1. For example, the crystalline 1:1 tranilast N-methylglucamine Form I salt may be characterized by at least four peaks selected from the peaks at 7.3, 8.4, 9.7, 12.2, 14.4 and 16.2°2θ±0.2°2θ or their corresponding d values.

TABLE 2

| Angle °2θ ± 0.2 °2θ | d value Angstrom | Intensity % |
|---|---|---|
| 7.3 | 12.10 | 14.5% |
| 8.4 | 10.53 | 11.5% |
| 9.7 | 9.08 | 12.1% |
| 12.2 | 7.22 | 6.3% |
| 14.4 | 6.15 | 15.6% |
| 14.9 | 5.95 | 2.7% |
| 16.2 | 5.46 | 100.0% |
| 16.7 | 5.31 | 22.7% |
| 17.9 | 4.95 | 1.2% |
| 19.3 | 4.59 | 1.7% |
| 19.6 | 4.52 | 6.0% |
| 21.5 | 4.13 | 2.2% |
| 21.8 | 4.07 | 2.7% |
| 22.4 | 3.96 | 1.9% |
| 24.4 | 3.65 | 8.4% |
| 25.5 | 3.49 | 2.4% |
| 26.1 | 3.41 | 5.5% |
| 26.3 | 3.38 | 1.6% |
| 26.8 | 3.32 | 2.5% |
| 27.6 | 3.23 | 1.2% |
| 28.3 | 3.15 | 1.0% |
| 33.3 | 2.69 | 2.9% |
| 34.2 | 2.62 | 3.9% |
| 34.5 | 2.60 | 1.9% |
| 41.1 | 2.20 | 2.3% |

1.3 DSC of the Crystalline 1:1 Tranilast N-methylglucamine Form I Salt

Figure 2:
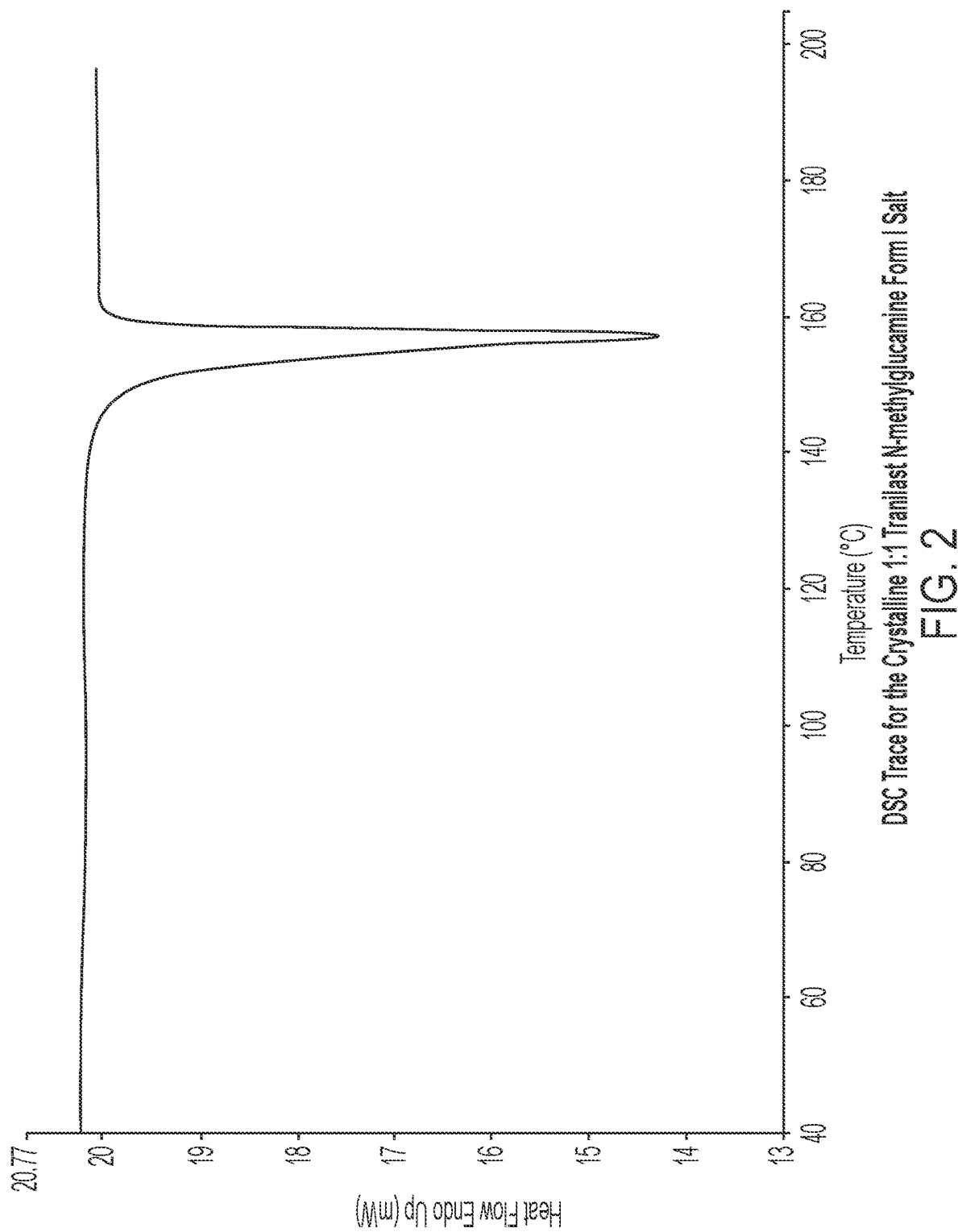
FIG. 2 depicts the DSC Trace for the crystalline 1:1 Tranilast N-methylglucamine form I salt.

The differential scanning calorimetry (DSC) trace, FIG. 2, shows a single endotherm with a peak maximum of 157.2° C.

1.4 TGA of the Crystalline 1:1 Tranilast N-methylglucamine Form I Salt

Figure 3:
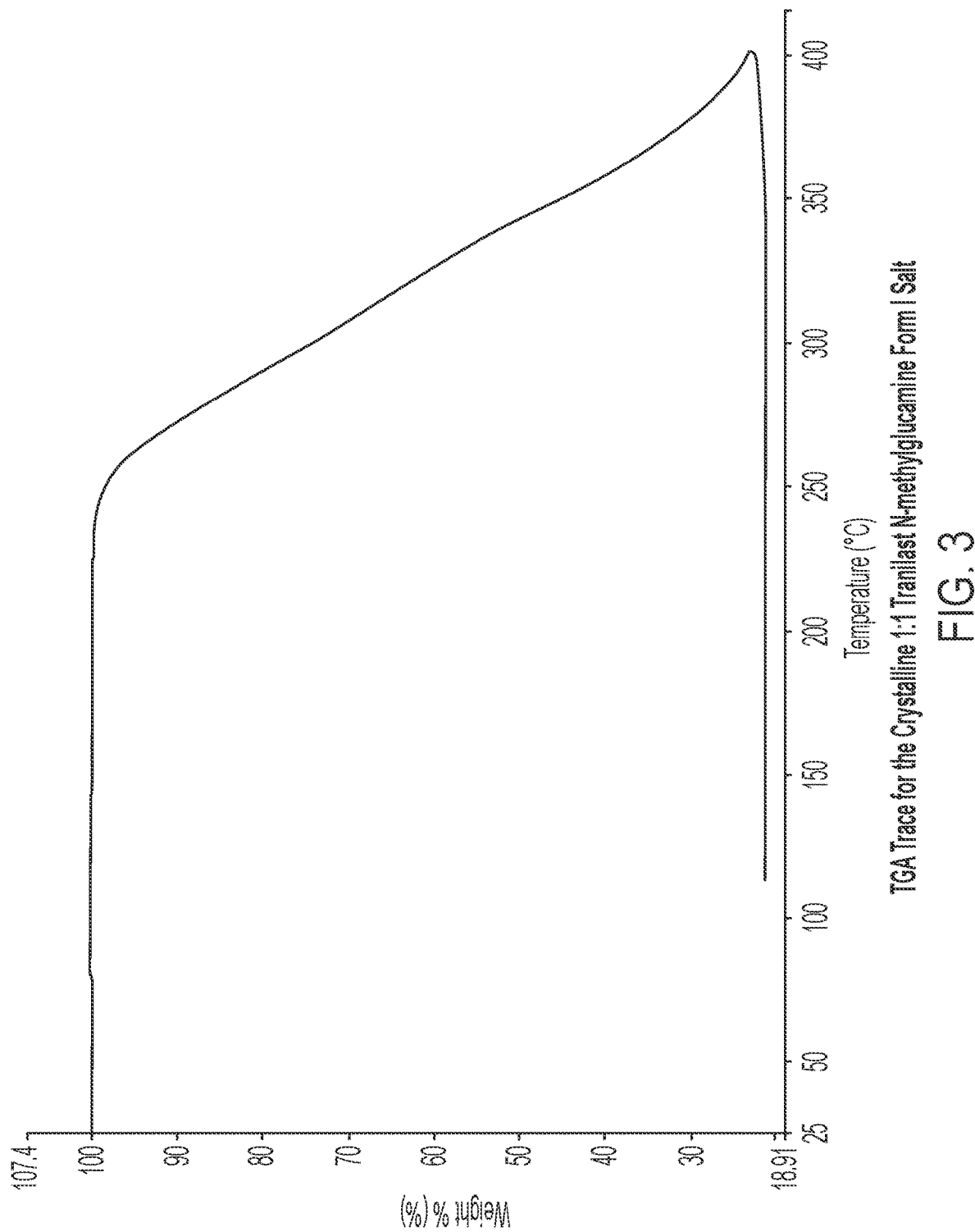
FIG. 3 depicts the TGA Trace for the crystalline 1:1 Tranilast N-methylglucamine form I salt.

The thermal gravimetric analysis (TGA) trace, FIG. 3, shows no significant weight loss prior to 250° C.

Figure 4:
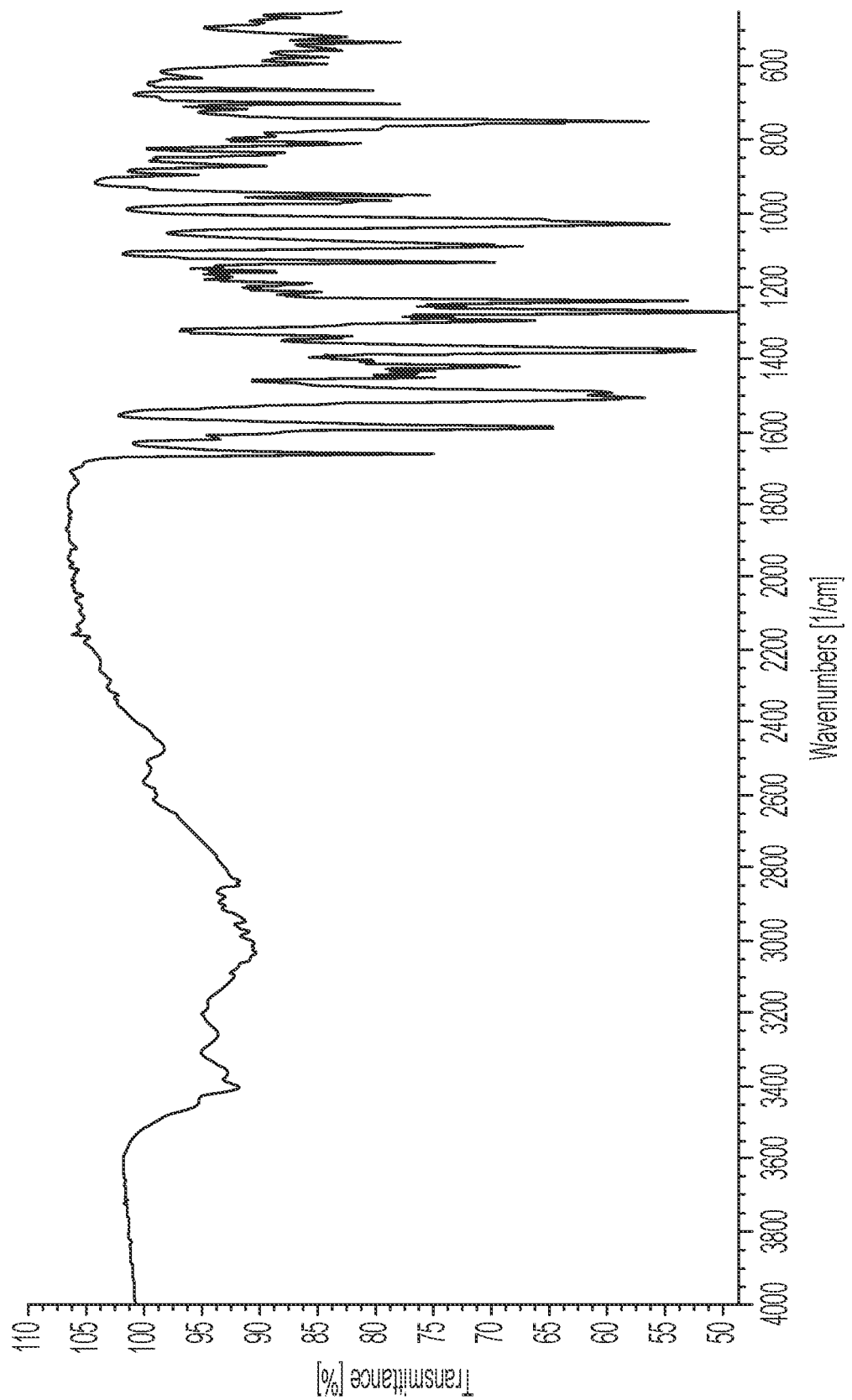
FIG. 4 depicts the Infrared Spectrum for the crystalline 1:1 Tranilast N-methylglucamine form I salt.

1.5 Infrared Spectrum of the Crystalline 1:1 Tranilast N-methylglucamine Form I Salt The experimental Infrared Spectrum of the crystalline 1:1 tranilast N-methylglucamine Form I salt is shown in FIG. 4. The significant peaks identified in the experimental infrared spectrum of FIG. 4 are 3402, 1662, 1589, 1507, 1451, 1423, 1378, 1341, 1296, 1272, 1244, 1217, 1134, 1091, 1029, 965, 948, 809, 749, 700, 662, 590, 571, 551, 532 and 517 cm$^{-1}$±1 cm$^{-1}$. The entire list of peaks, or a subset thereof, may be sufficient to characterize the crystalline salt, as well as by an infrared pattern substantially similar to FIG. 4. For example, the crystalline 1:1 tranilast N-methylglucamine Form I salt may be characterized by at least four peaks selected from the peaks at 1662, 1589, 1507, 1423, 1378, 1272 and 1244 cm$^{-1}$±1 cm$^{-1}$.

Figure 5:
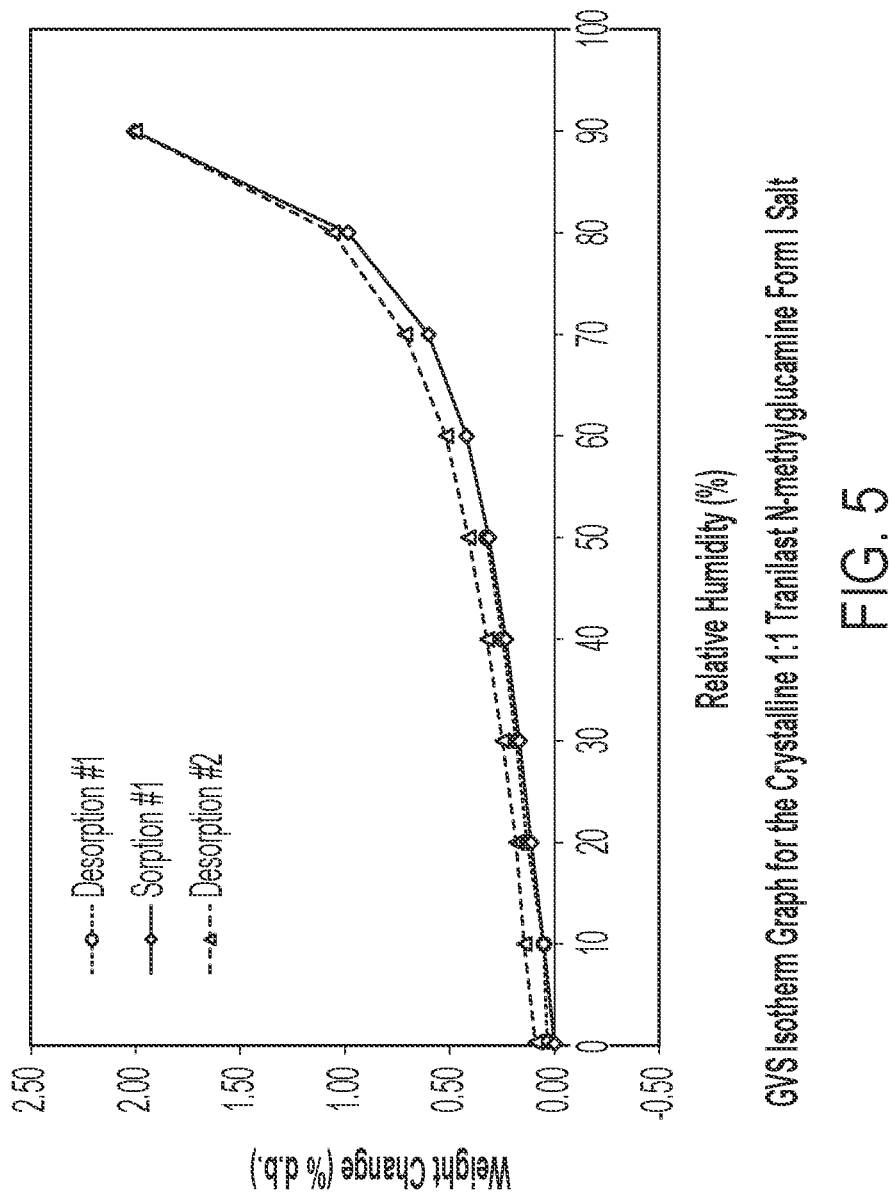
FIG. 5 depicts the GVS Isotherm Graph for the crystalline 1:1 Tranilast N-methylglucamine form I salt.

1.6 Gravimetric Vapour Sorption (GVS) Analysis of the Crystalline 1:1 Tranilast N-methylglucamine Form I Salt The moisture sorption isotherm graph obtained for the crystalline 1:1 tranilast N-methylglucamine Form I salt is shown in FIG. 5. The crystalline 1:1 tranilast N-methylglucamine Form I salt was found to reversibly absorb 1.4% w/w across the 90% humidity range at 25° C. XRPD analysis of the sample at 0% RH and 90% RH confirmed that the sample remained as the crystalline 1:1 tranilast N-methylglucamine Form I salt across the entire humidity range and did not demonstrate any form conversion under these conditions.

Example 2: Crystalline 1:1 Tranilast N-methylglucamine Form II Salt 2.1 Preparation of the Crystalline 1:1 Tranilast N-methylglucamine Form II Salt The batch of crystalline 1:1 tranilast N-methylglucamine Form II salt used for characterisation was prepared as follows:

Tranilast (3.00 g) and N-methylglucamine (1.79 g) were weighed into a round bottom flask. Butan-1-ol (30 ml) was added to the flask. The resulting yellow slurry was stirred at room temperature for 12 hours. The product was then filtered under vacuum and the resulting colourless crystals were dried in a vacuum oven at 40° C. overnight.

Figure 6:
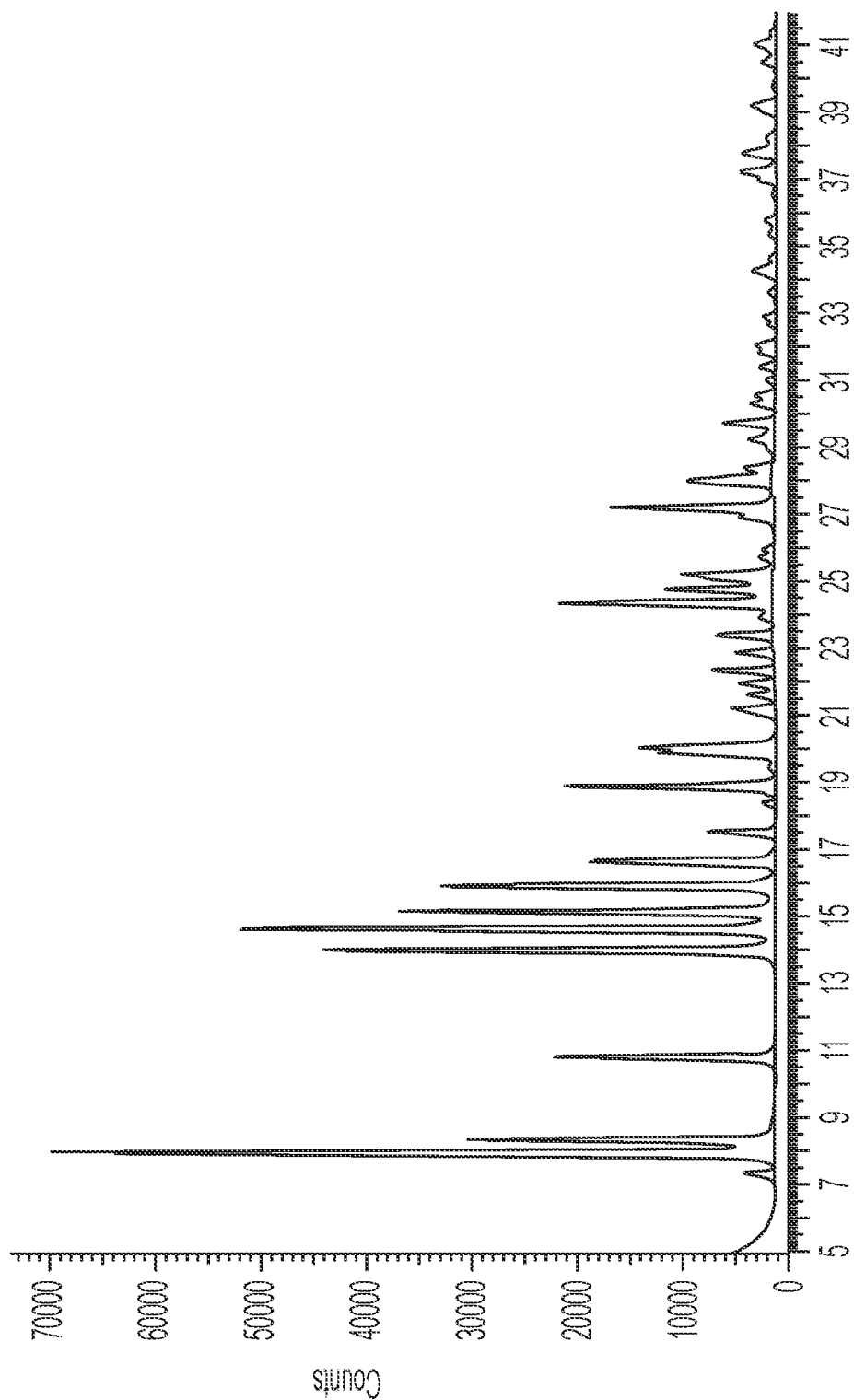
FIG. 6 depicts the XRPD Pattern for the crystalline 1:1 Tranilast N-methylglucamine form II salt.

2.2 XRPD Characterisation of the Crystalline 1:1 Tranilast N-methylglucamine Form II Salt The experimental XRPD pattern of the crystalline 1:1 tranilast N-methylglucamine Form II salt is shown in FIG. 6. Table 3 lists the angles, °2θ±0.2°2θ, and d value of the peaks identified in the experimental XRPD pattern of FIG. 6. The entire list of peaks or corresponding d values, or a subset thereof, may be sufficient to characterize the crystalline salt, as well as by an XRPD pattern substantially similar to FIG. 6. For example, the crystalline 1:1 tranilast N-methylglucamine Form II salt may be characterized by at least four peaks selected from the peaks at 10.8, 14.0, 14.6, 15.2, 15.9, 16.7, and 18.9°2θ±0.2°2θ or their corresponding d values.

TABLE 3

| Angle °2θ ± 0.2 °2θ | d value Angstrom | Intensity % |
|---|---|---|
| 7.3 | 12.03 | 4.1% |
| 8.0 | 11.08 | 100.0% |
| 8.3 | 10.59 | 42.3% |
| 10.8 | 8.18 | 30.4% |
| 14.0 | 6.32 | 62.1% |
| 14.6 | 6.05 | 74.2% |
| 15.2 | 5.84 | 51.8% |
| 15.9 | 5.56 | 45.9% |
| 16.7 | 5.32 | 25.4% |

TABLE 3-continued

| Angle °2θ ± 0.2 °2θ | d value Angstrom | Intensity % |
|---|---|---|
| 17.5 | 5.06 | 9.2% |
| 18.9 | 4.69 | 29.1% |
| 19.9 | 4.46 | 16.1% |
| 20.1 | 4.42 | 18.9% |
| 21.2 | 4.18 | 6.1% |
| 21.2 | 4.18 | 6.1% |
| 21.6 | 4.10 | 3.6% |
| 22.0 | 4.04 | 4.8% |
| 22.4 | 3.97 | 8.3% |
| 22.9 | 3.88 | 5.2% |
| 23.4 | 3.80 | 7.9% |
| 24.4 | 3.65 | 29.3% |
| 24.8 | 3.59 | 15.0% |
| 25.1 | 3.54 | 9.5% |
| 25.2 | 3.53 | 12.9% |
| 27.0 | 3.31 | 4.7% |
| 27.2 | 3.27 | 22.7% |
| 28.0 | 3.18 | 11.7% |
| 28.4 | 3.14 | 4.0% |
| 29.3 | 3.05 | 3.4% |
| 29.7 | 3.00 | 6.9% |
| 30.3 | 2.94 | 3.2% |
| 32.1 | 2.79 | 2.9% |
| 32.7 | 2.74 | 1.1% |
| 32.9 | 2.72 | 1.7% |
| 34.3 | 2.61 | 3.4% |
| 37.3 | 2.41 | 4.9% |
| 37.8 | 2.38 | 4.6% |

2.3 DSC of the Crystalline 1:1 Tranilast N-methylglucamine Form II Salt

Figure 7:
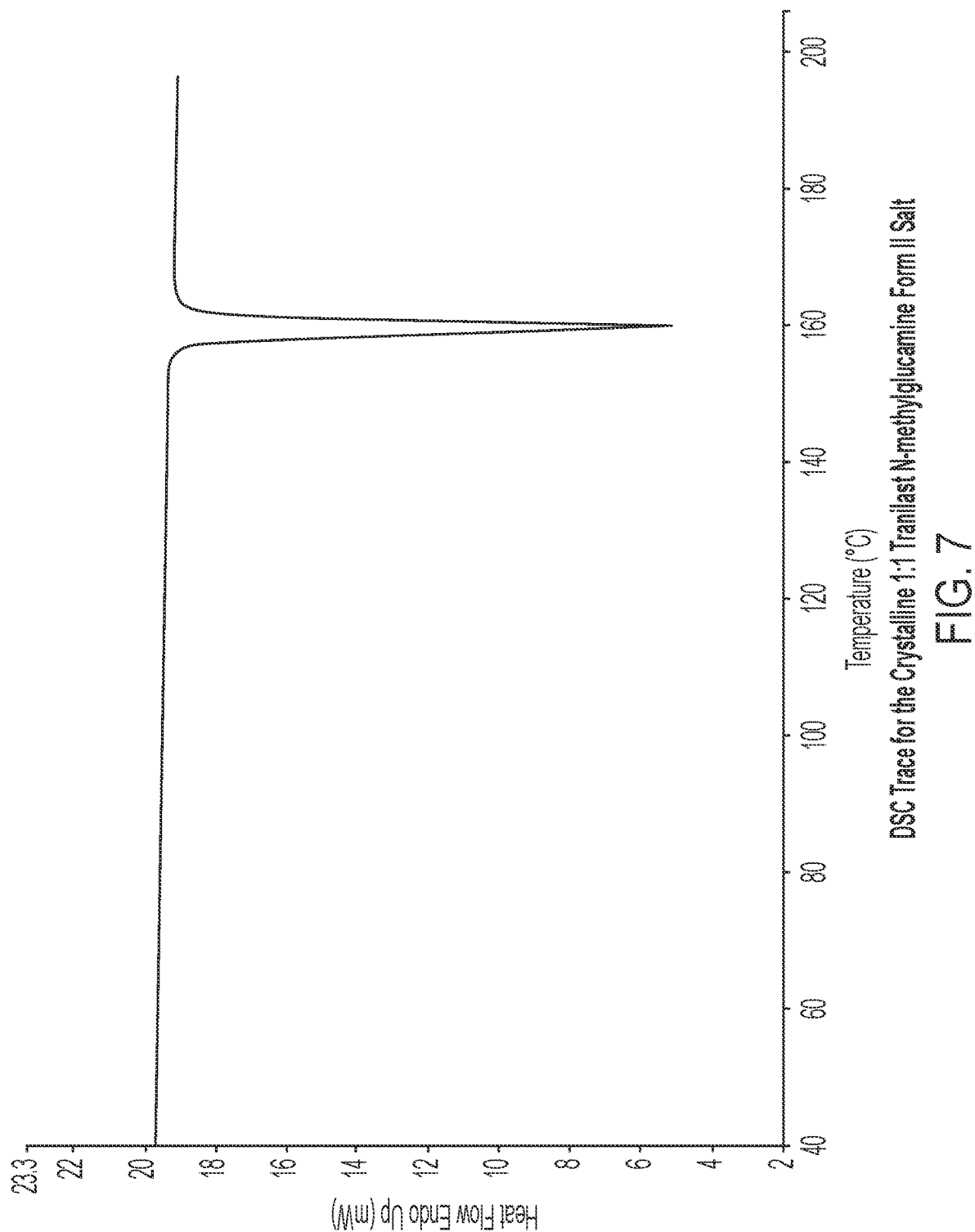
FIG. 7 depicts the DSC Trace for the crystalline 1:1 Tranilast N-methylglucamine form II salt.

The differential scanning calorimetry (DSC) trace, FIG. 7, shows a single endotherm with a peak maximum of 160.1° C.

2.4 TGA of the Crystalline 1:1 Tranilast N-methylglucamine Form II Salt

Figure 8:
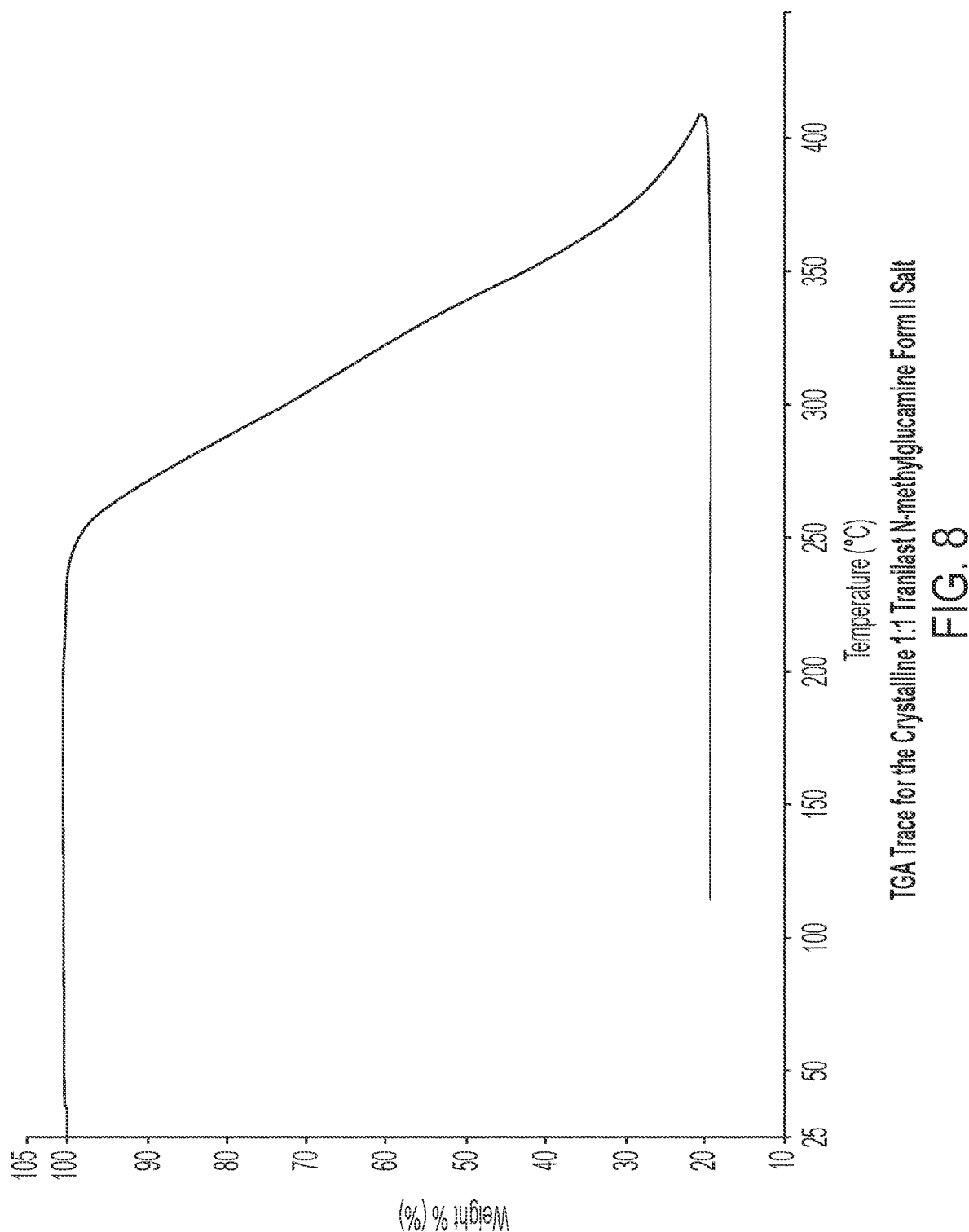
FIG. 8 depicts the TGA Trace for the crystalline 1:1 Tranilast N-methylglucamine form II salt.

The thermal gravimetric analysis (TGA) trace, FIG. 8, shows no significant weight loss prior to 250° C.

Figure 9:
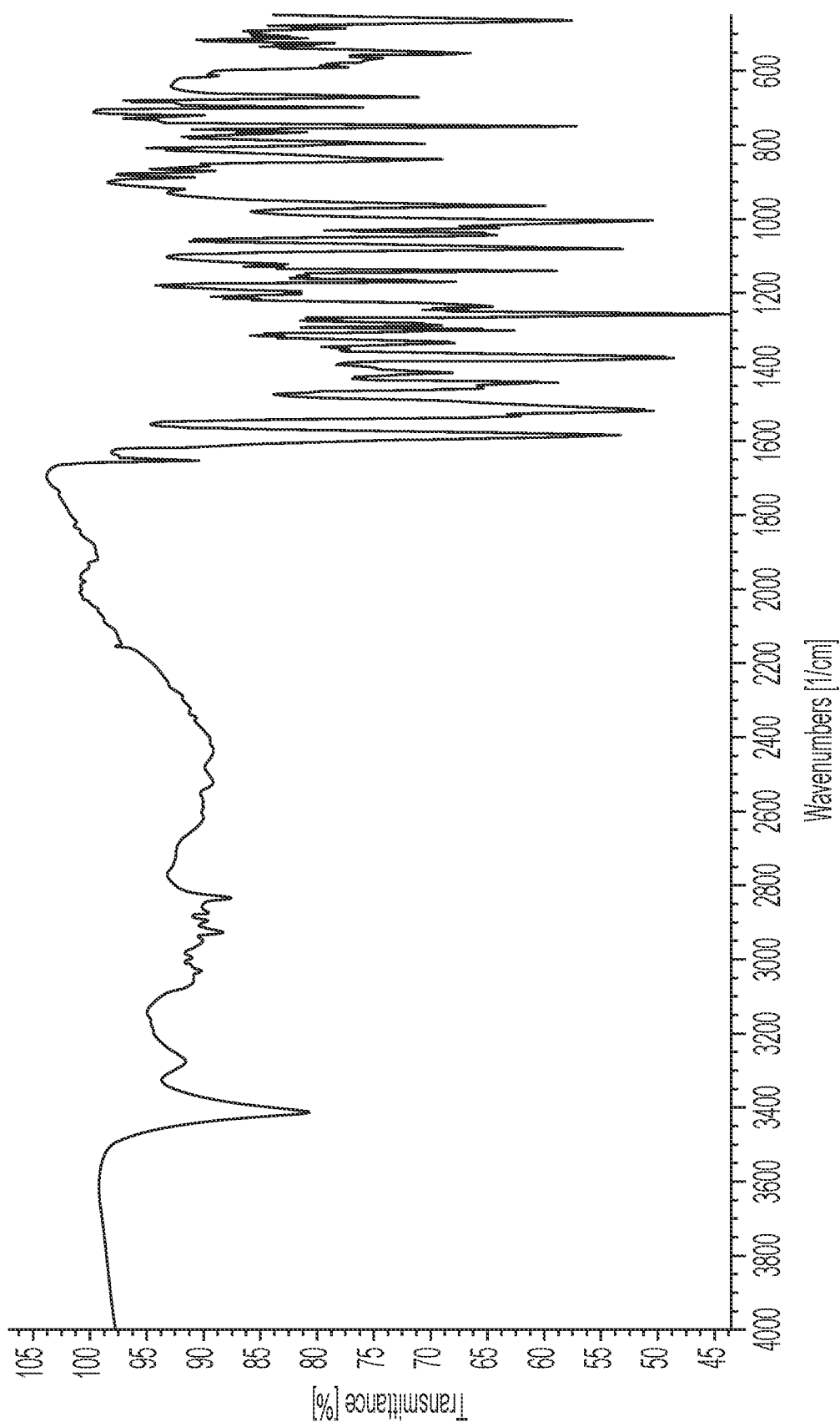
FIG. 9 depicts the Infrared Spectrum for the crystalline 1:1 Tranilast N-methylglucamine form II salt.

2.5 Infrared Spectrum of the Crystalline 1:1 Tranilast N-methylglucamine Form II Salt The experimental Infrared Spectrum of the crystalline 1:1 tranilast N-methylglucamine Form II salt is shown in FIG. 9. The significant peaks identified in the experimental infrared spectrum of FIG. 9 are 3419, 1655, 1585, 1519, 1443, 1417, 1377, 1335, 1301, 1287, 1258, 1235, 1169, 1142, 1079, 1044, 1007, 965, 842, 795, 745, 699, 670, 590, 566, 550, 526, 484 and 463 cm$^{-1}$±1 cm$^{-1}$. The entire list of peaks, or a subset thereof, may be sufficient to characterize the crystalline salt, as well as by an infrared pattern substantially similar to FIG. 9. For example, the crystalline 1:1 tranilast N-methylglucamine Form II salt may be characterized by at least four peaks selected from the peaks at 1655, 1585, 1519, 1417, 1377, 1301 and 1258 cm$^{-1}$±1 cm$^{-1}$.

Figure 10:
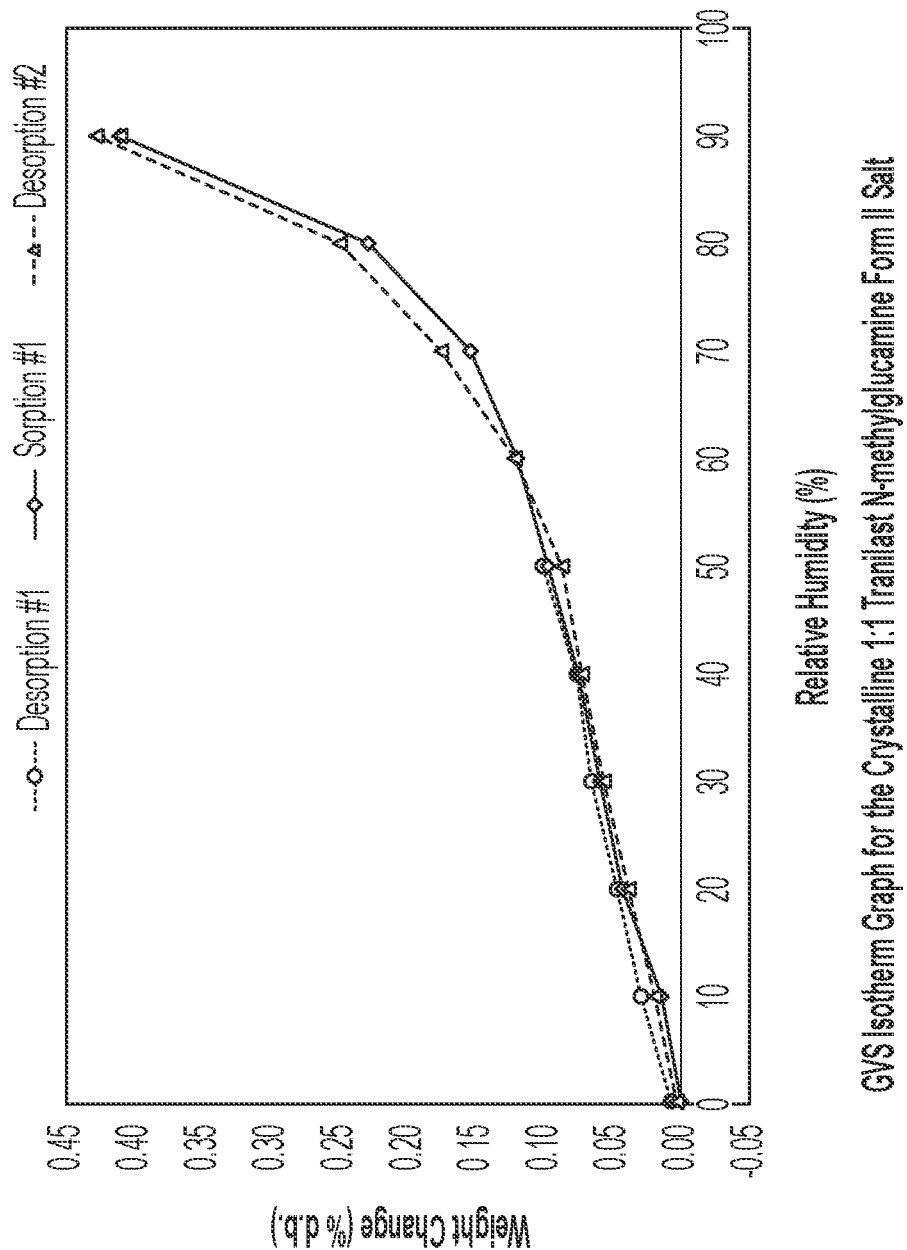
FIG. 10 depicts the GVS Isotherm Graph for the crystalline 1:1 Tranilast N-methylglucamine form II salt.

2.6 Gravimetric Vapour Sorption (GVS) Analysis of the Crystalline 1:1 Tranilast N-methylglucamine Form II Salt The moisture sorption isotherm graph obtained for the crystalline 1:1 tranilast N-methylglucamine Form II salt is shown in FIG. 10. The crystalline 1:1 tranilast N-methylglucamine form II salt was found to reversibly absorb 0.42% w/w across the 90% humidity range at 25° C. XRPD analysis of the sample at 0% RH and 90% RH confirmed that the sample remained as the crystalline 1:1 tranilast N-methylglucamine form II salt across the entire humidity range and did not demonstrate any form conversion under these conditions.

Example 3

Solid-State Stability of the Polymorphs of 1:1 Tranilast N-methylglucamine Salt

A study was carried out to examine the physical stability of the crystalline 1:1 tranilast N-methylglucamine salt polymorphs with respect to solid form conversion over time under accelerated conditions. Forms I and II of 1:1 tranilast N-methylglucamine salt (50 mg) were separately placed in a sealed container at 40° C. and 75% relative humidity and stored under these conditions for 7 days. After this time each sample was analysed by XRPD to observe any potential form changes. XRPD analysis showed that both samples retained their original crystalline form and that no solid form conversion had occurred under these conditions.

A second study was carried out to explore the solid-state stability of the crystalline 1:1 tranilast N-methylglucamine salt polymorphs under high humidity. Forms I and II of 1:1 tranilast N-methylglucamine salt (50 mg) were separately placed in a sealed container at 25° C. and 100% relative humidity and stored under these conditions for 7 days. After this time each sample was analysed by XRPD to observe any potential form changes. XRPD analysis showed that both samples retained their original crystalline form and that no solid form conversion had occurred under these conditions.

A third study was carried out to explore the solid-state stability of the crystalline 1:1 tranilast N-methylglucamine salt polymorphs under high storage temperatures. Forms I and II of 1:1 tranilast N-methylglucamine salt (50 mg) were stored in an oven at 90° C. for 7 days. After this time each sample was analysed by XRPD to observe any potential form changes. XRPD analysis showed that both samples retained their original crystalline form and that no solid form conversion had occurred under these conditions.

These studies indicate that both forms I and II of the crystalline 1:1 tranilast N-methylglucamine salt are stable crystalline forms under varying temperature and relative humidity. No interconversion of polymorphs occurs.

Example 4

Crystalline 1:1 Tranilast L-Lysine Salt 4.1 Preparation of Crystalline 1:1 Tranilast L-Lysine Salt The batch of crystalline 1:1 tranilast L-lysine salt used for characterisation was prepared as follows:

Tranilast (100 mg) and L-lysine (44.6 mg) were weighed into a glass vial. Methanol (1.5 ml) was added to the vial. The resulting yellow slurry was placed in a shaker and shaken at ambient temperatures for approximately 24 hours. The product was then filtered under vacuum and the resulting colourless crystals were dried in a vacuum oven at 40° C. overnight.

4.2 XRPD Characterisation of the Crystalline 1:1 Tranilast L-Lysine Salt

Figure 11:
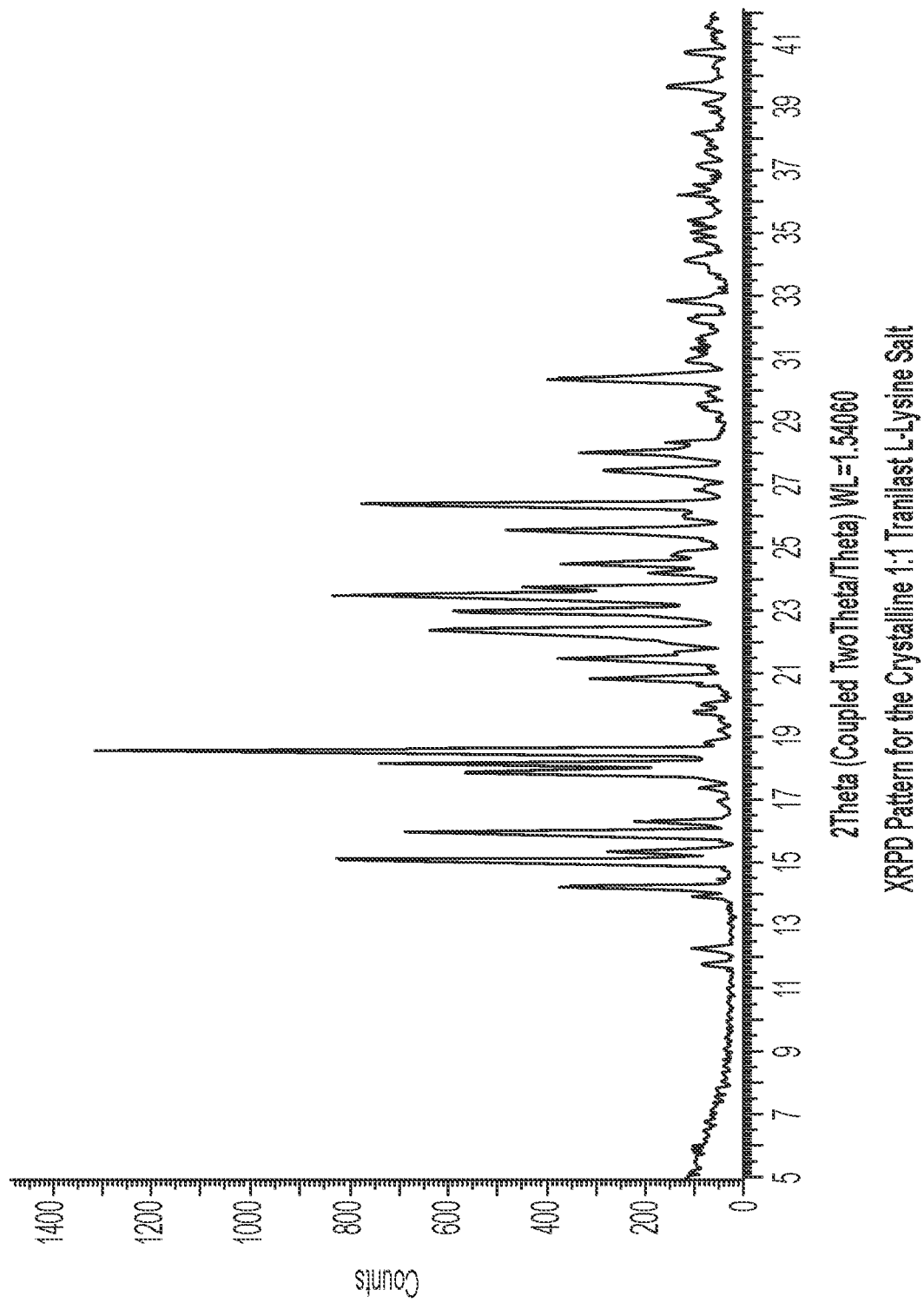
FIG. 11 depicts the XRPD Pattern for the crystalline 1:1 Tranilast L-Lysine salt.

The experimental XRPD pattern of the crystalline 1:1 tranilast L-lysine salt is shown in FIG. 11. Table 4 lists the angles, °2θ±0.2°2θ, and d value of the peaks identified in the experimental XRPD pattern of FIG. 11. The entire list of peaks or corresponding d values, or a subset thereof, may be sufficient to characterize the crystalline salt, as well as by an XRPD pattern substantially similar to FIG. 11. For example, the crystalline 1:1 tranilast L-lysine salt may be characterized by at least four peaks selected from the peaks at 11.8, 12.3, 15.1, 16.0, 18.5, 20.9 and 21.5°2θ±0.2°2θ or their corresponding d values.

TABLE 4

| Angle °2θ ± 0.2 °2θ | d value Angstrom | Intensity % |
| --- | --- | --- |
| 11.8 | 7.51 | 4.5% |
| 12.3 | 7.21 | 5.9% |
| 14.0 | 6.34 | 4.5% |
| 14.2 | 6.22 | 27.6% |
| 15.1 | 5.86 | 62.4% |
| 15.4 | 5.76 | 18.4% |
| 16.0 | 5.55 | 50.6% |
| 16.3 | 5.43 | 13.7% |
| 17.9 | 4.96 | 42.2% |
| 18.2 | 4.88 | 53.3% |
| 18.5 | 4.78 | 100.0% |
| 19.8 | 4.48 | 5.0% |
| 20.9 | 4.25 | 20.8% |
| 21.5 | 4.13 | 24.5% |
| 22.4 | 3.97 | 46.4% |
| 23.0 | 3.86 | 41.4% |
| 23.5 | 3.78 | 60.7% |
| 23.7 | 3.75 | 29.1% |
| 24.2 | 3.67 | 9.7% |
| 24.5 | 3.63 | 23.7% |
| 24.8 | 3.58 | 5.4% |
| 25.6 | 3.48 | 34.0% |
| 26.1 | 3.42 | 5.0% |
| 26.4 | 3.37 | 54.8% |
| 27.4 | 3.25 | 16.7% |
| 28.0 | 3.18 | 22.6% |
| 28.3 | 3.15 | 5.1% |
| 30.4 | 2.94 | 27.2% |
| 31.0 | 2.89 | 4.9% |
| 32.3 | 2.77 | 4.8% |
| 32.9 | 2.72 | 8.6% |
| 34.2 | 2.62 | 5.4% |

4.3 DSC of the Crystalline 1:1 Tranilast L-Lysine Salt

Figure 12:
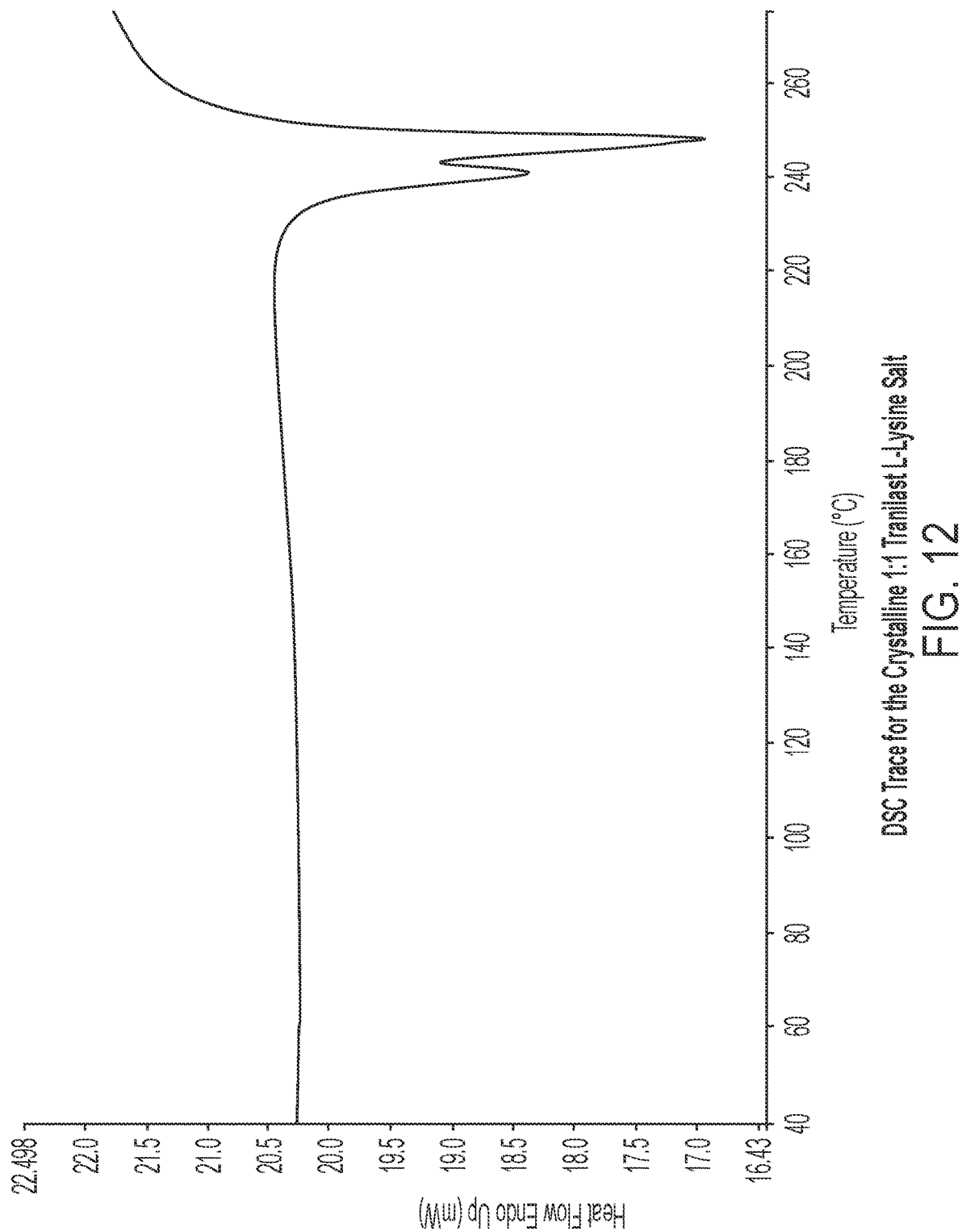
FIG. 12 depicts the DSC Trace for the crystalline 1:1 Tranilast L-Lysine salt.

The differential scanning calorimetry (DSC) trace, FIG. 12, shows a double endotherm with peak maximums at 241.1 and 248.0° C.

4.4 TGA of the Crystalline 1:1 Tranilast L-Lysine Salt

Figure 13:
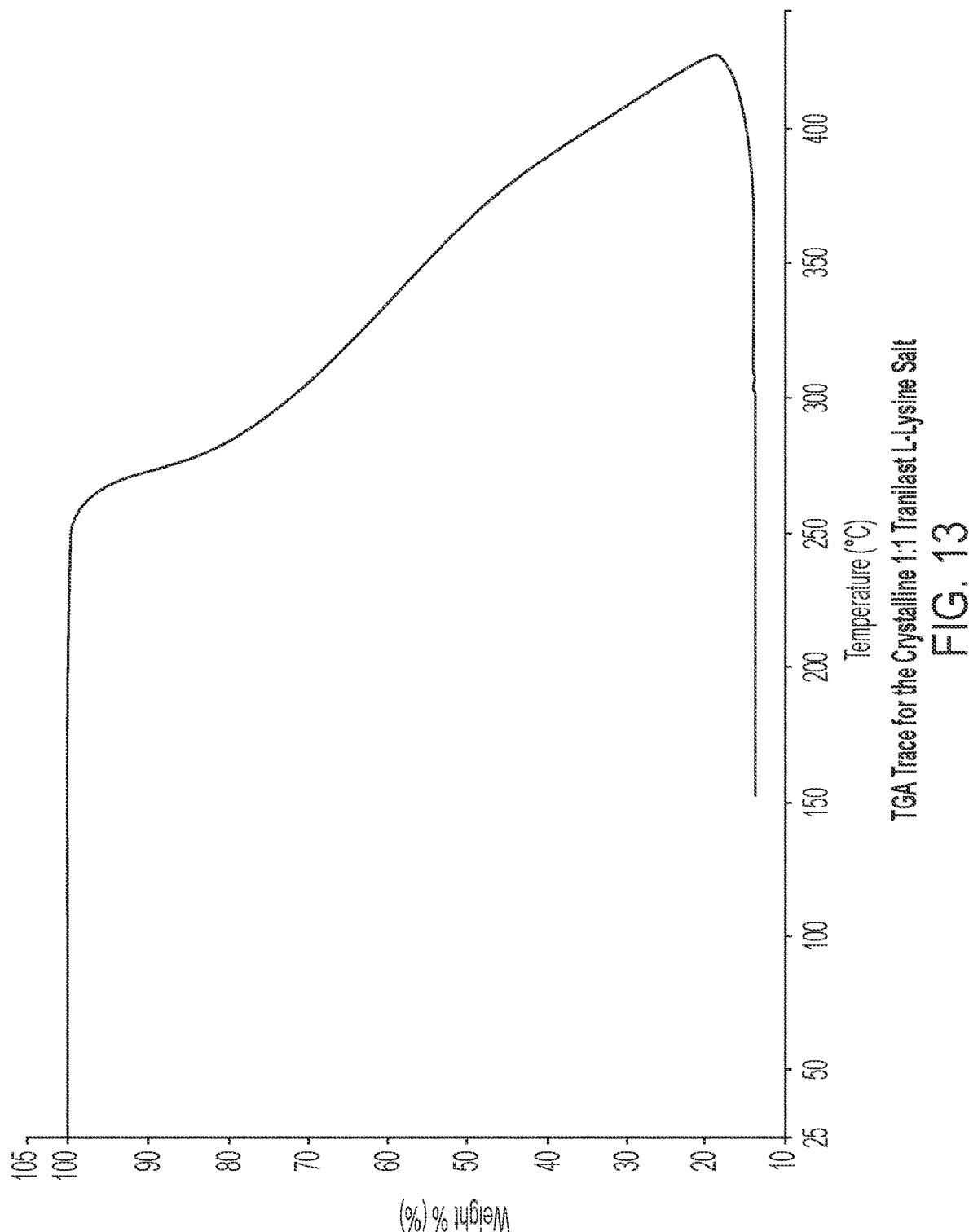
FIG. 13 depicts the TGA Trace for the crystalline 1:1 Tranilast L-Lysine salt.

The thermal gravimetric analysis (TGA) trace, FIG. 13, shows no significant weight loss prior to 255° C.

4.5 Infrared Spectrum of the Crystalline 1:1 Tranilast L-Lysine Salt

Figure 14:
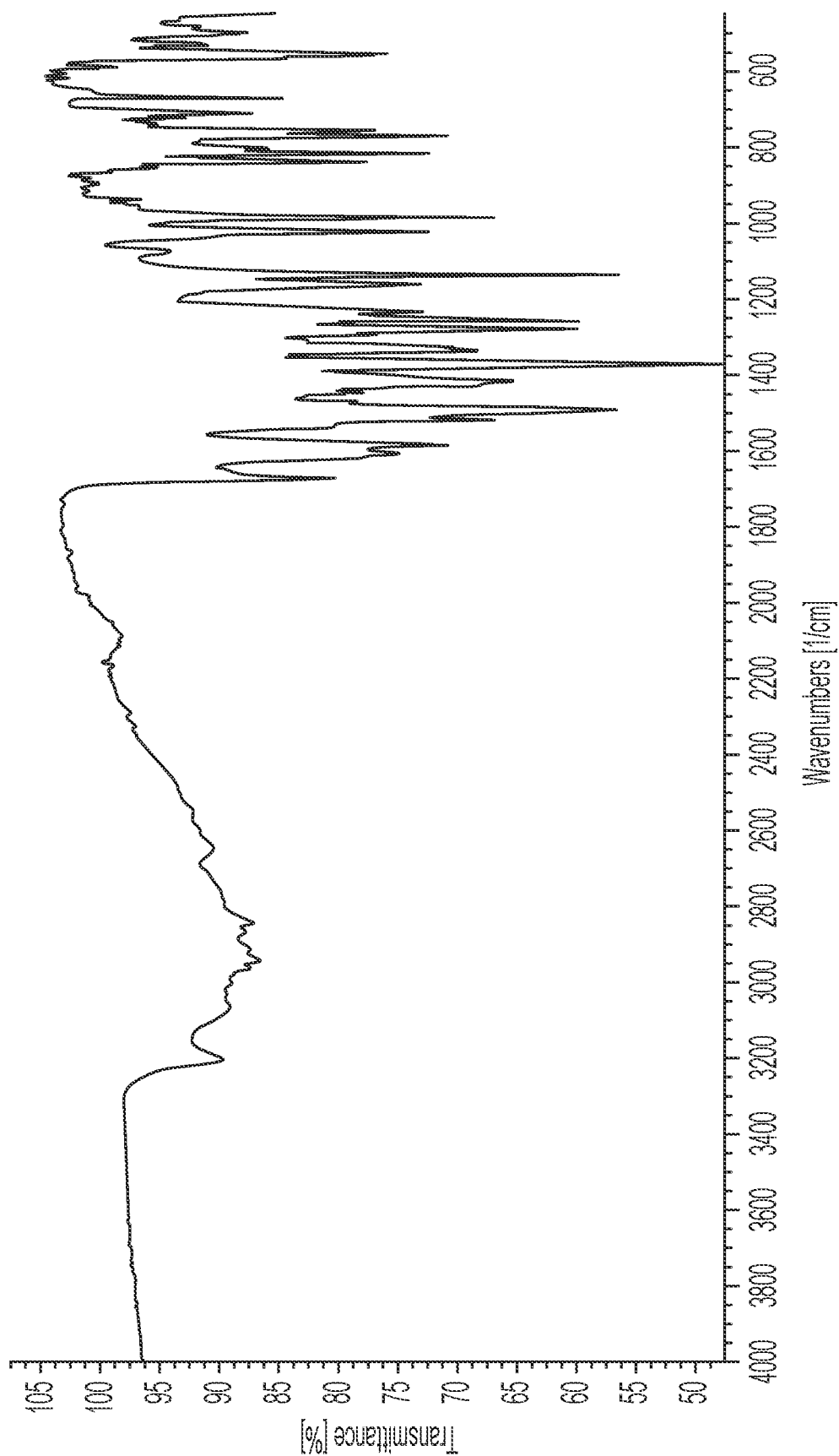
FIG. 14 depicts the Infrared Spectrum for the crystalline 1:1 Tranilast L-Lysine salt.

The experimental Infrared Spectrum of the crystalline 1:1 tranilast L-lysine salt is shown in FIG. 14. The significant peaks identified in the experimental infrared spectrum of FIG. 14 are 3204, 1670, 1602, 1584, 1516, 1493, 1415, 1371, 1335, 1277, 1254, 1232, 1159, 1135, 1020, 983, 838, 815, 770, 755 and 553 cm$^{-1}$±1 cm$^{-1}$. The entire list of peaks, or a subset thereof, may be sufficient to characterize the crystalline salt, as well as by an infrared pattern substantially similar to FIG. 14. For example, the crystalline 1:1 tranilast L-lysine salt may be characterized by at least four peaks selected from the peaks at 1670, 1584, 1493, 1371, 1277, 1254 and 1135 cm$^{-1}$±1 cm$^{-1}$.

Example 5

Crystalline 1:1 Tranilast Diethylamine Salt 5.1 Preparation of the Crystalline 1:1 Tranilast Diethylamine Salt The batch of the crystalline 1:1 tranilast diethylamine salt used for characterisation was prepared as follows:

Tranilast (100 mg) was weighed into a glass vial. Diethylamine (0.5 ml) and methanol (1.0 ml) was added to the vial. The resulting yellow slurry was placed in a shaker and shaken at ambient temperatures for approximately 24 hours. The product was then filtered under vacuum and the resulting colourless crystals were dried in a vacuum oven at 40° C. overnight.

5.2 XRPD Characterisation of the Crystalline 1:1 Tranilast Diethylamine Salt

Figure 15:
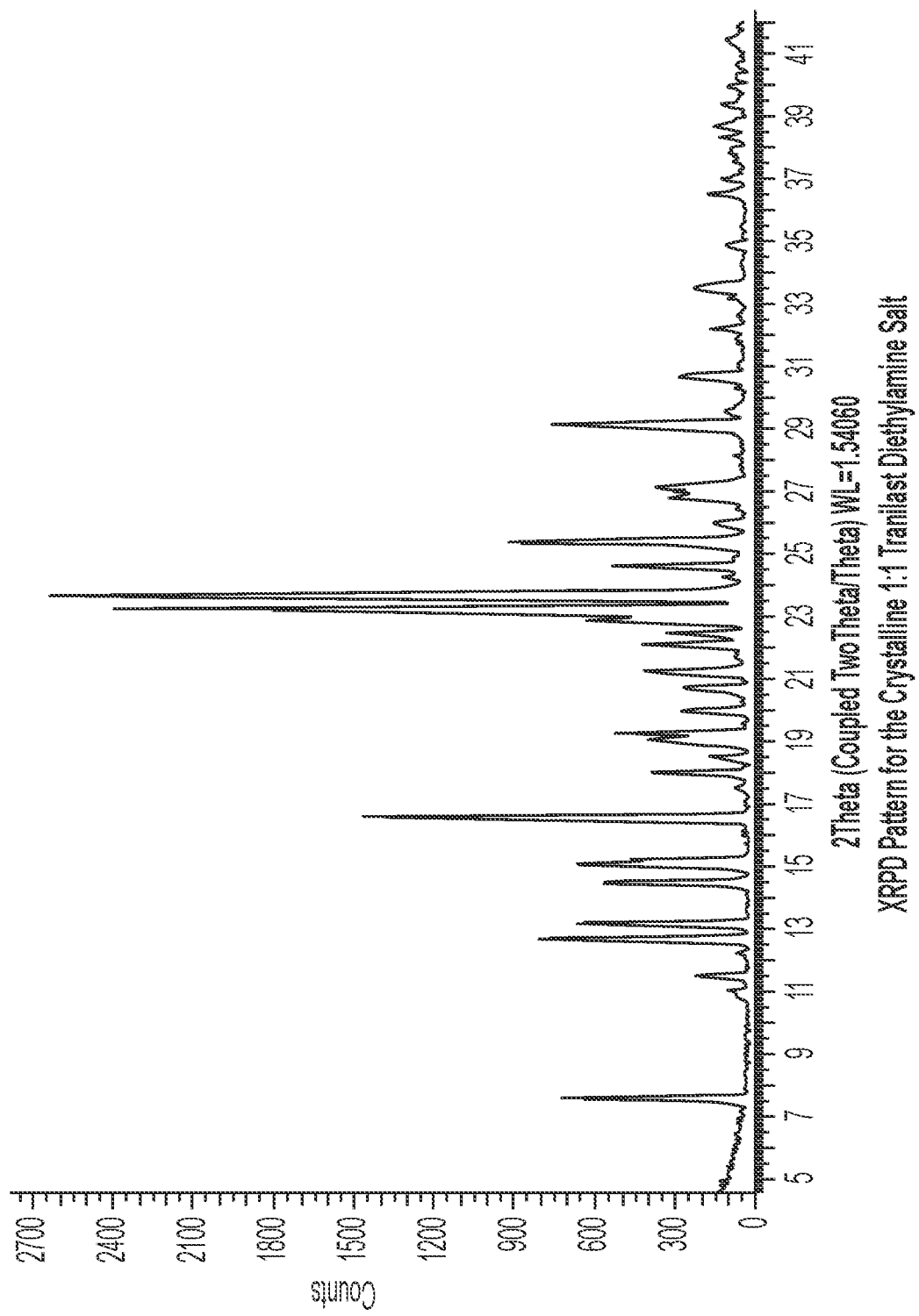
FIG. 15 depicts the XRPD Pattern for the crystalline 1:1 Tranilast Diethylamine salt.

The experimental XRPD pattern of the crystalline 1:1 tranilast diethylamine salt is shown in FIG. 15. Table 5 lists the angles, °2θ±0.2°2θ, and d value of the peaks identified in the experimental XRPD pattern of FIG. 15. The entire list of peaks or corresponding d values, or a subset thereof, may be sufficient to characterize the crystalline salt, as well as by an XRPD pattern substantially similar to FIG. 15. For example, the crystalline 1:1 tranilast diethylamine salt may be characterized by at least four peaks selected from the peaks at 7.6, 12.7, 13.2, 14.5, 16.6, 18.0 and 20.0°2θ±0.2°2θ or their corresponding d values.

TABLE 5

| Angle °2θ ± 0.2 °2θ | d value Angstrom | Intensity % |
| --- | --- | --- |
| 7.6 | 11.65 | 25.8% |
| 11.0 | 8.01 | 2.5% |
| 11.5 | 7.70 | 7.5% |
| 12.7 | 6.98 | 29.6% |
| 13.2 | 6.72 | 24.0% |
| 14.5 | 6.11 | 21.5% |
| 15.1 | 5.87 | 25.1% |
| 15.2 | 5.82 | 17.3% |
| 16.6 | 5.35 | 53.4% |
| 18.0 | 4.92 | 13.5% |
| 18.5 | 4.80 | 4.6% |
| 19.0 | 4.66 | 13.6% |
| 19.3 | 4.61 | 16.8% |
| 20.0 | 4.44 | 9.5% |
| 20.7 | 4.29 | 8.7% |
| 21.2 | 4.18 | 13.1% |
| 22.1 | 4.02 | 13.8% |
| 22.5 | 3.96 | 10.2% |
| 22.9 | 3.88 | 21.2% |
| 23.2 | 3.82 | 79.8% |
| 23.7 | 3.76 | 100.0% |
| 24.6 | 3.62 | 18.0% |
| 25.4 | 3.51 | 33.9% |
| 26.0 | 3.43 | 3.6% |
| 26.8 | 3.32 | 10.4% |
| 27.0 | 3.30 | 9.9% |
| 27.1 | 3.28 | 12.6% |
| 29.1 | 3.06 | 26.2% |
| 30.7 | 2.91 | 9.3% |
| 32.2 | 2.78 | 4.4% |
| 33.5 | 2.67 | 7.0% |
| 36.5 | 2.46 | 5.2% |
| 37.0 | 2.43 | 3.1% |
| 38.3 | 2.35 | 3.2% |
| 38.7 | 2.33 | 3.9% |
| 39.4 | 2.29 | 3.0% |

5.3 DSC of the Crystalline 1:1 Tranilast Diethylamine Salt

Figure 16:
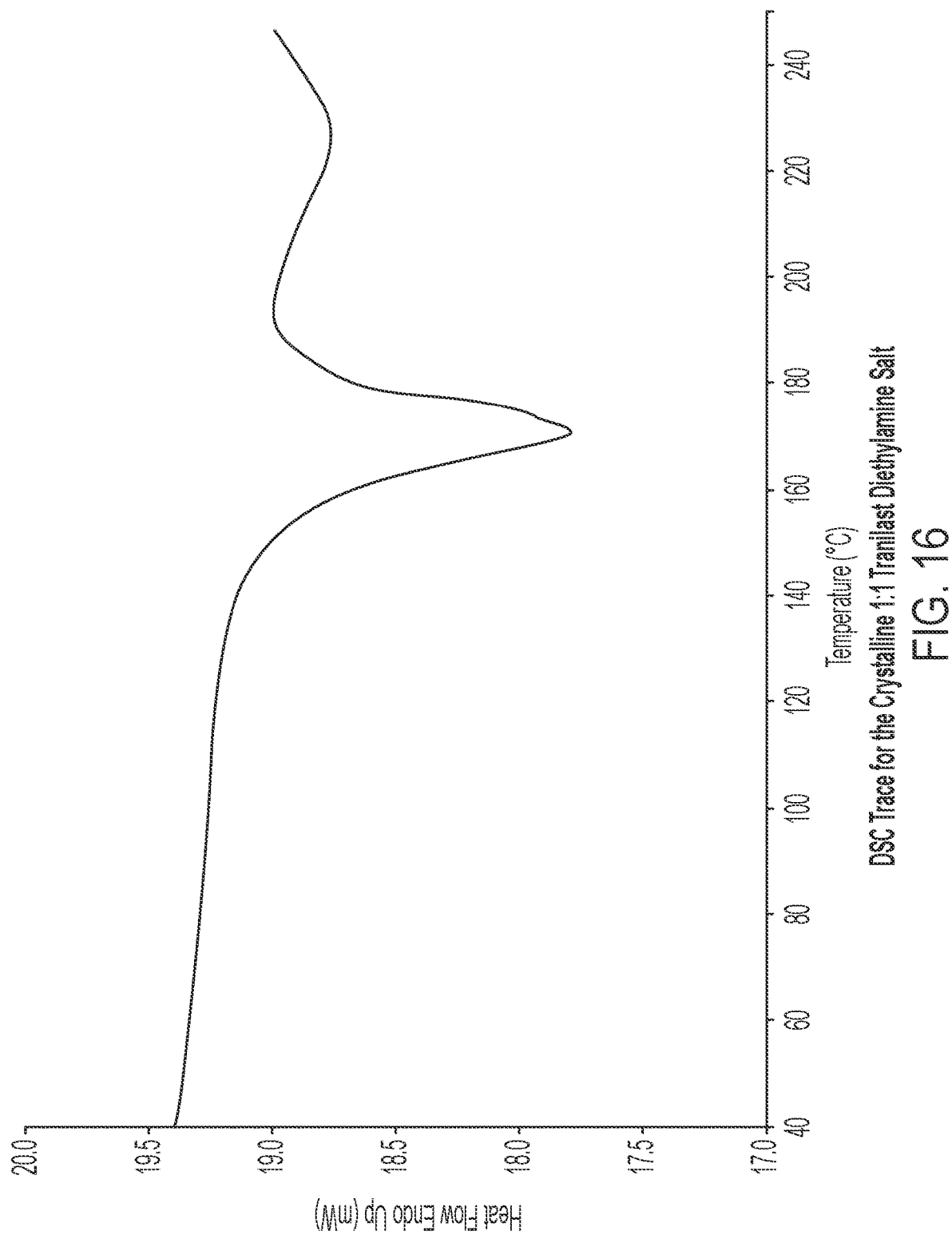
FIG. 16 depicts the DSC Trace for the crystalline 1:1 Tranilast Diethylamine salt.

The differential scanning calorimetry (DSC) trace, FIG. 16, shows a broad endotherm with peak maximum of 170.9° C.

5.4 TGA of the Crystalline the 1:1 Tranilast Diethylamine Salt

Figure 17:
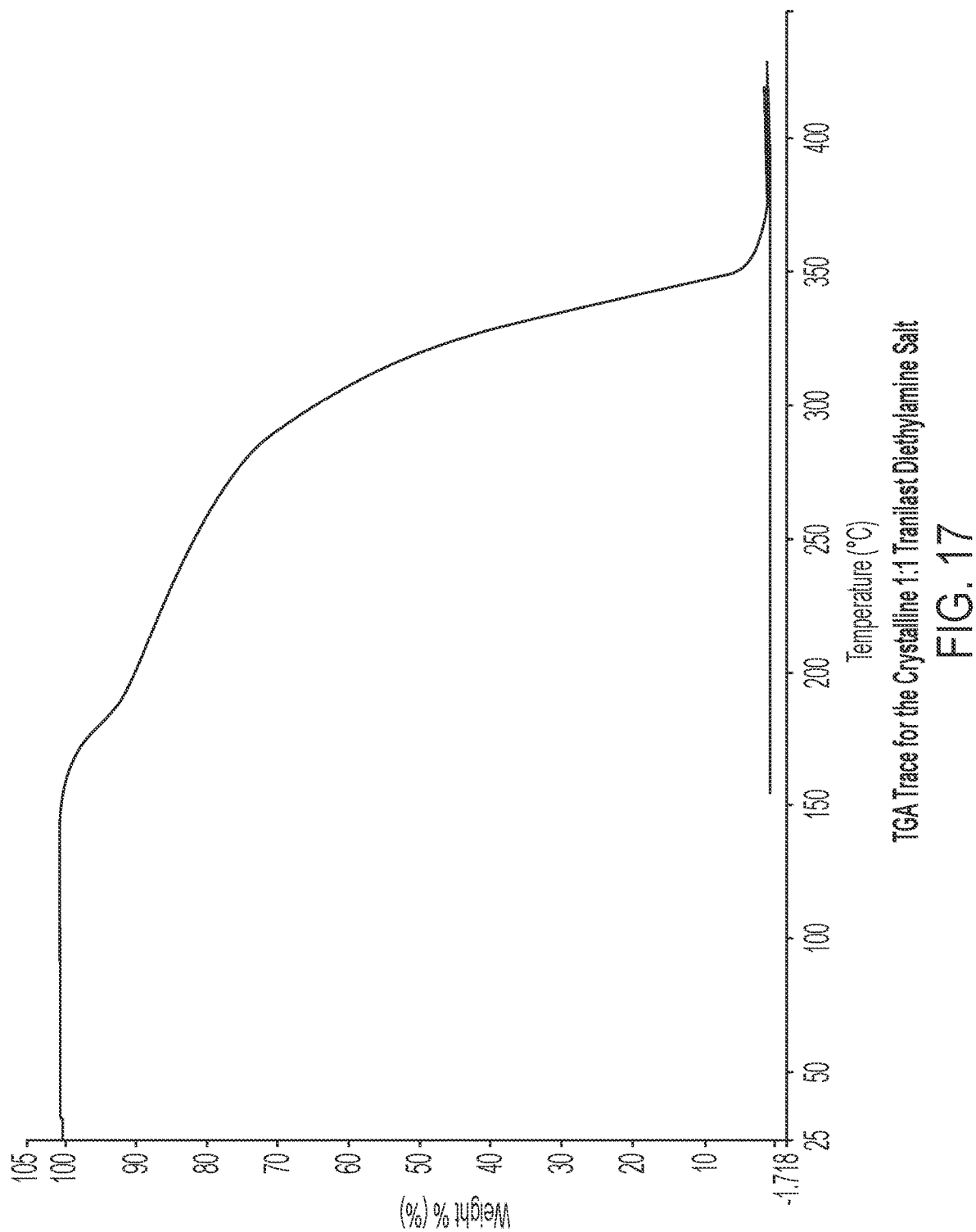
FIG. 17 depicts the TGA Trace for the crystalline 1:1 Tranilast Diethylamine salt.

The thermal gravimetric analysis (TGA) trace, FIG. 17, shows weight loss begins at around 155° C.

5.5 Infrared Spectrum of the Crystalline the 1:1 Tranilast Diethylamine Salt

Figure 18:
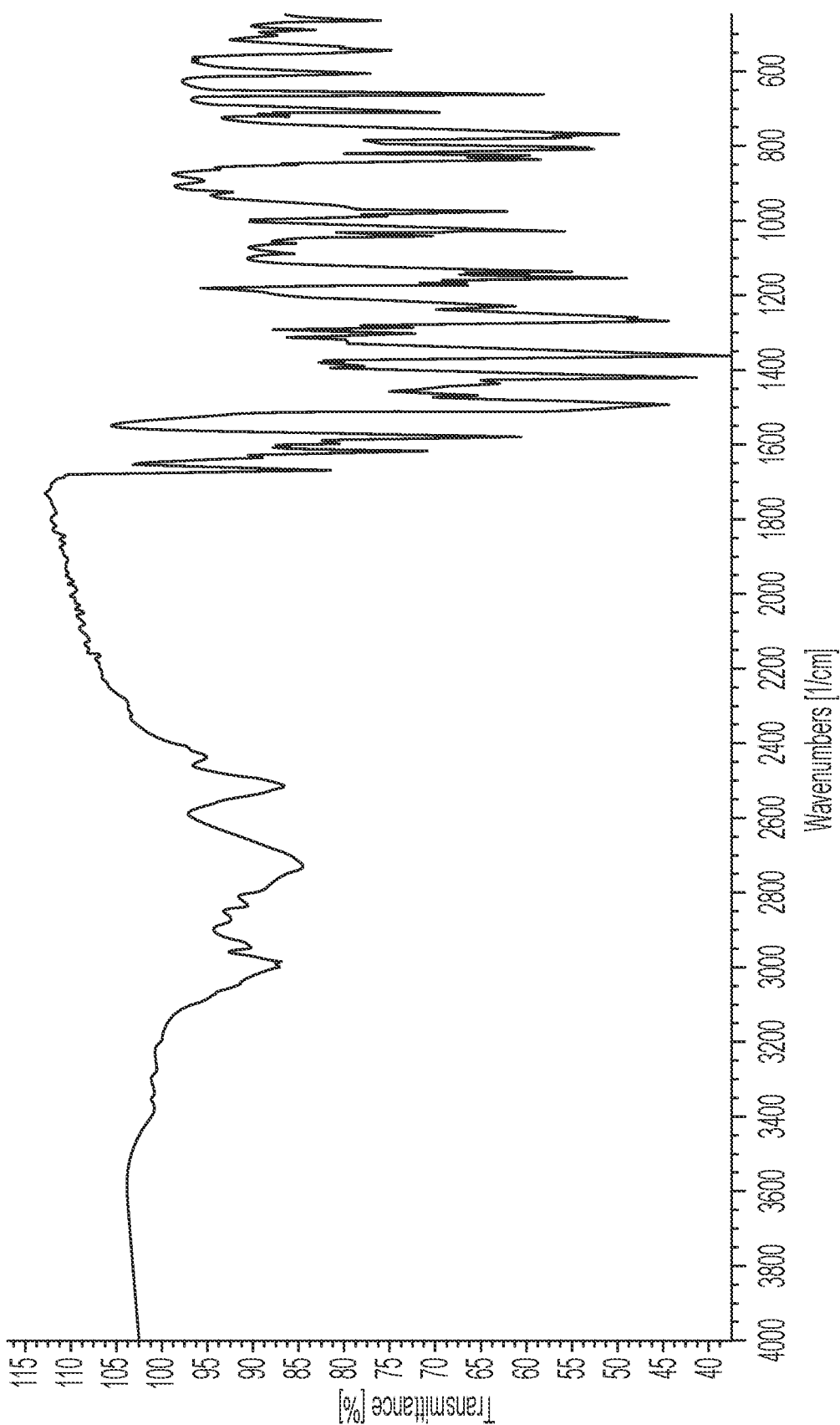
FIG. 18 depicts the Infrared Spectrum for the crystalline 1:1 Tranilast Diethylamine salt.

The experimental Infrared Spectrum of the crystalline 1:1 tranilast diethylamine salt is shown in FIG. 18. The significant peaks identified in the experimental infrared spectrum of FIG. 18 are 2987, 2515, 1669, 1618, 1579, 1495, 1467, 1419, 1361, 1303, 1272, 1231, 1155, 1138, 1027, 977, 838, 808, 771, 707, 663, 606, 545 and 465 cm$^{-1}$±1 cm$^{-1}$. The entire list of peaks, or a subset thereof, may be sufficient to characterize the crystalline salt, as well as by an infrared pattern substantially similar to FIG. 18. For example, the crystalline 1:1 tranilast diethylamine salt may be characterized by at least four peaks selected from the peaks at 1669, 1618, 1579, 1495, 1419, 1361 and 1155 cm$^{-1}$±1 cm$^{-1}$.

Example 6

Crystalline 1:1 Tranilast N-Ethylglucamine Salt 6.1 Preparation of the Crystalline 1:1 Tranilast N-ethylglucamine Salt The batch of the crystalline 1:1 tranilast N-ethylglucamine used for characterisation was prepared as follows:

Tranilast (100 mg) and N-ethylglucamine (63.9 mg) were weighed into a glass vial. Acetone (1.5 ml) was added to the vial. The resulting yellow slurry was placed in a shaker and shaken at ambient temperatures for approximately 24 hours. The product was then filtered under vacuum and the resulting colourless crystals were dried in a vacuum oven at 40° C. overnight.

6.1 XRPD Characterisation of the Crystalline 1:1 N-ethylglucamine Salt

Figure 19:
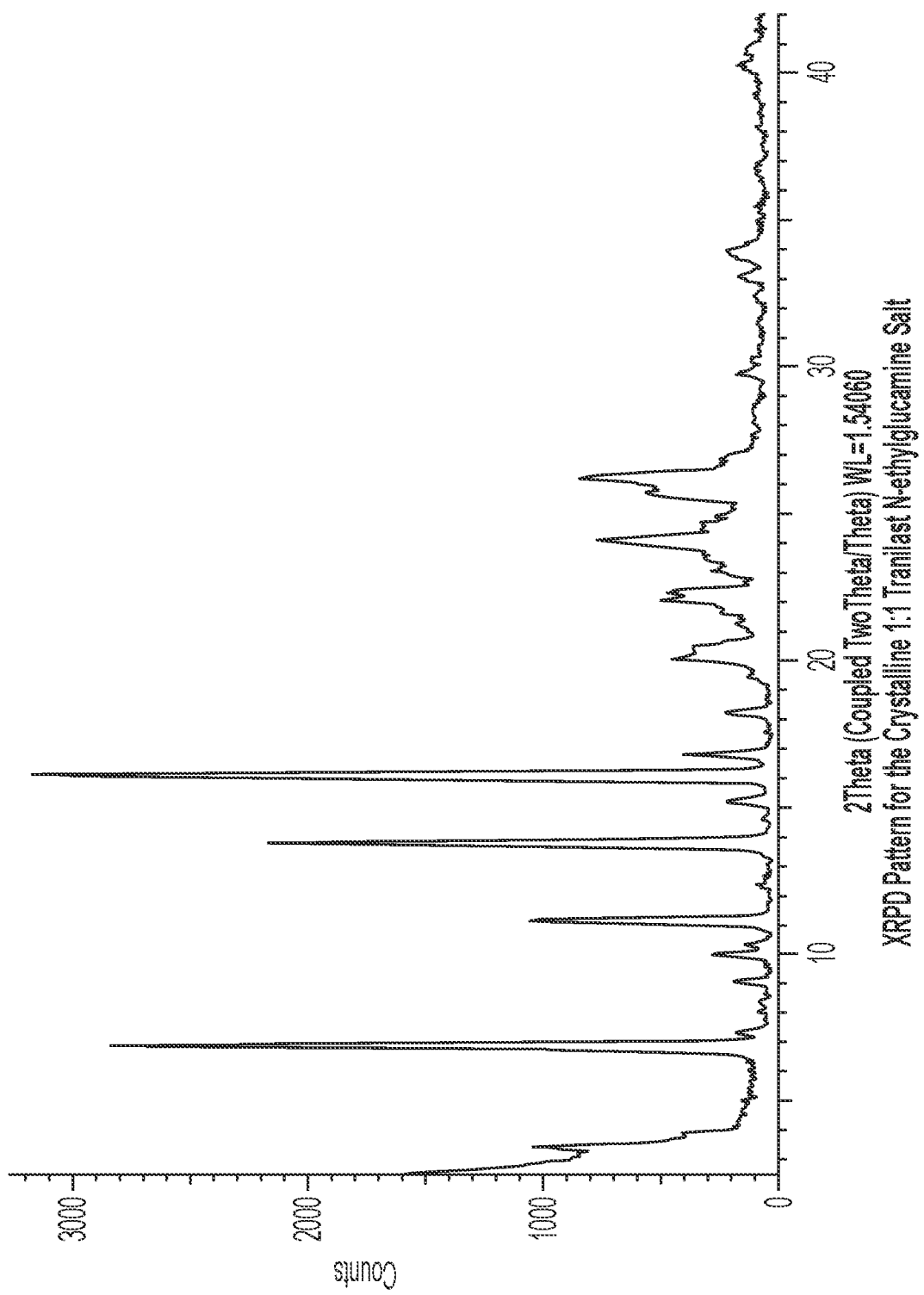
FIG. 19 depicts the XRPD Pattern for the crystalline 1:1 Tranilast N-ethylglucamine salt.

The experimental XRPD pattern of the crystalline 1:1 tranilast N-ethylglucamine salt is shown in FIG. 19. Table 6 lists the angles, °2θ±0.2°2θ, and d value of the peaks identified in the experimental XRPD pattern of FIG. 19. The entire list of peaks or d values, or a subset thereof, may be sufficient to characterize the crystalline salt, as well as by an XRPD pattern substantially similar to FIG. 19. For example, the crystalline 1:1 tranilast N-ethylglucamine salt may be characterized by at least four peaks selected from peaks at 6.9, 11.1, 13.8, 15.2 16.1 16.8 and 18.2°2θ±0.2°2θ or their corresponding d values.

TABLE 6

| Angle °2θ ± 0.2 °2θ | d value Angstrom | Intensity % |
| --- | --- | --- |
| 3.4 | 25.81 | 10.9% |
| 6.9 | 12.83 | 87.7% |
| 7.3 | 12.05 | 3.6% |
| 9.1 | 9.74 | 4.5% |
| 10.0 | 8.83 | 7.5% |
| 10.4 | 8.54 | 2.8% |
| 11.1 | 7.94 | 33.2% |
| 13.8 | 6.42 | 68.8% |
| 15.2 | 5.82 | 5.4% |
| 16.1 | 5.50 | 100.0% |
| 16.8 | 5.27 | 11.5% |
| 18.2 | 4.86 | 5.8% |
| 20.1 | 4.42 | 11.5% |
| 20.4 | 4.35 | 8.8% |
| 22.1 | 4.02 | 11.7% |
| 22.3 | 3.98 | 9.6% |
| 24.1 | 3.69 | 19.9% |
| 25.7 | 3.46 | 13.5% |
| 26.2 | 3.39 | 22.7% |
| 29.8 | 2.99 | 2.7% |
| 33.1 | 2.71 | 2.9% |
| 33.9 | 2.64 | 4.2% |

6.2 DSC of the Crystalline 1:1 Tranilast N-ethylglucamine Salt

Figure 20:
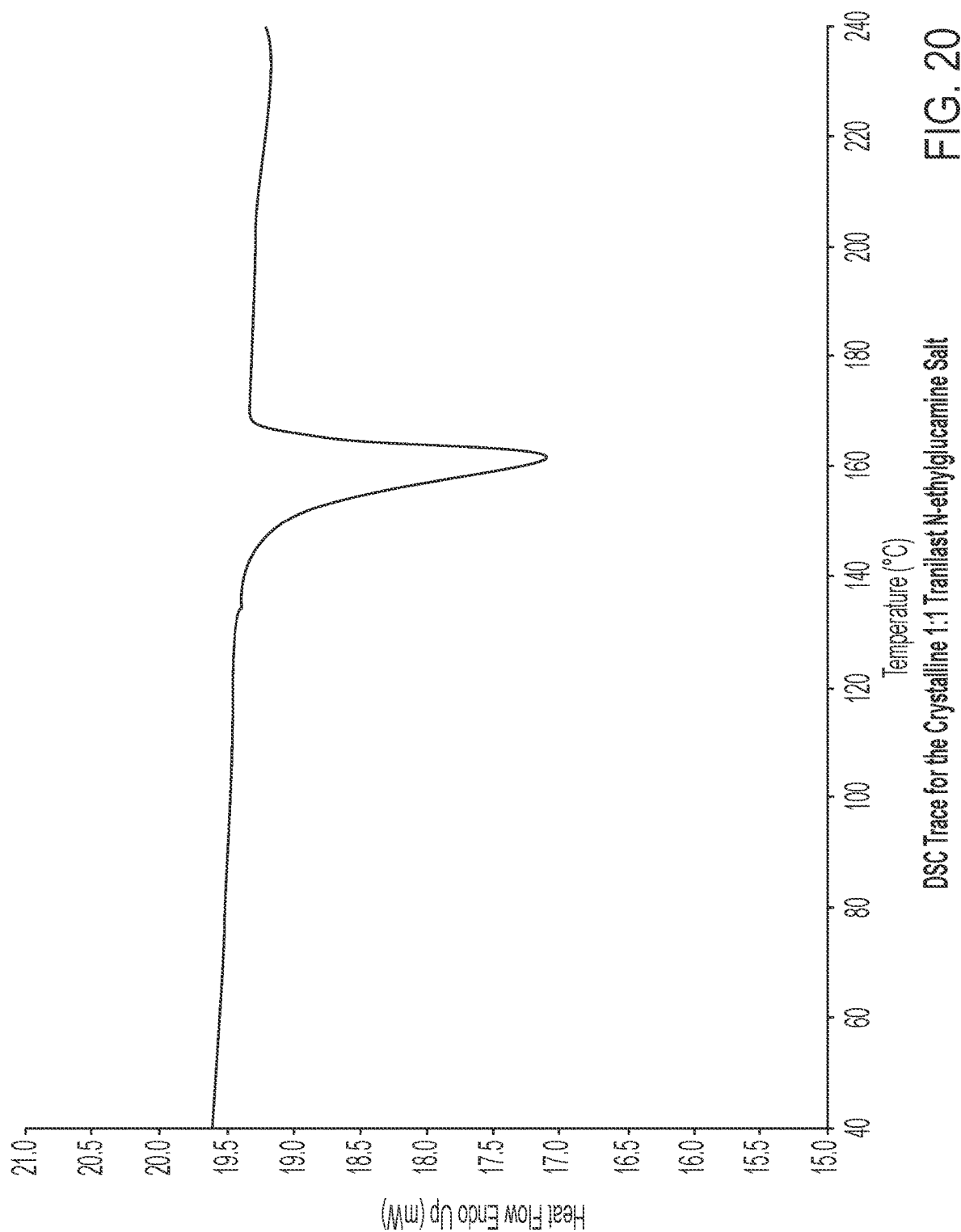
FIG. 20 depicts the DSC Trace for the crystalline 1:1 Tranilast N-ethylglucamine salt.

The differential scanning calorimetry (DSC) trace, FIG. 20, shows a single endotherm with a peak maximum of 161.7° C.

6.3 TGA of the Crystalline 1:1 Tranilast N-ethylglucamine Salt

Figure 21:
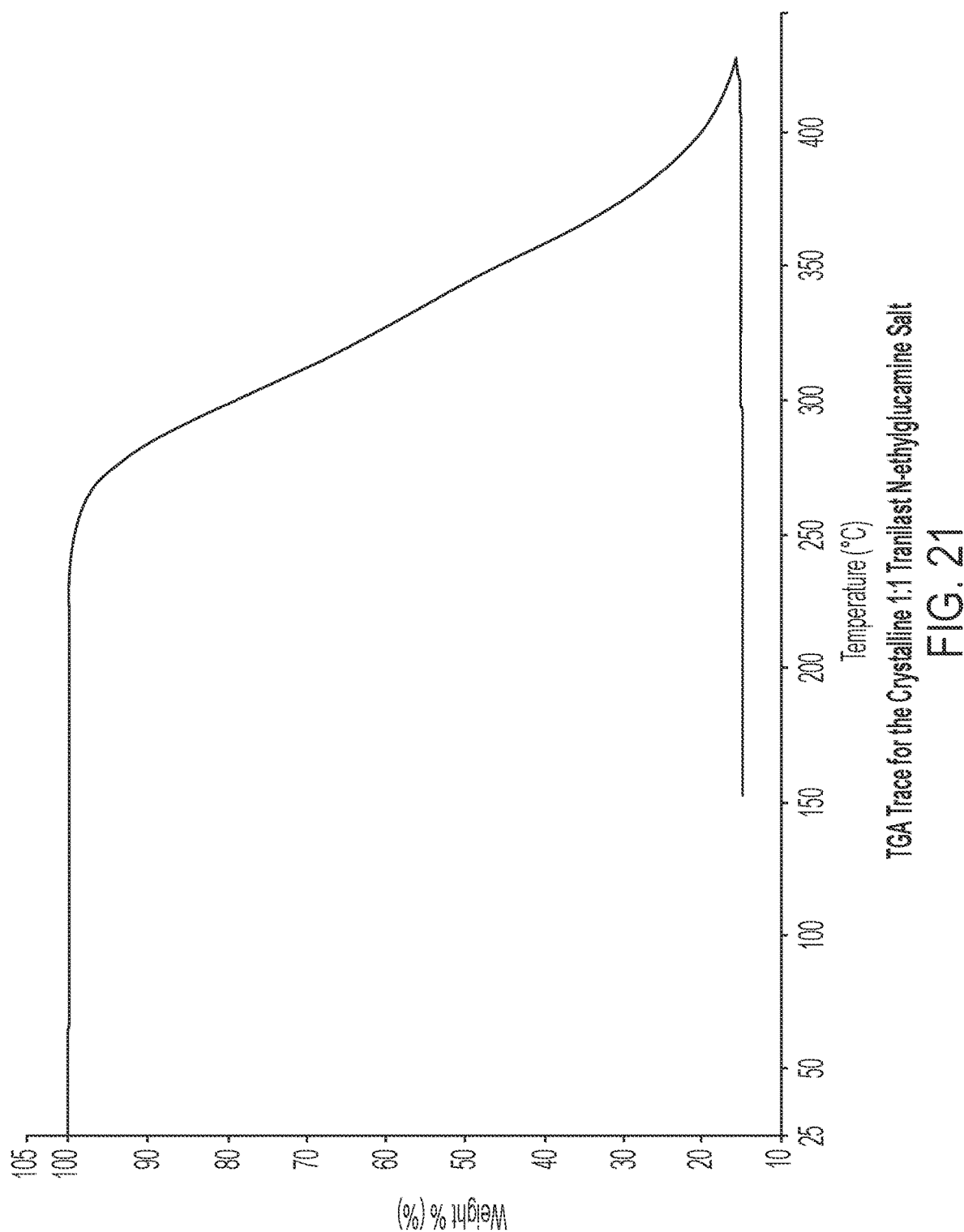
FIG. 21 depicts the TGA Trace for the crystalline 1:1 Tranilast N-ethylglucamine salt.

The thermal gravimetric analysis (TGA) trace, FIG. 21, shows no significant weight loss prior to 255° C.

6.4 Infrared Spectrum of the Crystalline 1:1 Tranilast N-ethylglucamine Salt

Figure 22:
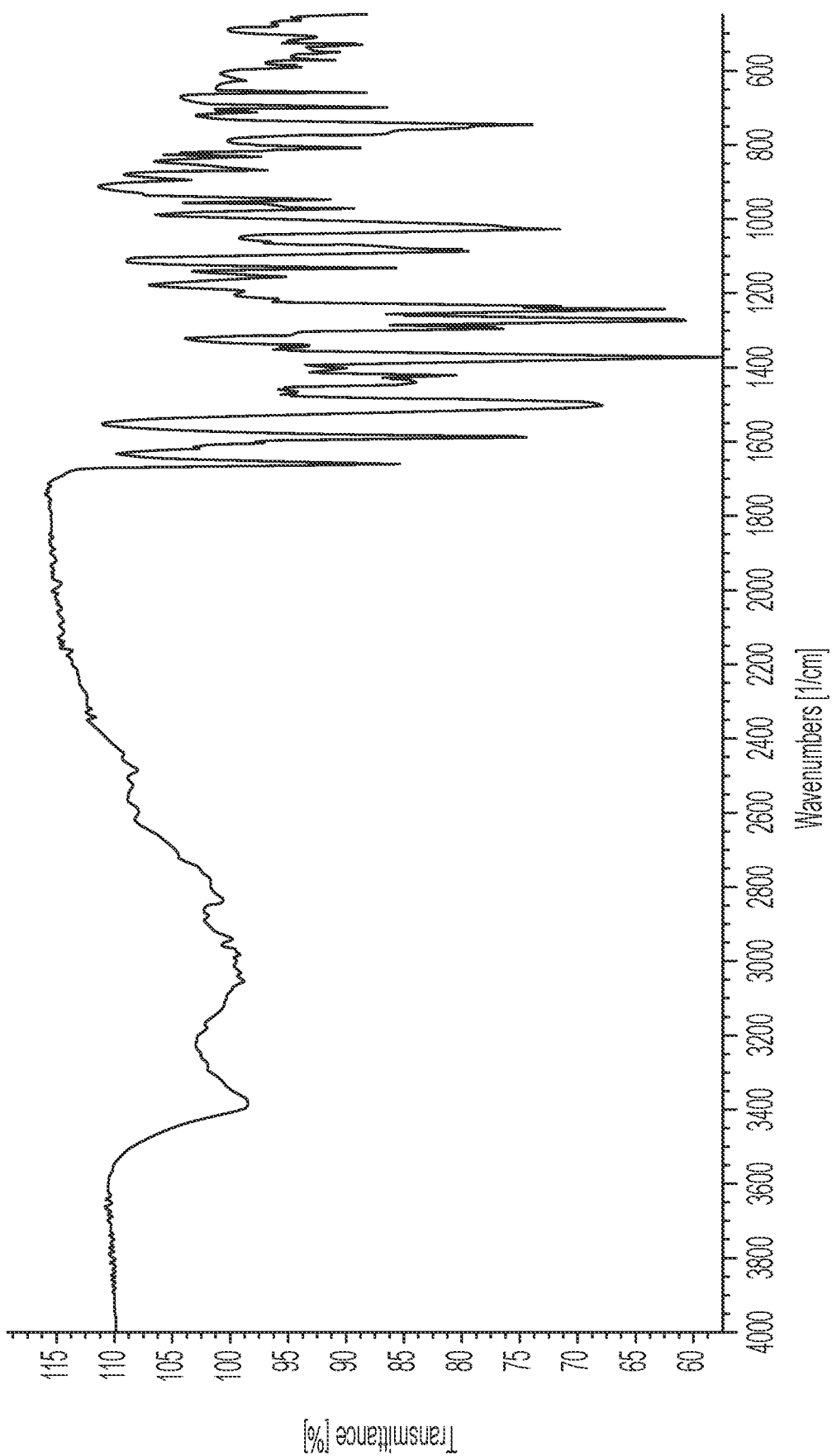
FIG. 22 depicts the Infrared Spectrum for the crystalline 1:1 Tranilast N-ethylglucamine salt.

The experimental Infrared Spectrum of the crystalline 1:1 tranilast N-ethylglucamine Form I salt is shown in FIG. 22. The significant peaks identified in the experimental infrared spectrum of FIG. 22 are 1660, 1589, 1504, 1441, 1423, 1403, 1374, 1295, 1273, 1244, 1134, 1087, 1028, 974, 809, 748, 700, 662 and 530 cm$^{-1}$±1 cm$^{-1}$. The entire list of peaks, or a subset thereof, may be sufficient to characterize the crystalline salt, as well as by an infrared pattern substantially similar to FIG. 22. For example, the crystalline 1:1 tranilast N-ethylglucamine Form I salt may be characterized by at least four peaks selected from the peaks at 1660, 1589, 1423, 1374, 1295, 1273 and 1244 cm$^{-1}$±1 cm$^{-1}$.

Example 7

Crystalline 1:1 Tranilast Potassium Monohydrate Salt 7.1 Preparation of Crystalline 1:1 Tranilast Potassium Monohydrate Salt The batch of the crystalline 1:1 tranilast potassium monohydrate salt used for characterisation was prepared as follows:

Tranilast (200 mg) was weighed into a glass vial. Methanol (2.0 ml) was added to the vial to give a yellow slurry. On addition of 2.0 M potassium hydroxide solution (2.0 ml) a solution was formed. The vial was placed in a shaker and shaken at ambient temperatures for approximately 24 hours suring which time an off-white precipitate was formed. The product was then filtered under vacuum and the resulting crystals were dried in a vacuum oven at 40° C. overnight.

Figure 23:
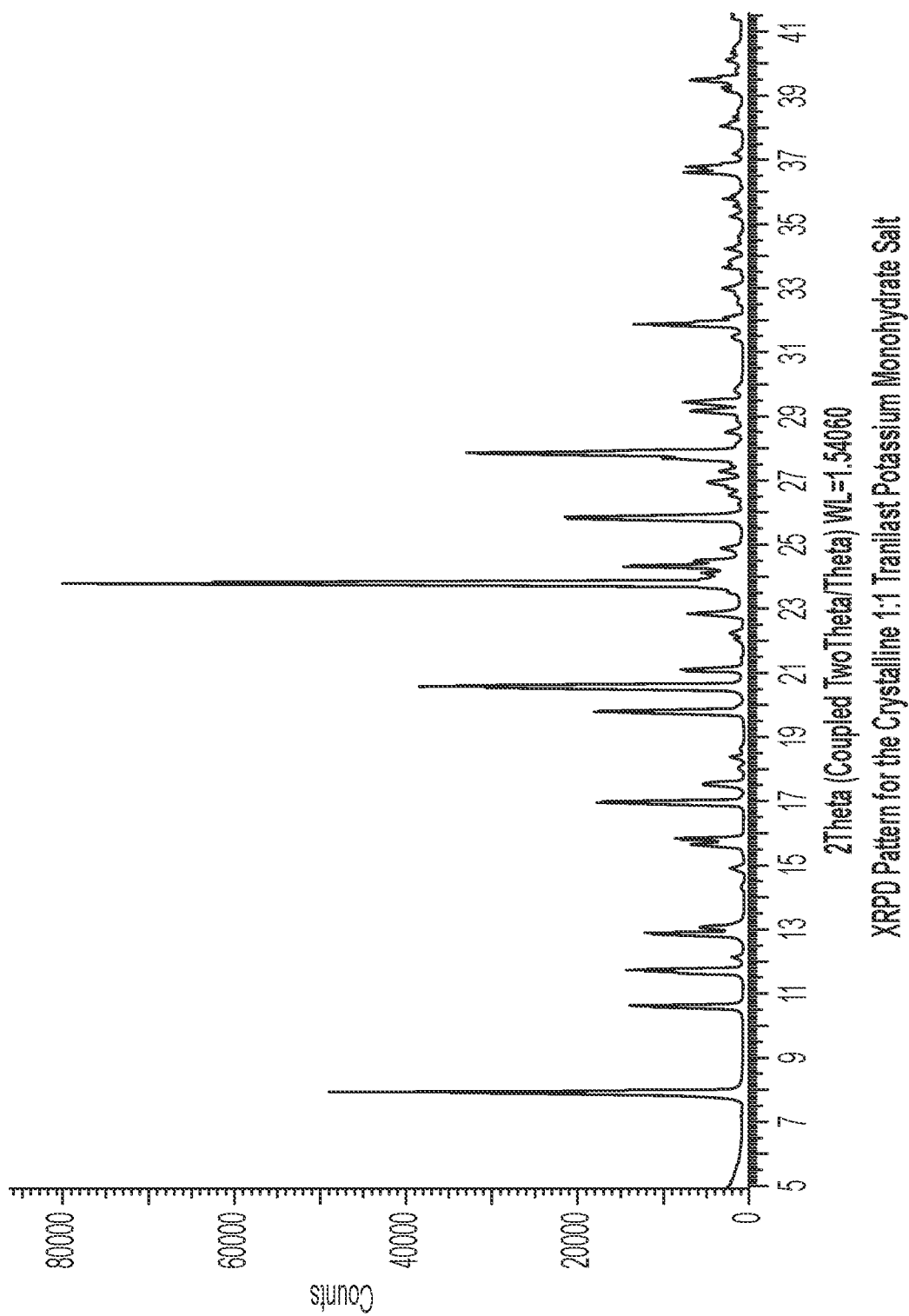
FIG. 23 depicts the XRPD Pattern for the crystalline 1:1 Tranilast Potassium Monohydrate salt.

7.2 XRPD Characterisation of the Crystalline 1:1 Tranilast Potassium Monohydrate Salt The experimental XRPD pattern of crystalline 1:1 tranilast potassium monohydrate salt is shown in FIG. 23. Table 7 lists the angles, °2θ±0.2°2θ, and d value of the peaks identified in the experimental XRPD pattern of FIG. 23. The entire list of peaks or corresponding d values, or a subset thereof, may be sufficient to characterize the crystalline salt, as well as by an XRPD pattern substantially similar to FIG. 23. For example, the crystalline 1:1 tranilast potassium monohydrate salt may be characterized by at least four peaks selected from the peaks at 7.9, 10.6, 11.7, 14.9, 17.0, 19.8 and 20.6°2θ±0.2°2θ or their corresponding d values.

TABLE 7

| Angle °2θ ± 0.2 °2θ | d value Angstrom | Intensity % |
| --- | --- | --- |
| 7.9 | 11.12 | 60.5% |
| 10.6 | 8.32 | 16.5% |
| 11.7 | 7.53 | 17.4% |
| 12.1 | 7.29 | 1.5% |
| 12.9 | 6.87 | 14.6% |
| 13.1 | 6.76 | 6.3% |
| 14.9 | 5.94 | 2.0% |
| 15.7 | 5.66 | 7.9% |
| 15.8 | 5.59 | 10.1% |
| 17.0 | 5.22 | 21.7% |
| 17.5 | 5.05 | 6.0% |
| 19.8 | 4.48 | 21.7% |
| 20.6 | 4.31 | 47.3% |

TABLE 7-continued

| Angle °2θ ± 0.2 °2θ | d value Angstrom | Intensity % |
|---|---|---|
| 21.1 | 4.21 | 9.0% |
| 22.8 | 3.89 | 8.1% |
| 23.8 | 3.74 | 100.0% |
| 24.1 | 3.69 | 5.7% |
| 24.3 | 3.66 | 17.1% |
| 24.5 | 3.63 | 6.9% |
| 24.9 | 3.57 | 3.0% |
| 25.8 | 3.45 | 25.7% |
| 27.0 | 3.31 | 4.9% |
| 27.3 | 3.27 | 3.0% |
| 27.8 | 3.20 | 40.1% |
| 28.5 | 3.13 | 2.1% |
| 29.2 | 3.06 | 7.5% |
| 29.4 | 3.03 | 8.6% |
| 31.9 | 2.81 | 15.7% |
| 33.0 | 2.71 | 3.0% |
| 34.2 | 2.62 | 2.5% |
| 35.8 | 2.51 | 2.7% |
| 36.6 | 2.45 | 8.4% |
| 36.8 | 2.44 | 8.0% |
| 38.1 | 2.36 | 2.5% |
| 39.5 | 2.28 | 7.4% |

Figure 24:
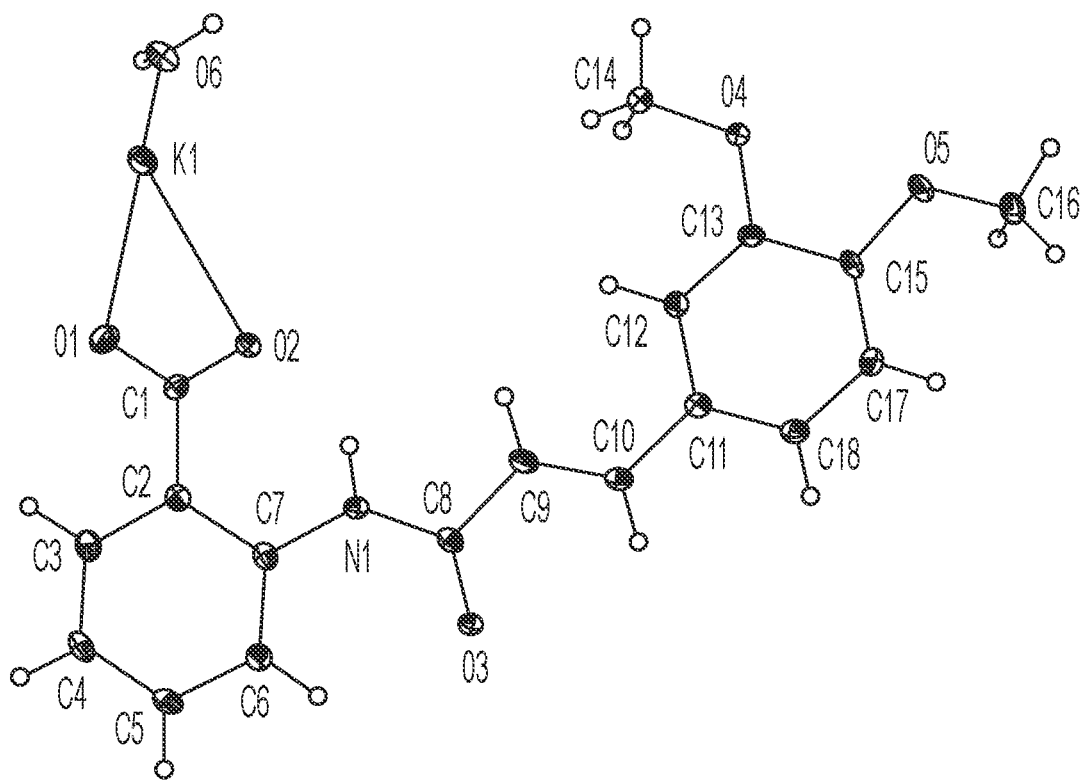
FIG. 24 depicts the ORTEP drawing of the crystalline 1:1 Tranilast Potassium Monohydrate salt.
Figure 25:
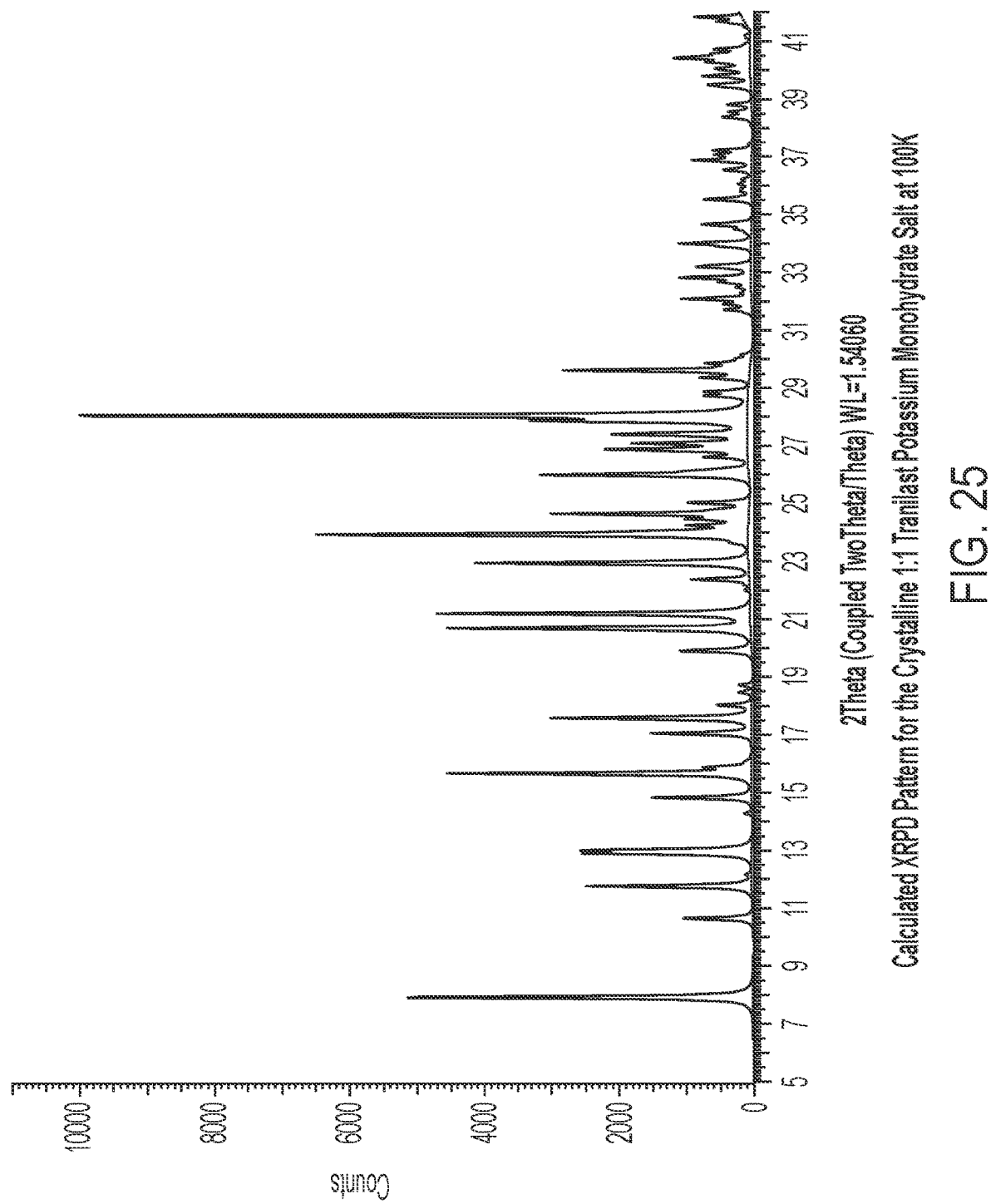
FIG. 25 depicts the calculated XRPD Pattern for the crystalline 1:1 Tranilast Potassium Monohydrate salt at 100K.

7.3 SCXRD Characterisation of Crystalline 1:1 Tranilast Potassium Monohydrate Salt The crystal used for single crystal structure determination was selected from the batch of crystals prepared as described above. The single crystal data and structure refinement parameters are reported in Table 8, below. FIG. 24 shows an ORTEP drawing of the asymmetric unit from the crystal structure of the crystalline 1:1 tranilast potassium monohydrate salt showing the atom numbering scheme employed. Anisotropic atomic displacement ellipsoids for the non-hydrogen atoms are shown at the 50% probability level and hydrogen atoms are displayed as spheres of arbitrary radius. The calculated XRPD pattern based on the single crystal data and structure for the crystalline 1:1 tranilast potassium monohydrate salt at 100 K is shown in FIG. 25. It is also noted that there are some small temperature shifts in some of the peaks owing to the fact that the experimental XRPD pattern was collected at room temperature and the calculated XRPD pattern is derived from data collected at 100 K. There are also small intensity differences owing to preferred orientation effects, present in the experimental pattern.

TABLE 8

| | |
|---|---|
| Molecular formula | $C_{18}H_{18}K_1N_1O_6$ |
| Molecular weight | 383.43 |
| Crystal System | Monoclinic |
| Space Group | P21/c |
| Unit Cell Dimensions | a = 6.81928(10) Å |
| | b = 15.0301(2) Å |
| | c = 16.6691(2) Å |
| | α = 90.00° |
| | β = 95.1842(14)° |
| | γ = 90.00° |
| Cell Volume | 1701.50(4) Å³ |
| Z | 4 |
| Temperature | 100(1) K |
| Radiation Wavelength/type | 1.54184 Å/CuKα |
| Goodness of fit | 1.008 |
| R factor | 0.0290 |
| Morphology | Colourless prism |

A second SCXRD data set on the 1:1 tranilast potassium monohydrate salt at ambient temperatures.

The single crystal data and structure refinement parameters for the structure measured at 295 K are reported in Table 9, below.

Figure 26:
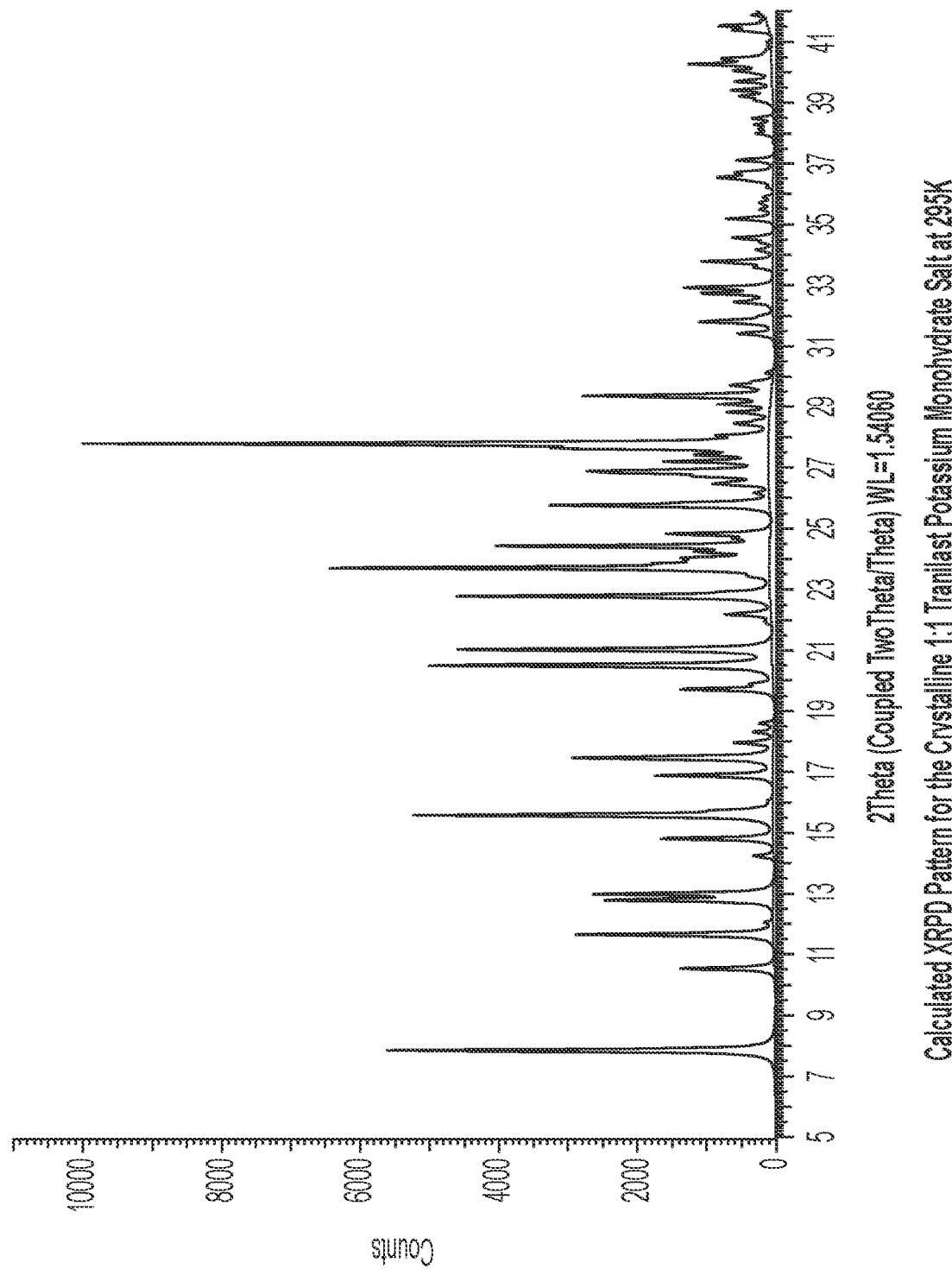
FIG. 26 depicts the calculated XRPD Pattern for the crystalline 1:1 Tranilast Potassium Monohydrate salt at 295K.

The calculated XRPD pattern based on the single crystal data and structure for the crystalline 1:1 tranilast potassium monohydrate salt at 295 K is shown in FIG. 26. It is can be seen that in this case there is good agreement between the experimental XRPD pattern collected at room temperature (FIG. 23) and the calculated XRPD pattern is derived from data collected at 295 K. There are small intensity differences owing to preferred orientation effects present in the experimental pattern.

TABLE 9

| | |
|---|---|
| Molecular formula | $C_{18}H_{18}K_1N_1O_6$ |
| Molecular weight | 383.43 |
| Crystal System | Monoclinic |
| Space Group | P21/c |
| Unit Cell Dimensions | a = 6.82507(8) Å |
| | b = 15.1599(2) Å |
| | c = 16.8200(2) Å |
| | α = 90.00° |
| | β = 94.8339(11)° |
| | γ = 90.00° |
| Cell Volume | 1734.13(4) Å³ |
| Z | 4 |
| Temperature | 295(1) K |
| Radiation Wavelength/type | 1.54178 Å/CuKα |
| Goodness of fit | 1.023 |
| R factor | 0.0852 |
| Morphology | Colourless prism |

7.4 DSC of the Crystalline 1:1 Tranilast Potassium Monohydrate Salt

Figure 27:
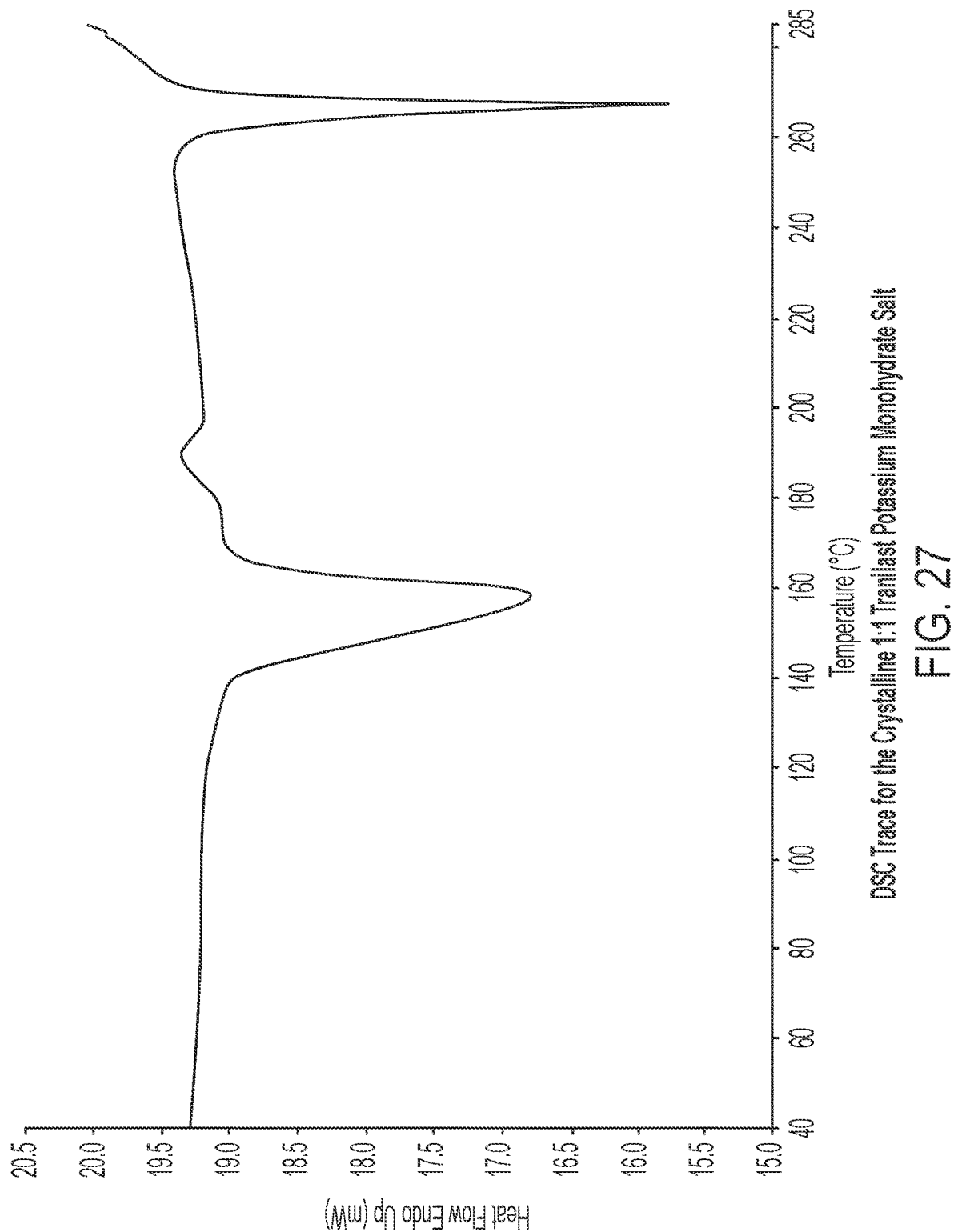
FIG. 27 depicts the DSC Trace for the crystalline 1:1 Tranilast Potassium Monohydrate salt.

The differential scanning calorimetry (DSC) trace, FIG. 27, shows a a broad endotherm with a peak maximum of 185° C. followed by a sharp endotherm with a peak maximum of 268° C.

7.5 TGA of the Crystalline 1:1 Tranilast Potassium Monohydrate Salt

Figure 28:
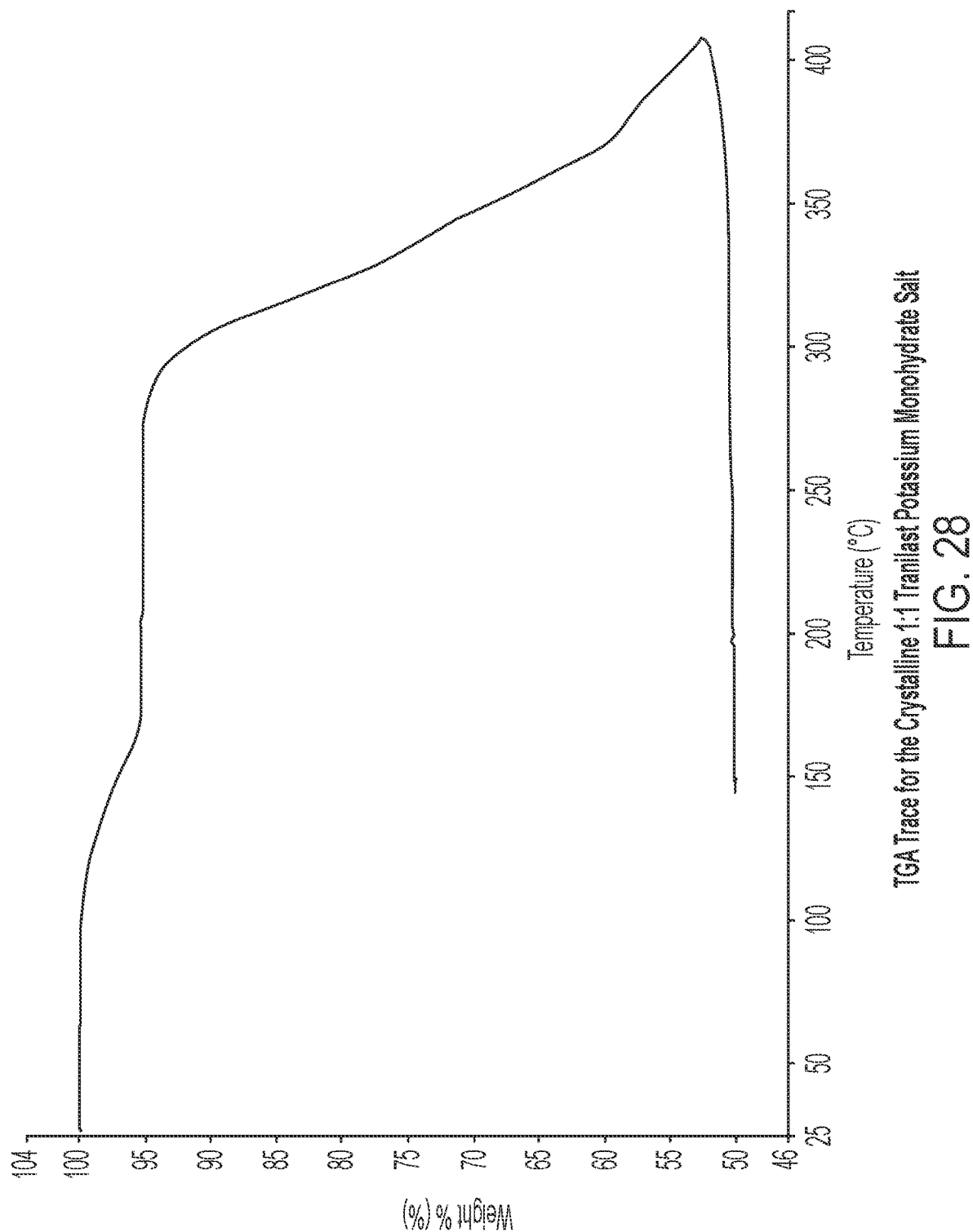
FIG. 28 depicts the TGA Trace for the crystalline 1:1 Tranilast Potassium Monohydrate salt.

The thermal gravimetric analysis (TGA) trace, FIG. 28, shows a weight loss of 4.7% between 105 and 170° C. which corresponds to one mole of water.

Figure 29:
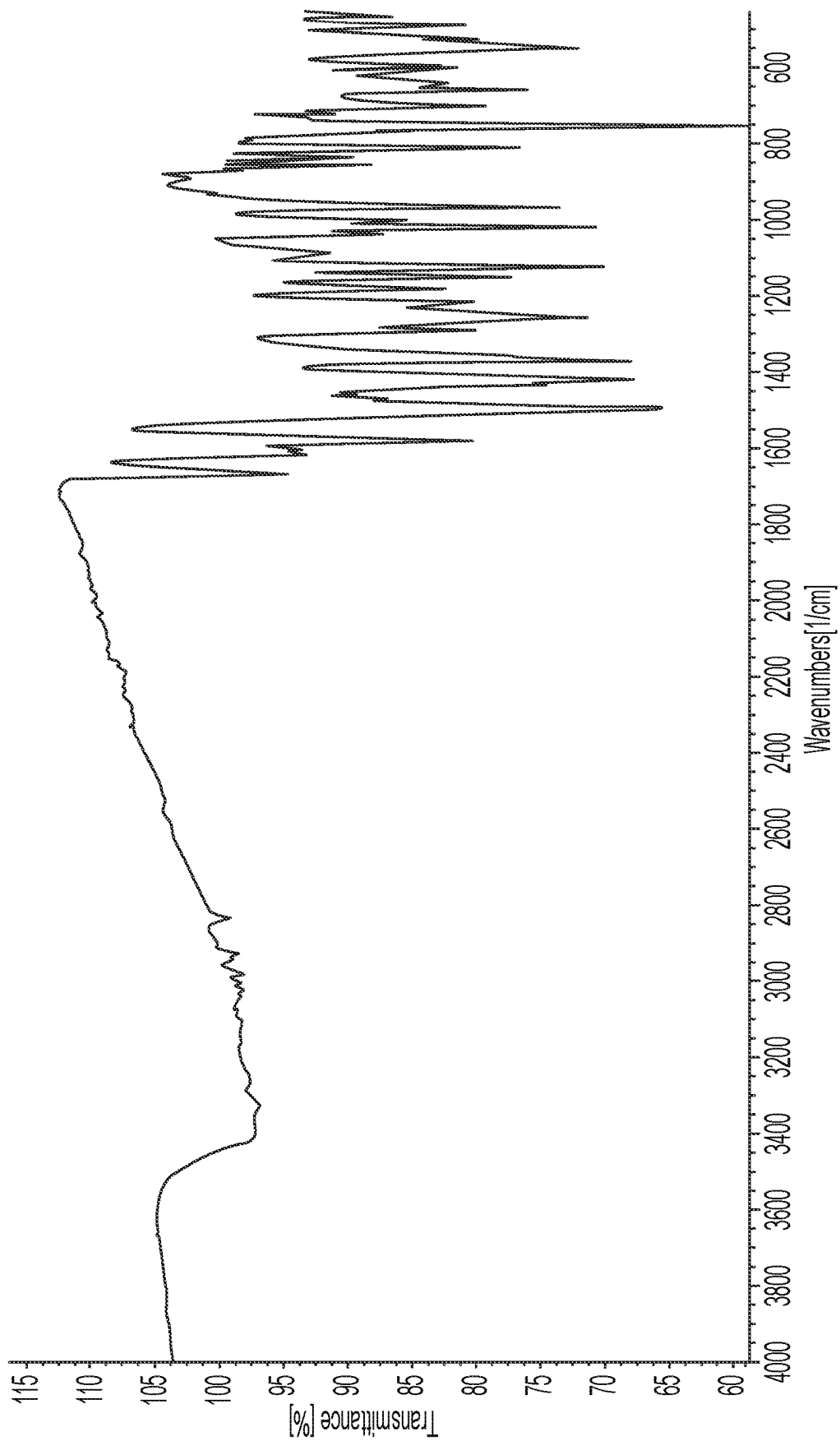
FIG. 29 depicts the Infrared Spectrum for the crystalline 1:1 Tranilast Potassium Monohydrate salt.

7.6 Infrared Spectrum of the Crystalline 1:1 Tranilast Potassium Monohydrate Salt The experimental Infrared Spectrum of the crystalline 1:1 tranilast potassium monohydrate salt is shown in FIG. 29. The significant peaks identified in the experimental infrared spectrum of FIG. 29 are 1670, 1583, 1497, 1422, 1370, 1292, 1259, 1222, 1184, 1155, 1127, 969, 812, 756, 702, 664, 645, 599, 547, 524 and 490 cm$^{-1}$±1 cm$^{-1}$. The entire list of peaks, or a subset thereof, may be sufficient to characterize the crystalline salt, as well as by an infrared pattern substantially similar to FIG. 29. For example, the crystalline 1:1 tranilast potassium monohydrate salt may be characterized by at least four peaks selected from the peaks at 1670, 1583, 1492, 1422, 1370, 1155 and 1127 cm$^{-1}$+1 cm$^{-1}$.

Example 8

Crystalline Tranilast Diethanolamine Salt 8.1 Preparation of the Crystalline 1:1 Tranilast Diethanolamine Salt Tranilast (150 mg) and diethanolamine (48 mg) were weighed into a glass vial. Methanol (2 ml) was added to the vial. The vial was sealed and shaken until all solid had dissolved. The vial lid was removed and solvent allowed to evaporate resulting in a colourless crystalline solid. The resulting colourless crystals were dried in a vacuum oven at 40° C. overnight.

Figure 30:
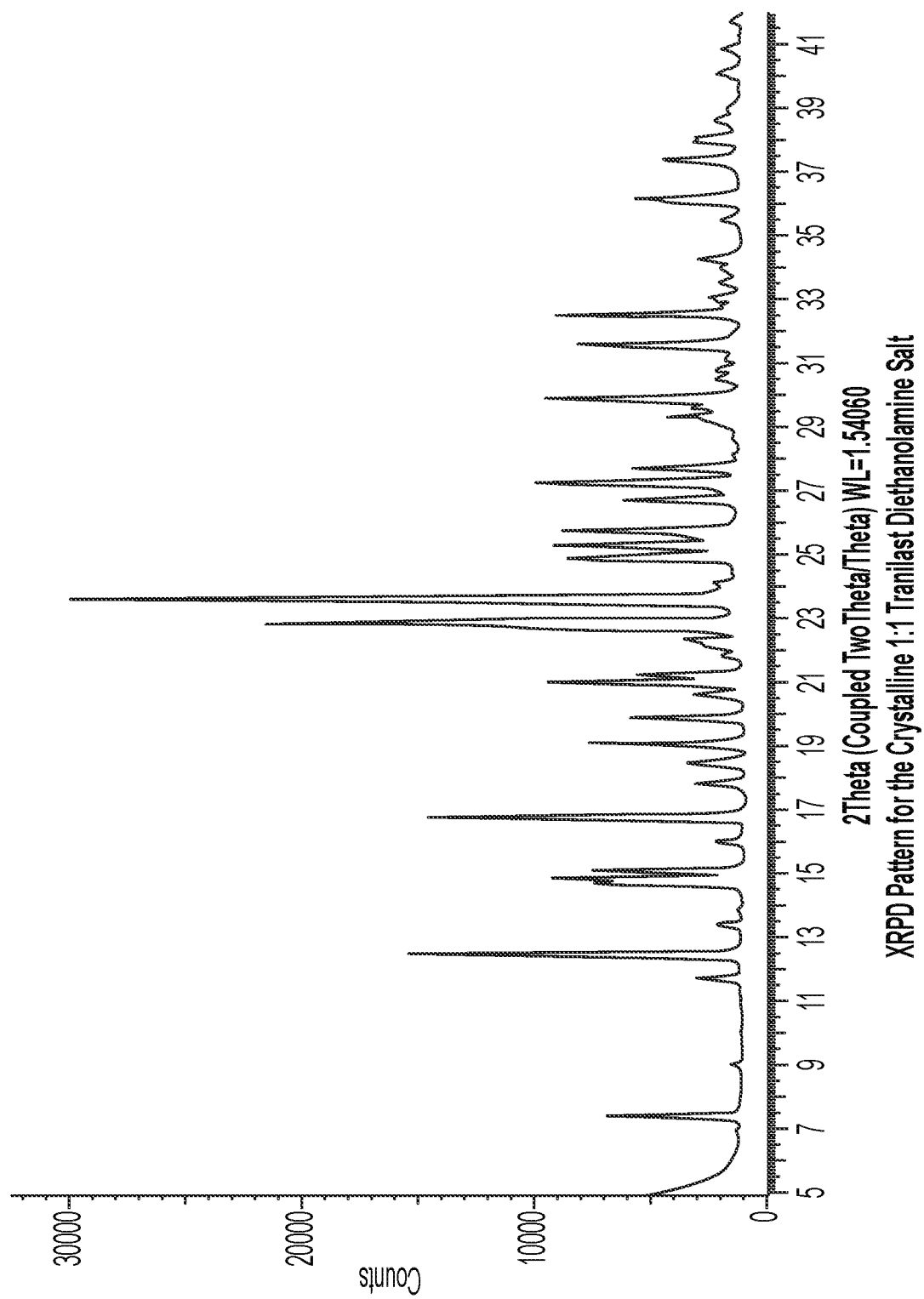
FIG. 30 depicts the XRPD Pattern for the crystalline 1:1 Tranilast Diethanolamine salt.

8.2 XRPD Characterisation of the Crystalline 1:1 Tranilast Diethanolamine Salt The experimental XRPD pattern of the crystalline 1:1 tranilast diethanolamine salt is shown in FIG. 30. Table 10 lists the angles, °2θ±0.2°2θ, and d value of the peaks identified in the experimental XRPD pattern of FIG. 30. The entire list of peaks or corresponding d values, or a subset thereof, may be sufficient to characterize the crystalline salt, as well as by an XRPD pattern substantially similar to FIG. 30. For example, the crystalline 1:1 tranilast diethanolamine salt may be characterized by at least four peaks selected from the peaks at 7.5, 11.8, 12.5, 16.8, 18.5, 19.1 and 19.9°2θ±0.2°2θ or their corresponding d values.

TABLE 10

| Angle °2θ ± 0.2 °2θ | d value Angstrom | Intensity % |
|---|---|---|
| 7.5 | 11.83 | 19.6% |
| 9.1 | 9.75 | 1.7% |
| 11.8 | 7.52 | 6.7% |
| 12.5 | 7.08 | 49.6% |
| 13.4 | 6.59 | 3.6% |
| 14.7 | 6.00 | 22.4% |
| 14.9 | 5.95 | 29.0% |
| 15.1 | 5.85 | 22.6% |
| 16.1 | 5.51 | 4.1% |
| 16.8 | 5.27 | 47.6% |
| 17.9 | 4.96 | 7.4% |
| 18.5 | 4.80 | 8.8% |
| 19.1 | 4.64 | 22.8% |
| 19.9 | 4.45 | 16.9% |
| 20.6 | 4.30 | 7.4% |
| 21.0 | 4.22 | 29.1% |
| 21.3 | 4.17 | 15.6% |
| 22.2 | 4.00 | 5.5% |
| 22.4 | 3.97 | 8.1% |
| 22.9 | 3.88 | 70.4% |
| 23.7 | 3.76 | 100.0% |
| 24.9 | 3.57 | 24.7% |
| 25.3 | 3.52 | 27.0% |
| 25.6 | 3.48 | 8.0% |
| 25.8 | 3.45 | 26.0% |
| 26.8 | 3.33 | 17.0% |
| 27.3 | 3.27 | 30.0% |
| 27.7 | 3.21 | 16.0% |
| 29.4 | 3.04 | 10.4% |
| 29.6 | 3.01 | 6.9% |
| 29.9 | 2.98 | 28.6% |
| 31.6 | 2.83 | 24.0% |
| 32.6 | 2.75 | 27.3% |
| 34.3 | 2.61 | 6.3% |
| 36.2 | 2.48 | 15.6% |
| 37.4 | 2.40 | 11.0% |
| 38.1 | 2.36 | 6.5% |

8.3 DSC of the Crystalline 1:1 Tranilast Diethanolamine Salt

Figure 31:
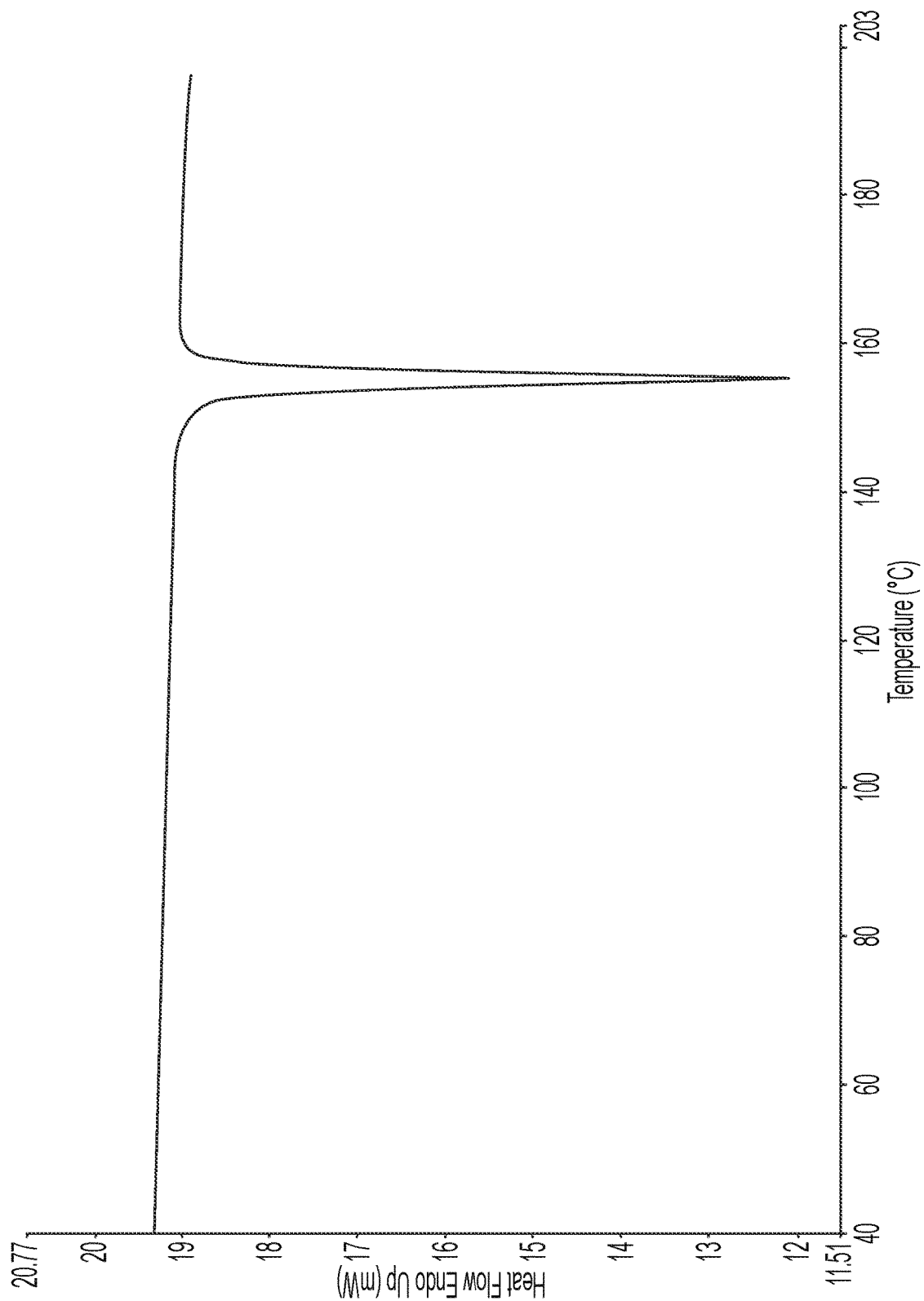
FIG. 31 depicts the DSC Trace for the crystalline 1:1 Tranilast Diethanolamine salt.

The differential scanning calorimetry (DSC) trace, FIG. 31, shows a single endotherm with peak maximum of 155.5° C.

8.4 TGA of Crystalline the 1:1 Tranilast Diethanolamine Salt

Figure 32:
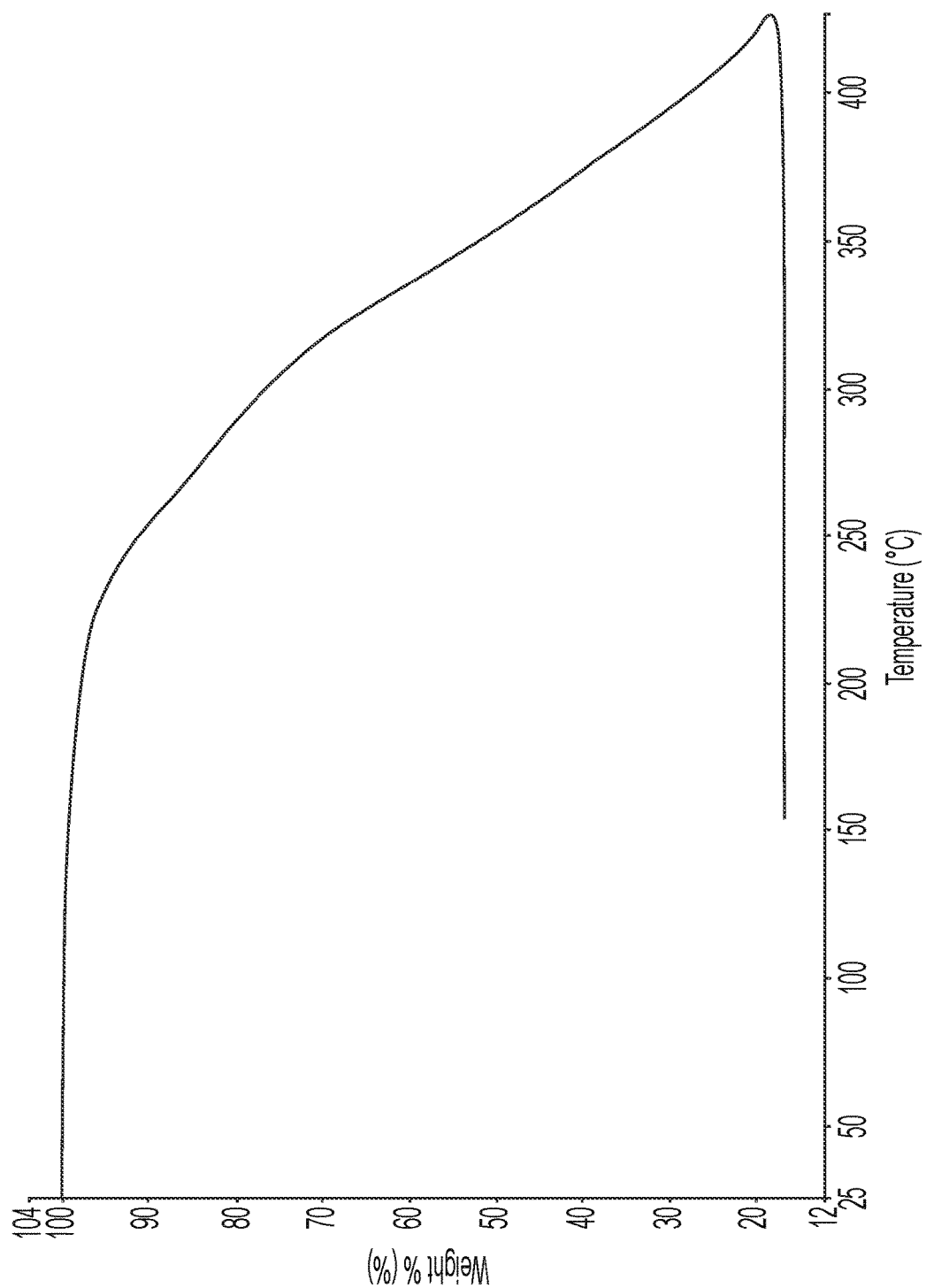
FIG. 32 depicts the TGA Trace for the crystalline 1:1 Tranilast Diethanolamine salt.

The thermal gravimetric analysis (TGA) trace, FIG. 32, shows significant weight loss begins at around 215° C.

8.5 Infrared Spectrum of Crystalline the 1:1 Tranilast Diethanolamine Salt

Figure 33:
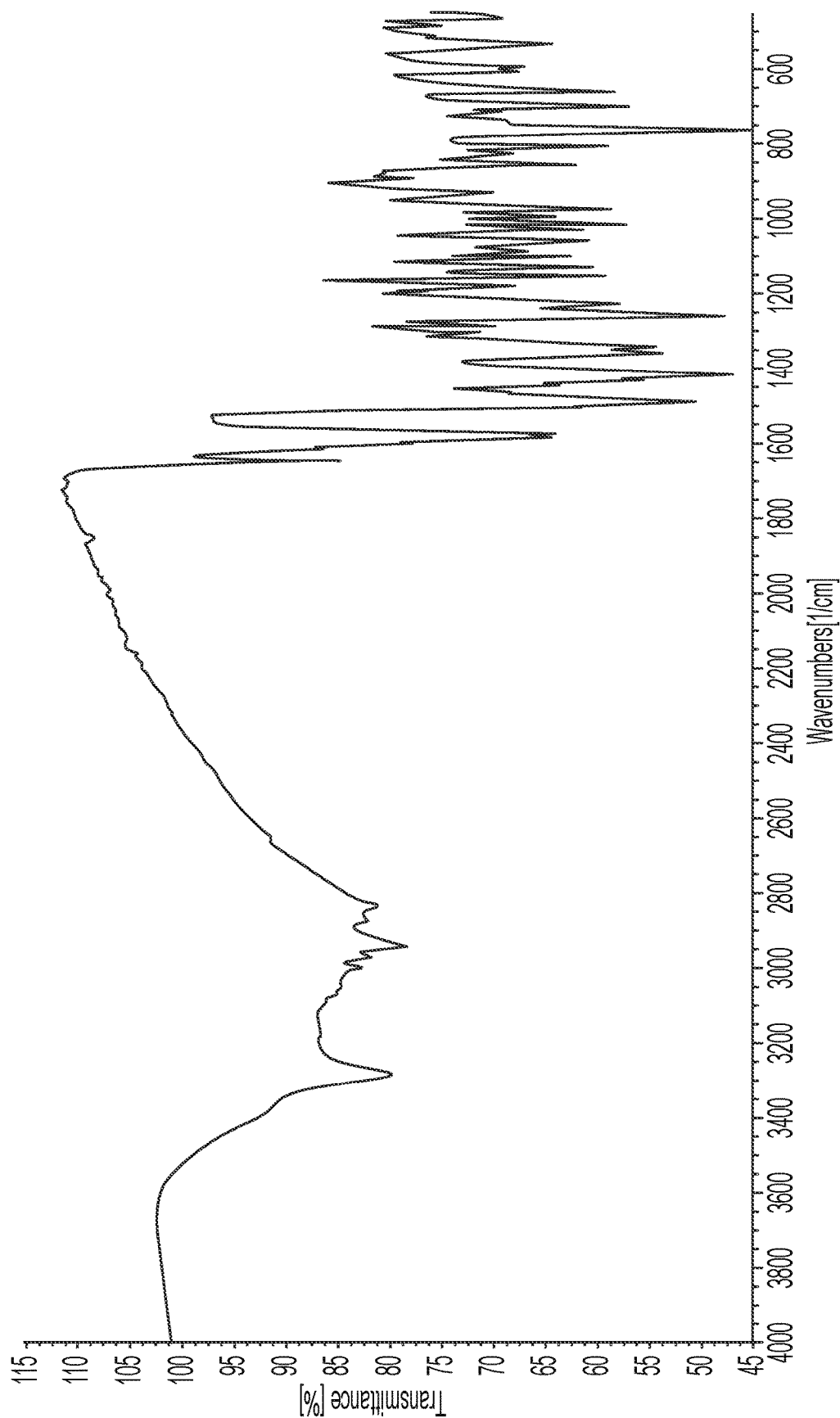
FIG. 33 depicts the Infrared Spectrum for the crystalline 1:1 Tranilast Diethanolamine salt.

The experimental Infrared Spectrum of the crystalline 1:1 tranilast diethanolamine salt is shown in FIG. 33. The significant peaks identified in the experimental infrared spectrum of FIG. 33 are 3289, 2947, 1652, 1580, 1494, 1422, 1363, 1346, 1266, 1233, 1186, 1159, 1137, 1109, 1090, 1067, 1035, 1015, 999, 981, 935, 857, 831, 812, 770, 721, 704, 663, 612, 601, 540 and 468 cm$^{-1}$±1 cm$^{-1}$. The entire list of peaks, or a subset thereof, may be sufficient to characterize the crystalline salt, as well as by an infrared pattern substantially similar to FIG. 33. For example, the crystalline 1:1 tranilast diethanolamine salt may be characterized by at least four peaks selected from the peaks at 1652, 1494, 1422, 1363, 1346, 1266 and 1233 cm$^{-1}$±1 cm$^{-1}$.

Example 9

Crystalline Tranilast Ethanolamine Salt

9.1 Preparation of the Crystalline 1:1 Tranilast Ethanolamine Salt

Tranilast (150 mg) and ethanolamine (28 mg) were weighed into a glass vial. Methanol (2 ml) was added to the vial. The vial was sealed and shaken until all solid had dissolved. The vial lid was removed and solvent allowed to evaporate resulting in a colourless crystalline solid. The resulting colourless crystals were dried in a vacuum oven at 40° C. overnight.

Figure 34:
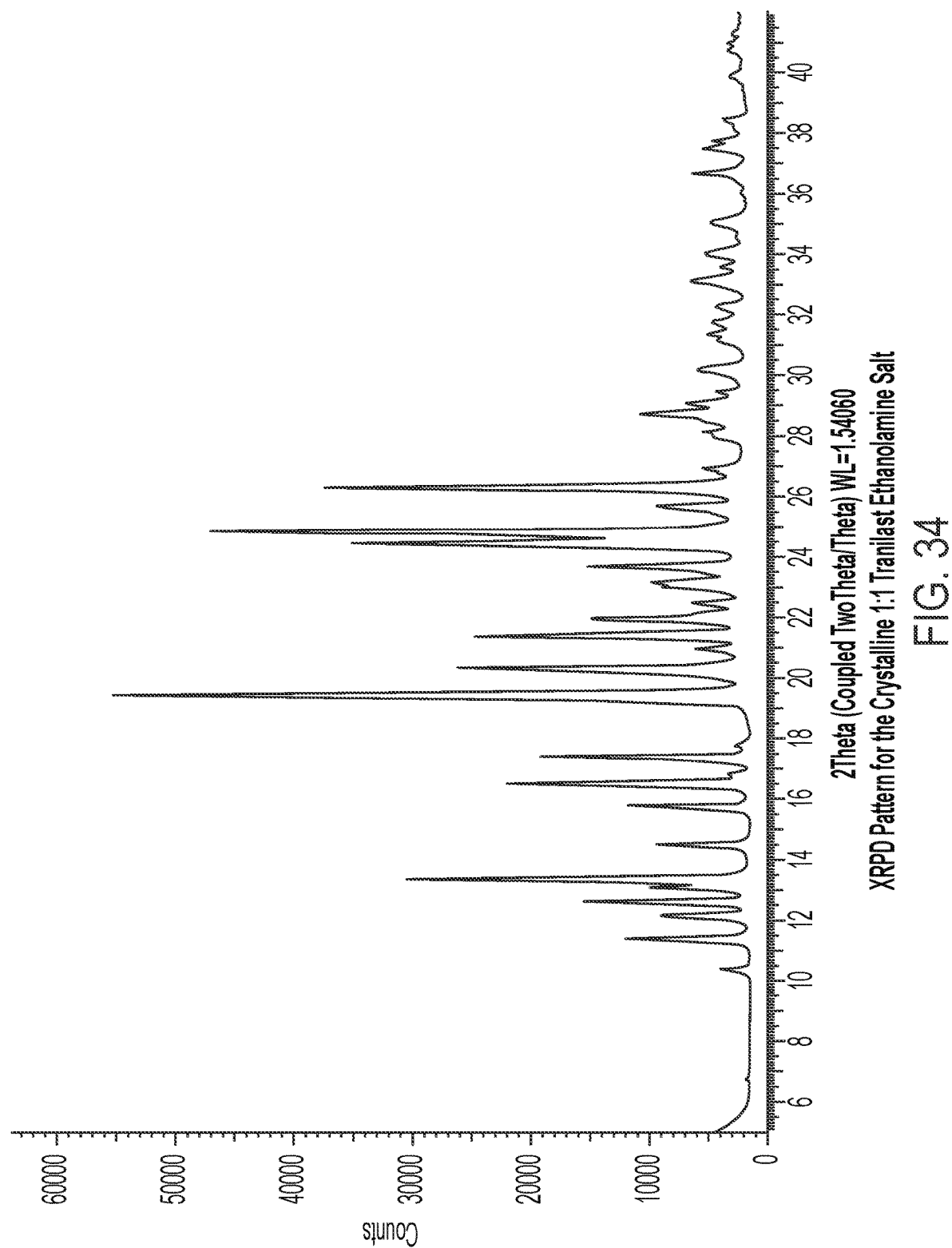
FIG. 34 depicts the XRPD Pattern for the crystalline 1:1 Tranilast Ethanolamine salt.

9.2 XRPD Characterisation of the Crystalline 1:1 Tranilast Ethanolamine Salt The experimental XRPD pattern of the crystalline 1:1 tranilast ethanolamine salt is shown in FIG. 34. Table 11 lists the angles, °2θ±0.2°2θ, and d value of the peaks identified in the experimental XRPD pattern of FIG. 34. The entire list of peaks or their corresponding d values, or a subset thereof, may be sufficient to characterize the crystalline salt, as well as by an XRPD pattern substantially similar to FIG. 34. For example, the crystalline 1:1 tranilast ethanolamine salt may be characterized by at least four peaks selected from peaks at 10.4, 11.4, 12.2, 14.5, 15.8, 19.5 and 20.4°2θ±0.2°2θ or their corresponding d values.

TABLE 11

| Angle °2θ ± 0.2 °2θ | d value Angstrom | Intensity % |
|---|---|---|
| 6.8 | 13.00 | 0.6% |
| 10.4 | 8.50 | 4.7% |
| 11.4 | 7.70 | 19.6% |
| 12.2 | 7.30 | 13.7% |
| 12.7 | 7.00 | 26.0% |
| 13.1 | 6.70 | 15.6% |
| 13.4 | 6.60 | 53.8% |
| 14.5 | 6.10 | 14.4% |
| 15.8 | 5.60 | 19.2% |
| 16.6 | 5.30 | 38.0% |
| 17.4 | 5.10 | 33.1% |
| 19.5 | 4.60 | 100.0% |
| 20.4 | 4.40 | 45.0% |
| 21.0 | 4.20 | 6.8% |
| 21.4 | 4.10 | 41.7% |
| 22.0 | 4.00 | 23.1% |
| 22.5 | 3.90 | 7.0% |
| 23.2 | 3.80 | 13.2% |
| 23.7 | 3.70 | 23.5% |
| 24.5 | 3.60 | 61.0% |
| 24.9 | 3.60 | 82.9% |
| 25.7 | 3.50 | 12.8% |
| 26.3 | 3.40 | 65.8% |
| 26.9 | 3.30 | 5.7% |
| 28.2 | 3.20 | 6.0% |
| 28.5 | 3.10 | 6.1% |
| 28.8 | 3.10 | 15.9% |
| 29.1 | 3.10 | 8.7% |
| 30.2 | 3.00 | 6.7% |
| 31.4 | 2.80 | 5.5% |
| 31.7 | 2.80 | 5.1% |
| 33.1 | 2.70 | 8.4% |
| 34.0 | 2.60 | 6.2% |

TABLE 11-continued

| Angle °2θ ± 0.2 °2θ | d value Angstrom | Intensity % |
|---|---|---|
| 35.1 | 2.60 | 5.7% |
| 36.7 | 2.40 | 8.5% |

9.3 SCXRD Characterisation of 1:1 Tranilast Ethanolamine Salt

Figure 35:
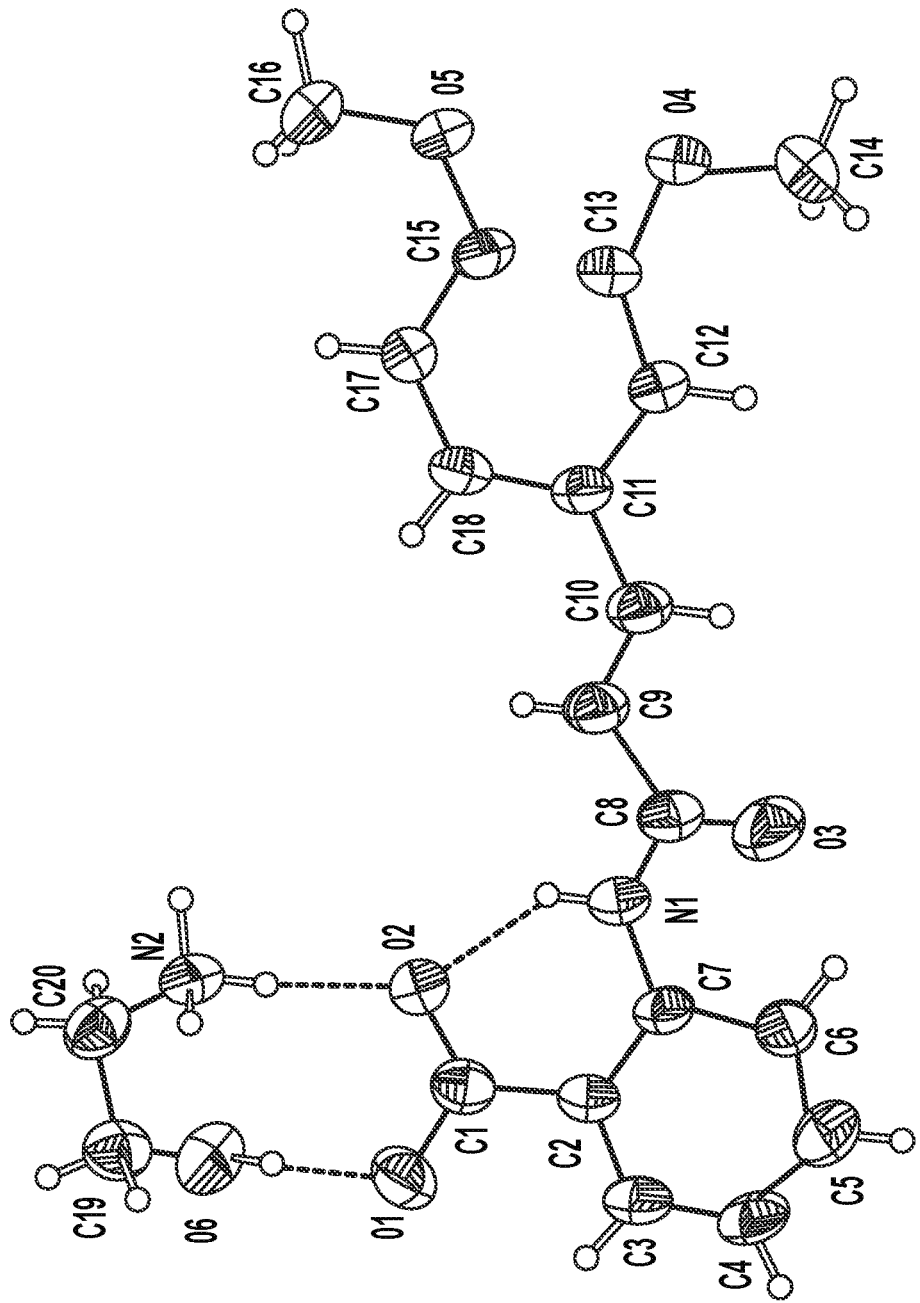
FIG. 35 depicts the ORTEP drawing of the crystalline 1:1 Tranilast Ethanolamine salt.
Figure 36:
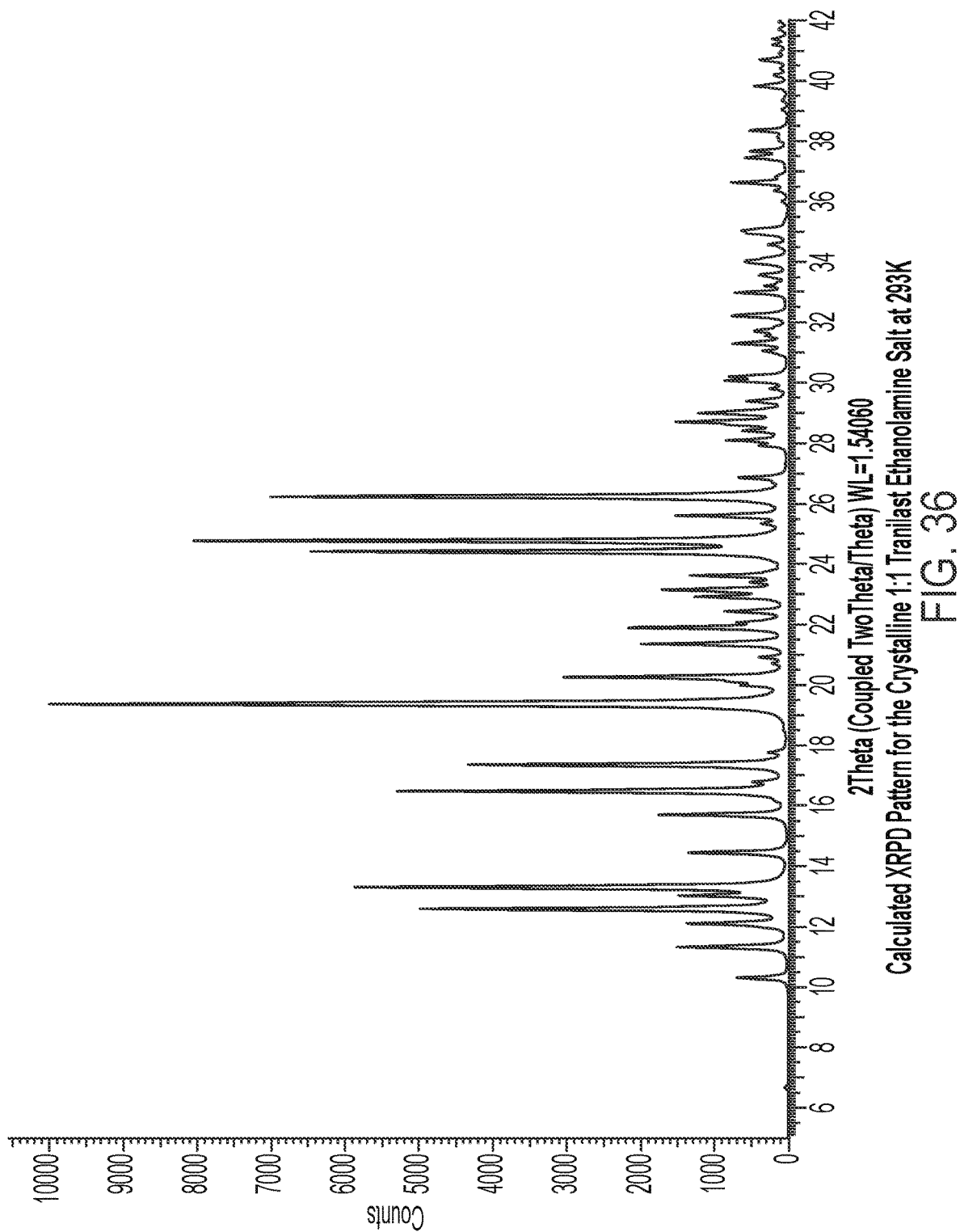
FIG. 36 depicts the calculated XRPD Pattern for the crystalline 1:1 Tranilast Ethanolamine salt at 293K.

The crystal used for single crystal structure determination was selected from the batch of crystals prepared as described above. The single crystal data and structure refinement parameters are reported in Table 12, below. FIG. 35 shows an ORTEP drawing of the asymmetric unit from the crystal structure of the 1:1 tranilast ethanolamine salt showing the atom numbering scheme employed. Anisotropic atomic displacement ellipsoids for the non-hydrogen atoms are shown at the 50% probability level and hydrogen atoms are displayed as spheres of arbitrary radius. The calculated XRPD pattern based on the single crystal data and structure for the 1:1 tranilast ethanolamine salt at 293 K is shown in FIG. 36. It is can be seen that in this case there is good agreement between the experimental XRPD pattern collected at room temperature (FIG. 34) and the calculated XRPD pattern is derived from data collected at 293 K. There are small intensity differences owing to preferred orientation effects present in the experimental pattern.

TABLE 12

| | |
|---|---|
| Molecular formula | $C_{20}H_{24}N_2O_6$ |
| Molecular weight | 388.41 |
| Crystal System | Monoclinic |
| Space Group | P21/c |
| Unit Cell Dimensions | a = 13.24000(17) Å |
| | b = 8.75556(13) Å |
| | c = 17.1562(2) Å |
| | α = 90.00° |
| | β = 93.0111(12)° |
| | ɣ = 90.00° |
| Cell Volume | 1986.07(5) Å³ |
| Z | 4 |
| Temperature | 293(1) K |
| Radiation Wavelength/type | 1.54184 Å/CuKα |
| Goodness of fit | 1.039 |
| R factor | 0.0372 |
| Morphology | Colourless prism |

9.4 DSC of the Crystalline 1:1 Tranilast Ethanolamine Salt

Figure 37:
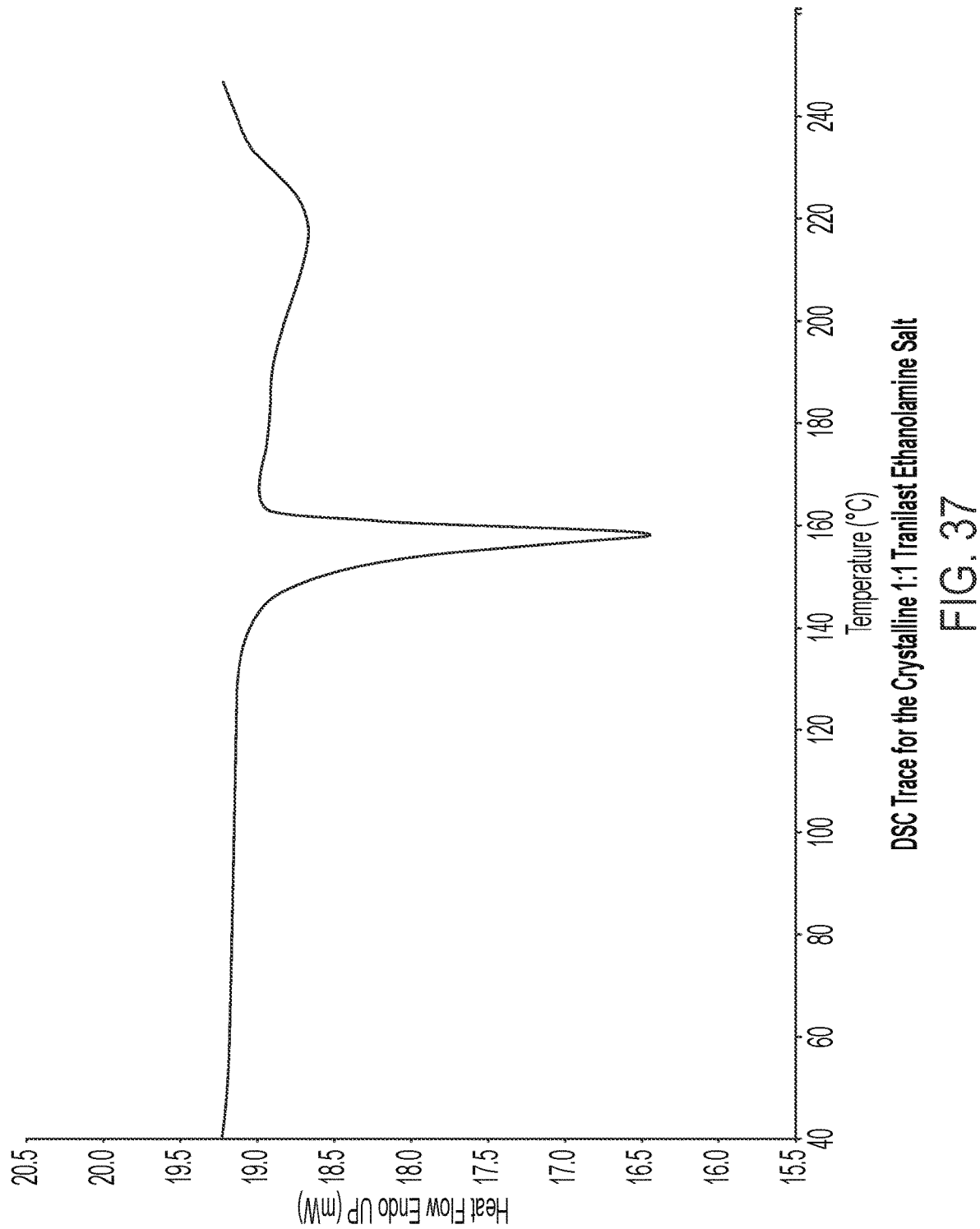
FIG. 37 depicts the DSC Trace for the crystalline 1:1 Tranilast Ethanolamine salt.

The differential scanning calorimetry (DSC) trace, FIG. 37, shows a sharp endotherm with a peak maximum of 158.3° C.

9.5 TGA of Crystalline the 1:1 Tranilast Ethanolamine Salt

Figure 38:
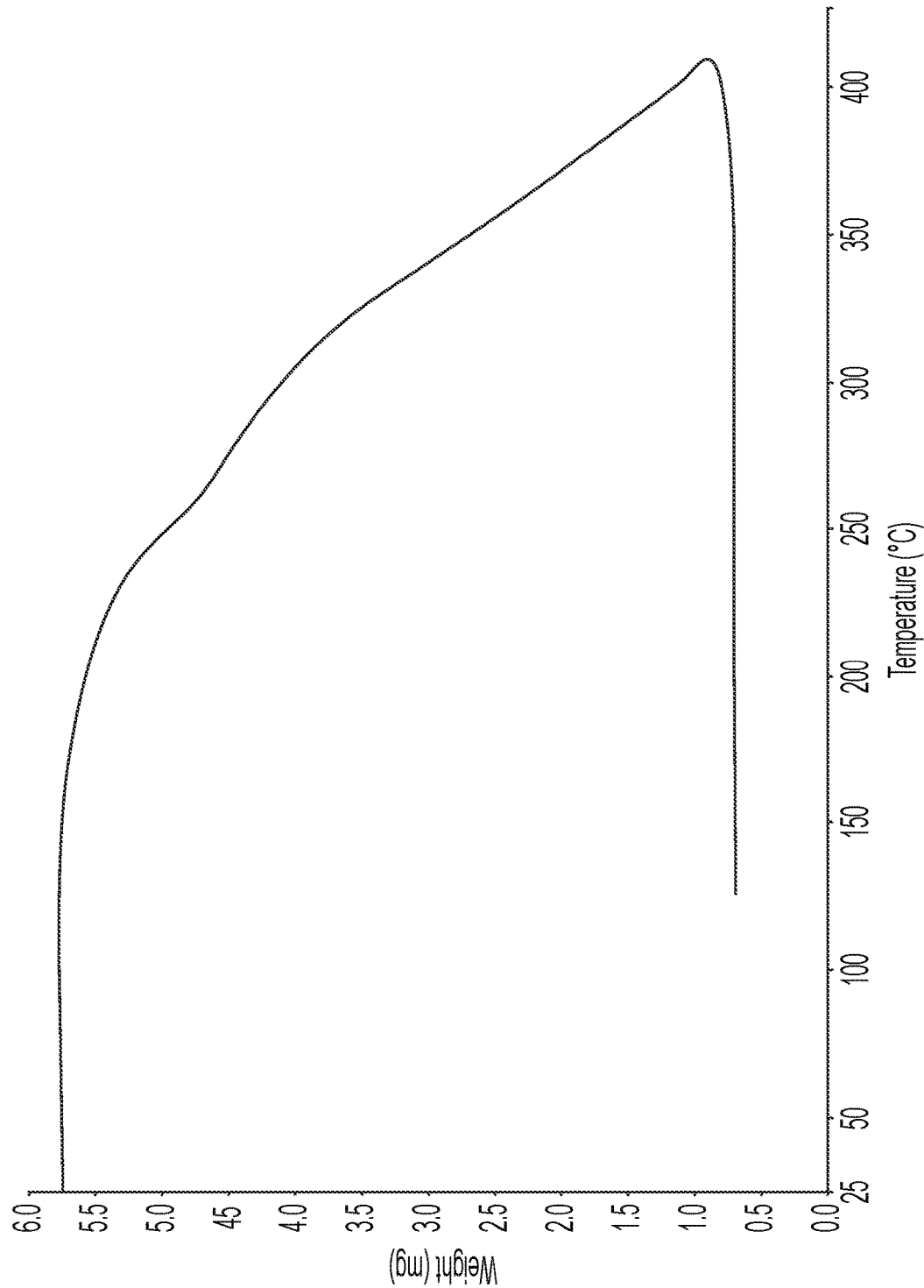
FIG. 38 depicts the TGA Trace for the crystalline 1:1 Tranilast Ethanolamine salt.

The thermal gravimetric analysis (TGA) trace, FIG. 38, shows no significant weight loss prior to 160° C.

9.6 Infrared Spectrum of Crystalline the 1:1 Tranilast Ethanolamine Salt

Figure 39:
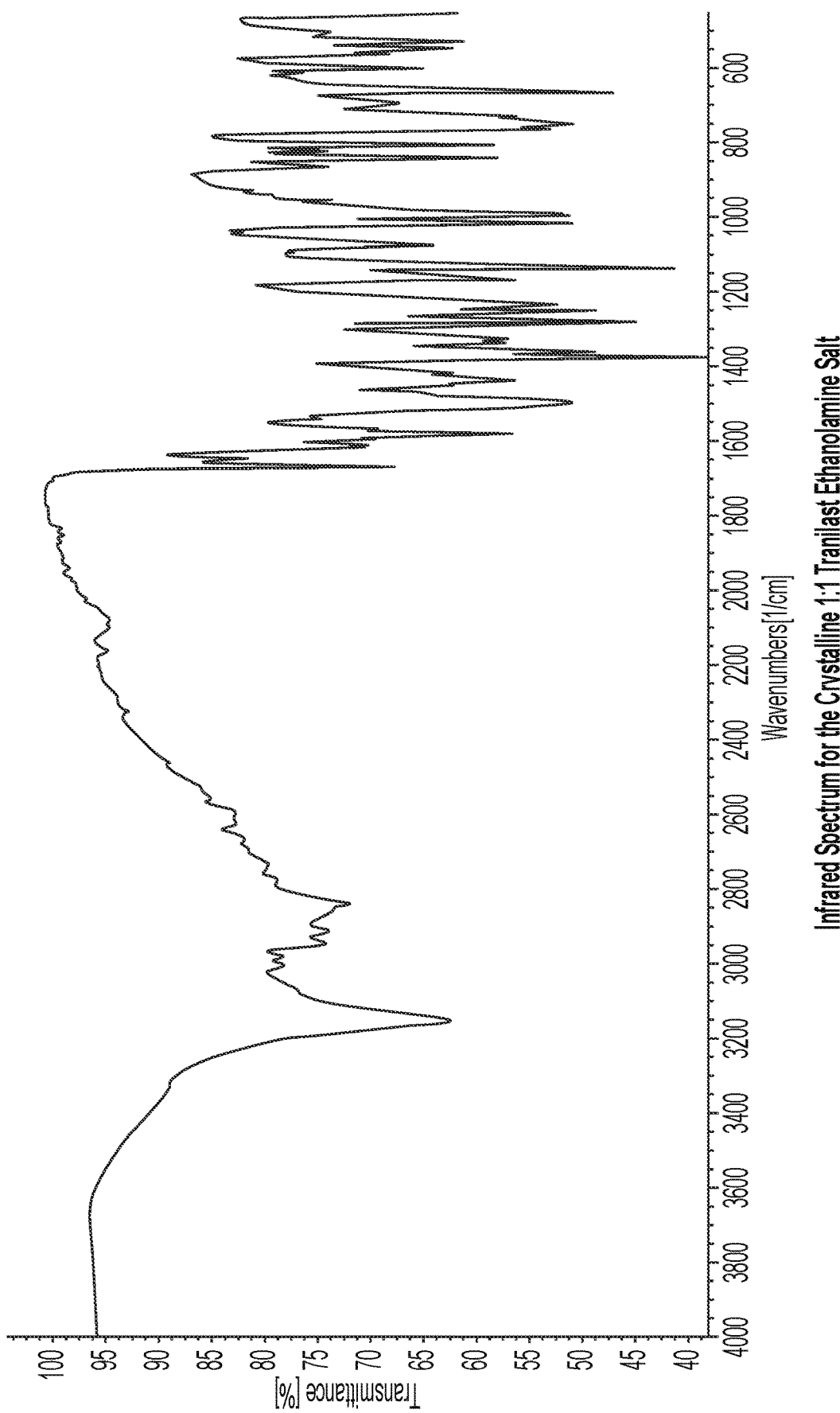
FIG. 39 depicts the Infrared Spectrum for the crystalline 1:1 Tranilast Ethanolamine salt.

The experimental Infrared Spectrum of the crystalline 1:1 tranilast N-methylglucamine Form I salt is shown in FIG. 39. The significant peaks identified in the experimental infrared spectrum of FIG. 39 are 3154, 1668, 1611, 1585, 1496, 1438, 1375, 1359, 1336, 1323, 1293, 1277, 1255, 1232, 1161, 1131, 1072, 1017, 997, 955, 842, 806, 765, 750, 692, 664, 599, 549 and $527^{cm-1} \pm 1^{cm-1}$. The entire list of peaks, or a subset thereof, may be sufficient to characterize the crystalline salt, as well as by an infrared pattern substantially similar to FIG. 39. For example, the crystalline 1:1 tranilast ethanolamine salt may be characterized by at least four peaks selected from the peaks at 1668, 1585, 1375, 1359, 1277, 1255 and $1131^{cm-1} \pm 1^{cm-1}$.

Example 10

Solid-State Accelerated Stability Study

A study was carried out to examine the physical stability of the 1:1 crystalline tranilast salts with respect to solid form conversion or deliquescence over time under accelerated conditions. 50 mg each of the crystalline 1:1 tranilast L-lysine salt, crystalline 1:1 tranilast N-ethylglucamine salt, crystalline 1:1 tranilast potassium monohydrate, crystalline 1:1 tranilast diethylamine salt, crystalline 1:1 tranilast diethanolamine salt and crystalline 1:1 tranilast ethanolamine salt were separately placed in a sealed container at 40° C. and 75% relative humidity and stored under these conditions for 7 days. After this time all samples remained as solids with no signs of deliquescence. Each sample was analysed by XRPD to observe any potential form changes. XRPD analysis showed that all the samples retained their original crystalline form and that none of the crystalline tranilast salts of this invention undergo solid form conversion under these conditions.

Example 11

Solution Photostability Study

It is known that tranilast is photochemically unstable once dissolved in solution, transforming into cis-isomer and dimer forms upon UV exposure (N. Hori, *Chem Pharm Bull.* 1999; 47: 1713-1716). It was therefore decided to explore the photo-stability of the 1:1 tranilast N-methylglucamine form II salt, 1:1 tranilast N-ethylglucamine salt, 1:1 tranilast L-lysine salt and 1:1 tranilast diethylamine salt once dissolved in solution to see if these forms would also show signs of solution degradation. A 2 mg sample of the four salt forms under investigation were each weighed into a clear glass vial. Each sample was dissolved in water (1 ml). The vials were placed into a Vindon Scientific Photostability cabinet and irradiated with UV light (average Klux=13.9 (13.9 Lux/hour), average UV watts/m²/hour=27.7, average temperature=26.8° C.).The percentage of tranilast remaining in each sample, that had not undergone degradation into the cis-isomer, dimer or any other degradation product, was determined at 2, 6 and 24 hours using HPLC. The HPLC method used is described in Table 13. The results of this study are shown in Table 14.

TABLE 13

| | | | |
|---|---|---|---|
| Mobile Phase A | Water:TFA (100:0.03) | | |
| Mobile Phase B | Acetonitrile:TFA (100:0.03) | | |
| Column | Acquity BEH Phenyl 30 × 4.6 mm, 1.7 μm particle size | | |
| Column Temperature | 40° C. | | |
| Flow Rate | 2.0 ml/min | | |
| Injection Volume | 5 μl | | |
| Wavelength | 338 nm | | |
| Post run time | 2.3 minutes | | |
| Gradient Program | Time (min) | % A | % B |
| | 0 | 95 | 5 |
| | 5.2 | 5 | 95 |

TABLE 13-continued

| 5.7 | 5 | 95 |
| 5.8 | 95 | 25 |
| 6.2 | 95 | 5 |

TABLE 14

| Tranilast salt | % tranilast remaining after UV exposure | | |
| --- | --- | --- | --- |
| | 2 hrs | 6 hrs | 24 hrs |
| L-Lysine | 92.53 | 55.98 | 21.03 |
| N-methylglucamine Form II | 90.51 | 54.80 | 22.09 |
| Diethylamine | 92.06 | 52.30 | 20.72 |
| N-ethylglucamine | 84.13 | 58.20 | 35.90 |

It can be seen from Table 13 that even after 2 hours all four tranilast salts had begun to show signs of degradation with only low levels of tranilast remaining in each solution after 24 hours. These results confirm that these tranilast salts would not be suitable for storage in solution.

Example 12

Solid-State Photostability Study

It is known that while pure crystalline tranilast is photostable in the solid form, some other solid forms of the API are not as photostable (S. Onoue, *Eur J Pharm Sci.* 2010; 39: 256-262). A study was, therefore, carried out to determine the solid-state photostability of the crystalline 1:1 N-methylglucamine form II salt, crystalline 1:1 tranilast N-ethylglucamine salt, crystalline 1:1 tranilast L-lysine salt and the crystalline 1:1 tranilast diethylamine salt to see if these would remain photostable during storage in their solid form. A 6-10 mg sample of each of the tranilast forms under investigation was spread over the bottom surface of a clear glass vial. The vials were placed into a Vindon Scientific Photostability cabinet and irradiated with UV light (average Klux=18.2 (18.2 Lux/hour), average UV values=2.55 watts/minute, temperature=31.0-32.0° C.).The percentage of tranilast remaining in each sample, that had not undergone degradation into the cis-isomer, dimer or any other degradation product, was determined at 2, 6 and 24 hours using HPLC. The HPLC method used is described in Table 13. The results of this study are shown in Table 15. It can be seen from Table 15 that in the solid-state crystalline 1:1 N-methylglucamine form II, crystalline 1:1 tranilast N-diethylglucamine, crystalline 1:1 tranilast L-lysine and crystalline 1:1 tranilast diethylamine are all photostable under these conditions, with no indication of any photodegradation. These combined results suggest that whilst storage of these tranilast salts in solution would result insignificant photo-degradation, storage in their crystalline form should present no photostability problems.

TABLE 15

| Tranilast Salt | % tranilast remaining after UV exposure | | |
| --- | --- | --- | --- |
| | 2 hrs | 6 hrs | 24 hrs |
| L-Lysine | 99.35 | 99.53 | 99.54 |
| N-methylglucamine Form II | 99.50 | 99.58 | 99.51 |
| Diethylamine | 99.57 | 99.61 | 99.63 |
| N-ethylglucamine | 99.55 | 99.61 | 99.47 |

Example 13

Aqueous Solubility Study

Tranilast is practically insoluble in water (14.5 µg/ml) (Society of Japanese Pharmacopoeia. 2002) and U.S. Pat. No. 5,356,620 states that pharmaceutically acceptable salts of tranilast are too insoluble in water to prepare an aqueous solution. Also as the only pharmaceutically acceptable salt of tranilast described previously in the literature is the tranilast sodium salt (N Geng, *Cryst. Growth Des.* 2013; 13: 3546-3553), and the authors of this publication describe how this salt has a lower apparent solubility than pure tranilast, it is not possible to predict whether the new crystalline salt forms of tranilast disclosed in this application would have aqueous solubilities higher or lower than that of crystalline tranilast. A study was, therefore, carried out to determine the aqueous solubility of the crystalline 1:1 N-methylglucamine form I salt, crystalline 1:1 N-methylglucamine form II salt, crystalline 1:1 tranilast N-ethylglucamine salt, crystalline 1:1 tranilast L-lysine salt, crystalline 1:1 tranilast potassium monohydrate salt, crystalline 1:1 tranilast diethylamine salt, crystalline 1:1 tranilast diethanolamine salt and crystalline 1:1 tranilast ethanolamine salt in water. Water (0.5 ml, pH7.0) was added to increasing quantities of each salt and the resulting slurries shaken at 25° C. If all solid was seen to dissolve a further small aliquot of the relevant salt was added until the point at which after shaking for one hour solid particles still remained undissolved. The slurries were shaken for 24 hours to check that saturation point had been reached. After total addition of 500 mg of forms I or II of the crystalline 1:1 tranilast N-methylglucamine salts saturation point was still not reached, therefore, these solutions were allowed to stand for 24 hours to see if any precipitation would occur. After 24 hours both 1:1 tranilast N-methylglucamine forms I and II still remained in solution so it can be understood that both polymorphs of 1:1 tranilast N-methylamine salt have an aqueous solubility greater than 1000 mg/ml. The 1:1 tranilast N-ethylglucamine, 1:1 tranilast L-lysine, 1:1 tranilast potassium monohydrate, 1:1 tranilast diethylamine, 1:1 tranilast diethanolamine and 1:1 tranilast ethanolamine all remained as suspensions after 24 hours. Table 16 shows the results of the solubility study in terms of the mass of tranilast dissolved. It can be seen that all 1:1 crystalline salts of this invention are more soluble than pure tranilast. It can also be seen that there is a large variation in the solubility of the salts examined with the 1:1 tranilast diethylamine salt only showing a solubility of 18-20 mg/ml whilst both polymorphs I and II of 1:1 tranilast N-methylglucamine demonstrated a solubility >626 mg/ml.

TABLE 16

| Tranilast Salt | Solubility (mg/ml) |
| --- | --- |
| N-methylglucamine Form I | >626 |
| N-methylglucamine Form II | >626 |
| L-Lysine | 277-283 |
| Potassium Monohydrate | 67-68 |
| Diethylamine | 18-20 |
| N-ethylglucamine | 232-238 |
| Diethanolamine | 431-439 |
| Ethanolamine | 396-404 |
| Tranilast Free Acid (Comparative) | 0.0145 |

Given the surprisingly high aqueous solubility's of a number of the crystalline tranilast salts of this invention it can be anticipated that a number of these salt forms could be used to prepare instant high dose liquid formulations of tranilast for in-situ delivery to patients.

Example 14

Dissolution Studies

For BCS class II drugs, such as tranilast, the rate of dissolution of the drug form used in the gastrointestinal media can be the controlling factor in the overall absorption and thus the bioavailability of an oral drug. This becomes even more influential as the dose of a drug increases. For conditions such as fibrosis or cancer where a higher dose of tranilast may be needed for successful treatment, finding a form of tranilast that has a high dissolution rate is important. A study was, therefore, carried out to examine the rate of dissolution of the crystalline 1:1 tranilast N-methylglucamine form II salt, crystalline 1:1 tranilast N-ethylglucamine salt, crystalline 1:1 tranilast L-lysine salt, crystalline 1:1 tranilast potassium monohydrate salt, 1:1 tranilast diethylamine salt, 1:1 tranilast diethanolamine salt and 1:1 tranilast ethanolamine salt compared with the marketed form of tranilast (Rizaben®), the crystalline 1:1 tranilast nicotinamide cocrystal of U.S. Pat. No. 9,512,064 B2 and the published crystalline 1:1 tranilast sodium salt. The dissolution study was carried out using 50 ml simulated intestinal fluid (FaSSIF V2) at pH 6.5 (37° C.) using a quantity of each tranilast form equivalent to 200 mg tranilast. The dissolution study was carried out using the Pion inForm® instrument. Detection and quantification of tranilast was performed by in-situ UV-spectroscopy using a fibre-optic probe, allowing instantaneous data collection from the point of sample introduction. UV absorption data was converted to mg/ml (±0.2 mg/ml) using a previously determined pH dependant molar extinction coefficients to quantitate the amount of dissolved drug.

Figure 40:
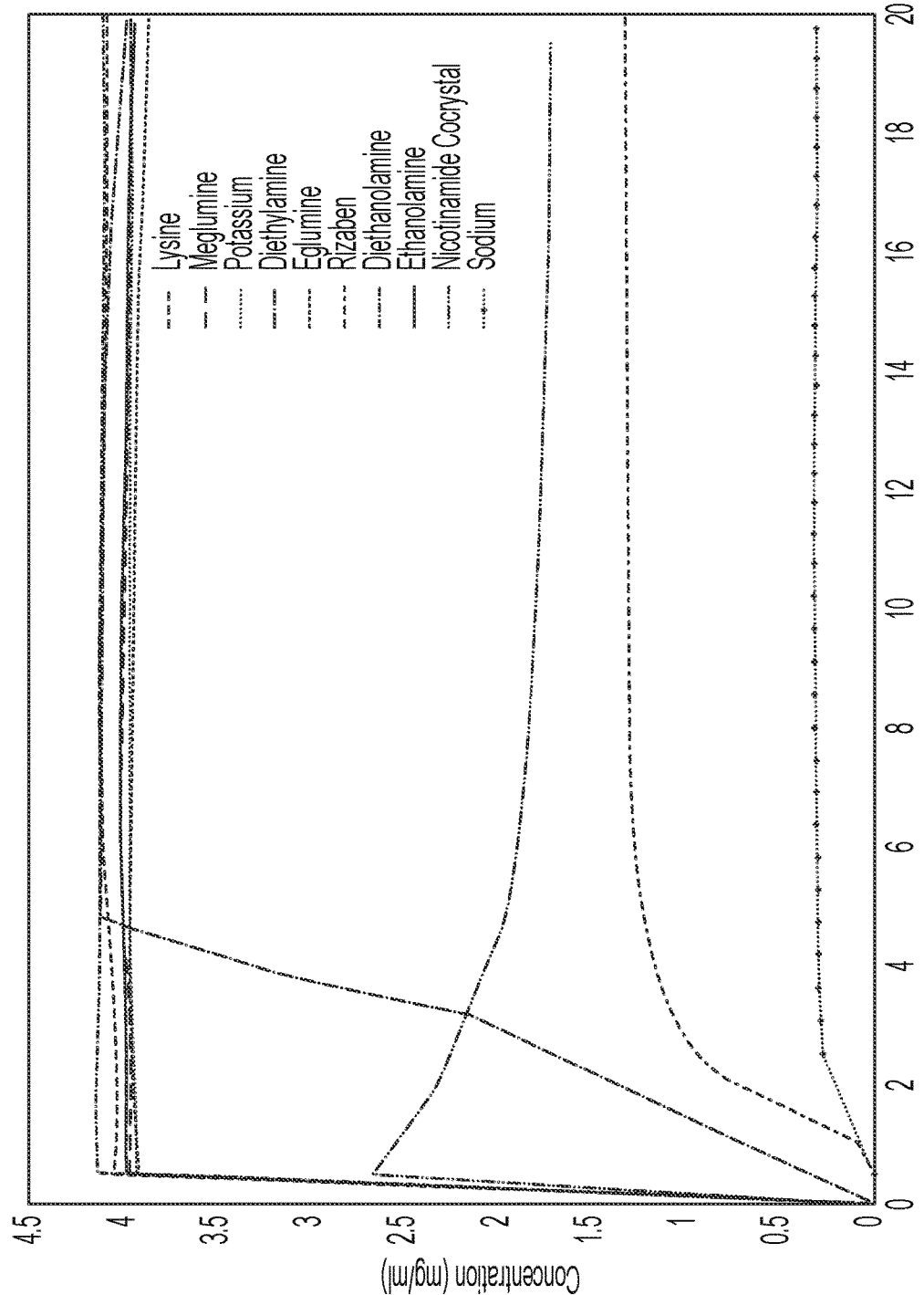
FIG. 40 depicts the dissolution profiles for the crystalline 1:1 tranilast salts, crystalline 1:1 tranilast nicotinamide cocrystal and Rizaben® in FaSSIF (V2) at 37° C.

The results of the study are shown in FIG. 40. It can be seen that the crystalline 1:1 tranilast N-methylglucamine form II salt, crystalline 1:1 tranilast N-ethylglucamine salt, crystalline 1:1 tranilast L-lysine salt, crystalline 1:1 tranilast potassium monohydrate salt, crystalline 1:1 tranilast diethanolamine salt and crystalline 1:1 tranilast ethanolamine salt achieve complete dissolution within 30 seconds suggesting almost instantaneous dissolution in this bio-relevant media, with this high solubility being maintained over a 20 minute period. Whereas six of the new crystalline 1:1 tranilast salt forms have completely dissolved within 30 seconds, the current marketed form of tranilast (Rizaben®) has only reached a solubility of 0.3 µg/ml in this timeframe. After 20 minutes Rizaben® has still only reached a solubility of 1.3 mg/ml in this media showing how greatly improved the dissolution rates of the new crystalline tranilast salts are compared to the current marketed form. The previously published crystalline 1:1 tranilast sodium salt only reached a solubility of $6.9 \times 10^{-16}$ mg/ml after 30 seconds and after 20 minutes still only showed a solubility of 0.3 mg/ml. As the crystalline 1:1 tranilast sodium salt had an even lower dissolution rate and solubility in biorelevant media than the currently marketed product Rizaben (based on pure crystalline tranilast), the significant improvement in dissolution rates of the new crystalline salts of this invention was unexpected. The greatly improved dissolution rates of these new crystalline tranilast salts could conceivably translate into improved absorption and bioavailability of oral tranilast, even at higher doses, potentially leading to reduced variability in patient drug plasma levels.

U.S. Pat. No. 9,512,064 B2 discloses various tranilast cocrystals, including a 1:1 tranilast nicotinamide cocrystal. As shown in the dissolution study in Example 10 and FIG. 32 of U.S. Pat. No. 9,512,064 B2, the 1:1 nicotinamide cocrystal had the best dissolution profile of the disclosed cocrystals, all of which were better than crystalline tranilast. The crystalline 1:1 tranilast nicotinamide cocrystal was, therefore, chosen in this dissolution study as a comparison to the crystalline salts of this invention. It can be seen from FIG. 40. that although the 1:1 tranilast nicotinamide cocrystal reaches a maximum solubility of 2.7 mg/ml within 30 seconds, precipitation rapidly occurs with the solubility falling to 1.95 mg/ml after 5 minutes and then further to 1.7 mg/ml over the 20 minute period. Whilst this 1:1 tranilast nicotinamide cocrystal shows an improved dissolution rate compared to Rizaben® over the first few minutes in this bio-relevant media this rate rapidly falls to a rate very similar to the currently marketed form of tranilast. FIG. 40 shows how greatly improved the dissolution rates of the new crystalline tranilast salts of this invention are compared to the crystalline 1:1 tranilast nicotinamide cocrystal of U.S. Pat. No. 9,512,064 B2 in bio-relevant media.

Figure 41:
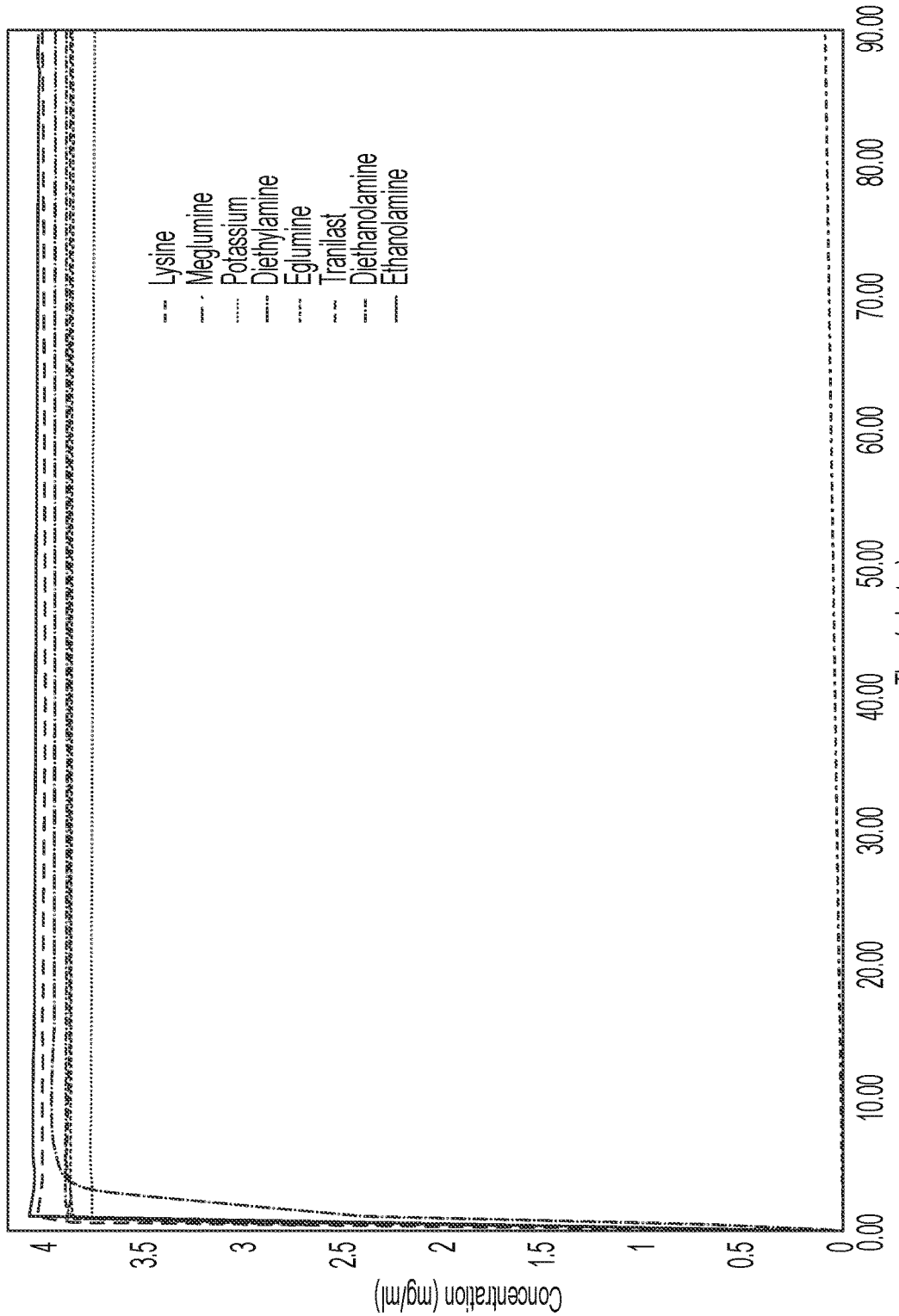
FIG. 41 depicts the dissolution profiles for the crystalline 1:1 tranilast salts versus crystalline tranilast in 5% aqueous dextrose solution at 37° C.

As this invention also relates to a method of preparing a liquid pharmaceutical formulation of tranilast for delivery, for example, as an injectable formulation, a liquid oral formulation or a nebulised inhaled formulation a study was also carried out to explore the dissolution rates of the crystalline tranilast salts of this invention in a suitable media. As liquid pharmaceutical formulations are usually made up in-situ at the bedside for immediate delivery it is important that these new solid forms of tranilast dissolve almost instantaneously for them to be suitable for use in a liquid pharmaceutical formulation. Whilst liquid oral formulations could be achieved by simply dissolving a drug in water prior to administration (the high aqueous solubility of the new crystalline tranilast salts would make this possible), a liquid formulation for inhaled or intravenous delivery requires the dissolution media to be isotonic. This is often achieved by using saline (0.9% sodium chloride in water) as the liquid formulation media. However given the extremely low solubility of the 1:1 tranilast sodium salt, saline is not compatible with tranilast due to the high potential of the formation of the 1:1 tranilast sodium salt and subsequent precipitation from solution. An alternative isotonic media suitable for preparing liquid pharmaceutical formulations for inhaled or intravenous administration is 5% aqueous dextrose solution. Therefore a study was carried out to examine the rate of dissolution of the crystalline 1:1 tranilast N-methylglucamine form II salt, crystalline 1:1 tranilast N-ethylglucamine salt, crystalline 1:1 tranilast L-lysine salt, crystalline 1:1 tranilast potassium monohydrate salt, 1:1 tranilast diethylamine salt, 1:1 tranilast diethanolamine salt and 1:1 tranilast ethanolamine salt compared with crystalline tranilast in 50 ml 5% aqueous dextrose solution using a quantity of each tranilast form equivalent to 200 mg tranilast. The results of this study can be seen in FIG. 41. It can be seen that the crystalline 1:1 tranilast N-methylglucamine form II salt, crystalline 1:1 tranilast N-ethylglucamine salt, crystalline 1:1 tranilast L-lysine salt, crystalline 1:1 tranilast potassium monohydrate salt, crystalline 1:1 tranilast diethanolamine salt and crystalline 1:1 tranilast ethanolamine salt achieve complete dissolution in less than 1 minute, maintaining this same dissolution level after 90 minutes, making them suitable candidates for preparing a liquid pharmaceutical formulation of tranilast for immediate delivery. In contrast, pure crystalline tranilast had only reached a solubility of 1 µg/ml after 1 minute and had only reached 60 µg/ml after 1 hour.

The claimed invention is:

1. A method for the treatment of an allergic disorder, a fibrotic disorder or an inflammatory disorder comprising the step of administering to a patient in need thereof a pharmaceutical composition comprising a crystalline tranilast salt selected from the group consisting of crystalline 1:1 Tranilast N-methylglucamine form I, crystalline 1:1 Tranilast N-methylglucamine form II, crystalline 1:1 Tranilast L-Lysine, crystalline 1:1 Tranilast Diethylamine, crystalline 1:1 Tranilast N-ethylglucamine, crystalline 1:1 Tranilast Potassium Monohydrate, crystalline 1:1 Tranilast Diethanolamine, and crystalline 1:1 Tranilast Ethanolamine and a pharmaceutically acceptable carrier.

2. A method of claim 1, wherein the pharmaceutical composition is a topical formulation.

3. A method of claim 1, wherein the pharmaceutical composition is an inhalable formulation.

4. A method of claim 1, wherein the crystalline tranilast salt is crystalline-1:1 Tranilast N-methylglucamine form I salt.

5. A method of claim 4, wherein the crystalline 1:1 Tranilast N-methylglucamine form I salt is characterized by at least one of:
a powder X-ray diffraction pattern having at least four peaks selected from the peaks at 7.3, 8.4, 9.7, 12.2, 14.4 and 16.2°2θ±0.2°2θ; or
a powder X-ray diffraction pattern substantially similar to FIG. 1; or
an Infrared Spectrum having at least four peaks selected from 1662, 1589, 1507, 1423, 1378, 1272 and 1244 cm$^{-1}$±1 cm$^{-1}$; or
an Infrared Spectrum substantially similar to FIG. 4.

6. A method of claim 1, wherein the crystalline tranilast salt is crystalline 1:1 Tranilast N-methylglucamine form II salt.

7. A method of claim 6, wherein the crystalline 1:1 Tranilast N-methylglucamine form II salt characterized by at least one of:
a powder X-ray diffraction pattern having at least four peaks selected from the peaks at 10.8, 14.0, 14.6, 15.2, 15.9, 16.7, and 18.9°2θ±0.2°2θ; or
a powder X-ray diffraction pattern substantially similar to FIG. 6; or
an Infrared Spectrum having at least four peaks selected from 1655, 1585, 1519, 1417, 1377, 1301 and 1258 cm$^{-1}$±1 cm$^{-1}$; or
an Infrared Spectrum substantially similar to FIG. 9.

8. A method of claim 1, wherein the crystalline tranilast salt is crystalline 1:1 Tranilast L-Lysine salt.

9. A method of claim 1, wherein the crystalline 1:1 Tranilast L-Lysine salt is characterized by at least one of:
a powder X-ray diffraction pattern having at least four peaks selected from the peaks at 11.8, 12.3, 15.1, 16.0, 18.5, 20.9 and 21.5°2θ±0.2°2θ; or
a powder X-ray diffraction pattern substantially similar to FIG. 11; or
an Infrared Spectrum having at least four peaks selected from 1670, 1584, 1493, 1371, 1277, 1254 and 1135 cm$^{-1}$±1 cm$^{-1}$; or
an Infrared Spectrum substantially similar to FIG. 14.

10. A method of claim 1, wherein the crystalline tranilast salt is crystalline 1:1 Tranilast Diethylamine salt.

11. A method of claim 10, wherein the crystalline 1:1 Tranilast Diethylamine salt is characterized by at least one of:
a powder X-ray diffraction pattern having at least four peaks selected from the peaks at 7.6, 12.7, 13.2, 14.5, 16.6, 18.0 and 20.0°2θ±0.2°2θ; or
a powder X-ray diffraction pattern substantially similar to FIG. 15; or
an Infrared Spectrum having at least four peaks selected from 1669, 1618, 1579, 1495, 1419, 1361 and 1155 cm$^{-1}$±1 cm$^{-1}$; or
an Infrared Spectrum substantially similar to FIG. 18.

12. A method of claim 1, wherein the crystalline tranilast salt is crystalline 1:1 Tranilast N-ethylglucamine salt.

13. A method of claim 12, wherein the crystalline 1:1 Tranilast N-ethylglucamine salt is characterized by at least one of:
a powder X-ray diffraction pattern having at least four peaks selected from the peaks at 6.9, 11.1, 13.8, 15.2 16.1 16.8 and 18.2°2θ±0.2°2θ; or
a powder X-ray diffraction pattern substantially similar to FIG. 19; or
an Infrared Spectrum having at least four peaks selected from 1660, 1589, 1423, 1374, 1295, 1273 and 1244 cm$^{-1}$±1 cm$^{-1}$; or
an Infrared Spectrum substantially similar to FIG. 22.

14. A method of claim 1, wherein the crystalline tranilast salt is crystalline 1:1 Tranilast Potassium Monohydrate salt.

15. A method of claim 14, wherein the crystalline 1:1 Tranilast Potassium Monohydrate salt is characterized by at least one of:
a powder X-ray diffraction pattern having at least four peaks selected from the peaks at 7.9, 10.6, 11.7, 14.9, 17.0 19.8 and 20.61°2θ±0.2°2θ;
a powder X-ray diffraction pattern substantially similar to FIG. 23; or
a P21/c space group at a temperature of about 100 K or about 295K; or
an Infrared Spectrum having at least four peaks selected from 1670, 1583, 1492, 1422, 1370, 1155 and 1127 cm$^{-1}$±1 cm$^{-1}$; or
an Infrared Spectrum substantially similar to FIG. 29.

16. A method of claim 1, wherein the crystalline tranilast salt is crystalline 1:1 Tranilast Diethanolamine salt.

17. A method of claim 16, wherein the crystalline 1:1 Tranilast Diethanolamine salt is characterized by at least one of:
a powder X-ray diffraction pattern having at least four peaks selected from the peaks at 7.5, 11.8, 12.5, 16.8, 18.5, 19.1 and 19.9°2θ±0.2°2θ; or
a powder X-ray diffraction pattern substantially similar to FIG. 30; or
an Infrared Spectrum having at least four peaks selected from 1652, 1494, 1422, 1363, 1346, 1266 and 1233 cm$^{-1}$±1 cm$^{-1}$; or
an Infrared Spectrum substantially similar to FIG. 33.

18. A method of claim 1, wherein the crystalline tranilast salt is crystalline 1:1 Tranilast Ethanolamine salt.

19. A method of claim 18, wherein the crystalline 1:1 Tranilast Ethanolamine salt is characterized by at least one of:
a powder X-ray diffraction pattern having at least four peaks selected from the peaks at 10.4, 11.4, 12.2, 14.5, 15.8, 19.5 and 20.4°2θ±0.2°2θ;

a powder X-ray diffraction pattern substantially similar to FIG. 34; or a P21/c space group at a temperature of about 293K; or an Infrared Spectrum having at least four peaks selected from 1668, 1585, 1375, 1359, 1277, 1255 and 1131 cm$^{-1}$±1 cm$^{-1}$; or an Infrared Spectrum substantially similar to FIG. 39.

20. The method of claim 1, wherein the method is for the treatment of an inflammatory disorder.

21. The method of claim 1, wherein the method is for the treatment of an allergic disorder.

22. The method of claim 1, wherein the method is for the treatment of a fibrotic disorder.

* * * * *